(12) United States Patent
Wurtz et al.

(10) Patent No.: US 9,920,075 B2
(45) Date of Patent: Mar. 20, 2018

(54) TRIAZOLOPYRIDINE AND TRIAZOLOPYRIMIDINE INHIBITORS OF MYELOPEROXIDASE

(71) Applicant: BRISTOL-MYERS SQUIBB COMPANY, Princeton, NJ (US)

(72) Inventors: Nicholas R. Wurtz, Pennington, NJ (US); Andrew Quoc Viet, Schwenksville, PA (US); Scott A. Shaw, Lawrence, NJ (US); Benjamin P. Vokits, New York City, NY (US); Ellen K. Kick, Ewing, NJ (US); Meriah Neissel Valente, Bedminster, NJ (US); Andrew K. Dilger, Ewing, NJ (US); Kumar Balashanmuga Pabbisetty, Piscataway, NJ (US); Sutjano Jusuf, Ardmore, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/510,168

(22) PCT Filed: Sep. 9, 2015

(86) PCT No.: PCT/US2015/049091
§ 371 (c)(1),
(2) Date: Mar. 9, 2017

(87) PCT Pub. No.: WO2016/040417
PCT Pub. Date: Mar. 17, 2016

(65) Prior Publication Data
US 2017/0247396 A1     Aug. 31, 2017

Related U.S. Application Data

(60) Provisional application No. 62/048,840, filed on Sep. 11, 2014.

(51) Int. Cl.
*A61K 31/519*     (2006.01)
*C07D 519/00*     (2006.01)
*C07D 471/04*     (2006.01)
*C07D 487/04*     (2006.01)
*A61K 31/437*     (2006.01)

(52) U.S. Cl.
CPC .......... *C07D 519/00* (2013.01); *A61K 31/437* (2013.01); *A61K 31/519* (2013.01); *C07D 471/04* (2013.01); *C07D 487/04* (2013.01)

(58) Field of Classification Search
None
See application file for complete search history.

(56) References Cited

FOREIGN PATENT DOCUMENTS

WO     WO 97/20843          6/1997
WO     WO 2006/062465 A1    6/2006

OTHER PUBLICATIONS

Chawla et. al. Current Research & Information on Pharmaceutical Science, 2004, 5(1), p. 9-12.*
Newman et. al.; Drug Discovery Today; 2003, 8(19) p. 898-905.*

* cited by examiner

*Primary Examiner* — Jeffrey H Murray
(74) *Attorney, Agent, or Firm* — Elliott Korsen

(57) ABSTRACT

The present invention provides compounds of Formula (I): wherein A and $R^1$ are each as defined in the specification, and compositions comprising any of such novel compounds. These compounds are myeloperoxidase (MPO) inhibitors and/or eosinophil peroxidase (EPX) inhibitors, which may be used as medicaments.

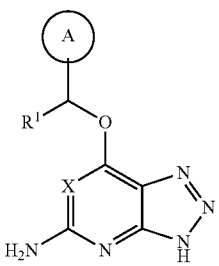

(I)

9 Claims, No Drawings

TRIAZOLOPYRIDINE AND TRIAZOLOPYRIMIDINE INHIBITORS OF MYELOPEROXIDASE

CROSS-REFERENCE TO RELATED APPLICATIONS

This application claims priority from U.S. Provisional Application No. 62/048,840 filed Sep. 11, 2014, the disclosures of which are incorporated herein by reference in their entirety.

FIELD OF THE INVENTION

The present invention relates to novel triazolopyridine and triazolopyrimidine compounds, which are myeloperoxidase (MPO) inhibitors and/or eosinophil peroxidase (EPX) inhibitors, compositions containing them, and methods of using them, for example, for the treatment of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., Nature Med., 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., J. Clin. Invest., 94(1):437-444 (1994)). Moreover, HOCl-modified lipoproteins have been detected in advanced human atherosclerotic lesions (Hazell, L. J. et al., J. Clin. Invest., 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., Am. J. Pathol., 158(3):879-891 (2001); Tavora, F. R., BMC Cardiovasc. Disord., 9:27 (Jun. 23, 2009)).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., Arterioscler. Thromb. Vasc. Biol., 25(6):1102-1111 (2005); Nicholls, S. J. et al., JLR, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., J. Clin. Invest., 99(9):2075-2081 (1997)).

ApoA-I isolated from atherosclerotic lesions is modified by reactive chlorine and nitrogen species as well as by reactive carbonyls (Pennathur, S. et al., J. Biol. Chem., 279:42977-42983 (2004); Shao, B. et al., J. Biol. Chem., 279:7856-7866 (2004); Zheng, L. et al., J. Clin. Invest., 114(4):529-541 (2004); Shao, B. et al., JBC in press (2012)). Chlorotyrosine modification of apoA1, the main apolipoprotein of HDL cholesterol, was associated with impaired cholesterol acceptor function (Bergt, C. S. et al., Proc. Natl. Acad. Sci. USA, 101(35):13032-13037 (2004); Zheng, L. et al., J. Clin. Invest., 114(4):529-541 (2004)). Thus, oxidation of apoA-I amino acid residues by the MPO—$H_2O_2$—$Cl^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., J. Clin. Invest., 2075-2081 (1997)). LDL particles exposed to MPO in vitro become aggregated, leading to facilitated uptake via macrophage scavenger receptors and foam cell formation (Hazell, L. J. et al., Biochem. J., 290 (Pt. 1):165-172 (1993); Podrez, E. A. et al., J. Clin. Invest. 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini, L. W. et al., J. Lipid Res., 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., JAMA, 286(17):2136-2142 (2001)). Moreover, in three large prospective studies plasma levels of MPO predicted the risk of future coronary events or revascularization (Baldus, S. et al., Circulation, 108(12):1440-1445 (2003); Brennan, M. et al., N. Engl. J. Med., 349(17):1595-1604 (2003); Kohli, P. et al., Circulation, 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., J. Am. Coll. Cardiol., 50:159-165 (2007); Karakas et al., J. Int. Med., 271:43-50 (2011)). Interestingly, MPO deficient humans are less affected by cardiovascular disease than controls with normal MPO levels (Kutter, D. et al., Acta Haematol., 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., Am. Heart J., 142(2):336-339 (2001); Makela, R. et al., Lab. Invest. 83(7):919-925 (2003); Asselbergs, F. W. et al., Am. J. Med., 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., J. Exp. Med., 197:615-624 (2003)) and an ischemia reperfusion model (Vasilyev, N. et al., Circulation, 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., *Am. J. Cardiol.*, 98:796-799 (2006)). Studies also showed that systemic MPO in subjects with myocardial infarction (MI) (Mocatta, T. J. et al., *J. Am. Coll. Cardiol.*, 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO or EPX may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J. Neurochem.*, 90:724-733 (2004)). In an animal model of Parkinson's disease, increased levels of chlorotyrosine and HOCl-modified proteins in brain tissues have been reported (Choi, D. K. et al., *J. Neurosci.*, 25(28):6394-6600 (2005)). In asthmatic patients the level of bromotyrosine, a molecular fingerprint of eosinophil-catalyzed oxidation was associated with symptom severity (Wedes, S. H. et al., *J. Pediatr.*, 248-255 (2011)). Upon allergen challenge, a model that elicits primarily a strong eosinophilic response, lung segments of asthmatic subjects exhibit a >10 fold increase in bronchioalveolar lavage 3-bromotyrosine an indicator of eosinophil activity vs. a 3-fold increase in 3-chlorotyrosine characteristic of MPO activity (Wu, W. et al., *JCI*, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J. Am. Soc., Nephrol.*, 142-151 (2009). In addition MPO activity and 3-chlorotyrosine levels were also increased during hemodialysis in patients with end-stage renal disease (Delporte, C. et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J. Pathol.*, 201:17-27 (2003); Carlson, M. et al., *Am. J. Gastrol.*, 94(7):1876-1883 (1999)) and in synovial fluids of rheumatoid arthritis patients (Edwards, S. W. et al., *Biochem. J.*, 250:81-85 (1988); Nucombe, H. L. et al., *Ann. Rheum. Dis.*, 50:237-242 (1991)).

Thus, there is considerable evidence that MPO and/or EPX derived oxidants contribute to tissue injury in chronic inflammatory disorders. MPO and/or EPX inhibitors are anticipated to reduce the levels of oxidants and tissue injury associated with the progression of these diseases.

SUMMARY OF THE INVENTION

The present disclosure provides novel triazolopyridine and triazolopyrimidine compounds, including stereoisomers, tautomers, pharmaceutically acceptable salts, polymorphs, or solvates thereof, which are useful as MPO inhibitors and/or EPX inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The compounds of the invention may be used in the treatment of diseases or disorders associated with the activity of MPO and/or EPX.

The compounds of the invention may be used in therapy.

The compounds of the invention may be used for the manufacture of a medicament for the treatment of diseases or disorders associated with the activity of MPO and/or EPX.

Examples of diseases or disorders associated with the activity of MPO and/or EPX include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

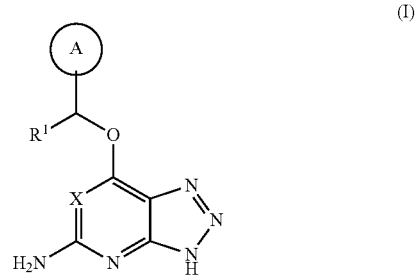

or a stereoisomer, a tautomer, a pharmaceutically acceptable salt, a polymorph, or a solvate thereof, wherein:

ring A is independently a 5- to 10-membered heterocycle comprising carbon atoms and 1-4 heteroatoms selected from N, $NR^a$, O, and $S(O)_p$; wherein said heterocycle is substituted with 0-1 $R^2$ and 0-4 $R^3$;

X is independently CH or N;

$R^1$ is independently selected from: H, CN, $C_{1-6}$ alkyl, and $C_{1-6}$ haloalkyl;

provided that ring A is other than thienyl substituted with halogen, when X is N and $R^1$ is H;

$R^2$ is independently selected from: $SF_5$, $-(CH_2)_rOH$, $-(CH_2)_nR^4$, and $-(CH_2)_n(X_1)_n(CH_2)_nR^5$;

$X_1$ is independently selected from: O, S, CO and $SO_2$;

$R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);

$R^4$ is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, CN, $CO_2(C_{1-4}$ alkyl), $NO_2$, $NR^6R^7$, $CONR^6R^7$, $NHCOR^8$, $NHCO_2R^8$, $COR^{10}$, $SO_2NR^9R^{10}$, and $S(O)_pR^8$;

$R^5$ is independently selected from: $C_{3-10}$ carbocycle substituted with 0-2 $R^{11}$, phenyl substituted with 0-3 $R^{11}$ and 0-1 $R^{12}$, and 5- to 10-membered heterocycle comprising carbon atoms and 1-4 heteroatoms selected from N, $NR^a$, O, and $S(O)_p$; wherein said heterocycle is substituted with 0-2 $R^{11}$ and 0-1 $R^{13}$;

$R^6$ is, at each occurrence, independently selected from: H, $C_{1-4}$ haloalkyl, $C_{1-6}$ alkyl substituted with 0-2 $R^{15}$, —$(CH_2)_t$—$C_{3-6}$ cycloalkyl substituted with 0-1 $R^{14}$), —$(CHR^b)_n$-(phenyl substituted with 0-1 $R^{16}$), —$(CH_2)_t$-(phenyl substituted with 0-1 $R^{16}$), —$(CH_2)_t$-(a 5- to 10-membered heterocycle comprising carbon atoms and 1-4 heteroatoms selected from N, $NR^a$, O, and $S(O)_p$, wherein said heterocycle is substituted with 0-1 $R^{17}$);

$R^7$ is, at each occurrence, independently selected from: H and $C_{1-4}$ alkyl substituted with $R^{11}$;

$R^8$ is, at each occurrence, independently selected from: $C_{1-4}$ alkyl, —$(CH_2)_t$—$C_{3-6}$ cycloalkyl, and —$(CH_2)_t$-phenyl;

$R^9$ is, at each occurrence, independently selected from: H and $C_{1-4}$ alkyl;

$R^{10}$ is, at each occurrence, independently selected from: $R^8$ and H;

$R^{11}$ is, at each occurrence, independently selected from: OH, $NH_2$, halogen, $C_{1-4}$ alkoxy, $C_{1-4}$ haloalkyl, and $C_{1-4}$ haloalkoxy;

$R^{12}$ is independently selected from: halogen, CN, $C_{1-4}$ alkyl, $C_{1-4}$ alkoxy, $C_{1-4}$ haloalkyl, $C_{1-4}$ haloalkoxy, $C_{1-4}$ alkylthio, OH, $CH_2OH$, $CO_2H$, $CO_2(C_{1-4}$ alkyl), $NH_2$, $CH_2NH_2$, $N(C_{1-4}$ alkyl)$_2$, $CH_2N(C_{1-4}$ alkyl)$_2$, $CONH_2$, $CON(C_{1-4}$ alkyl)$_2$, $SO_2NH_2$, $SO_2NH(C_{1-4}$ alkyl), $SO_2N(C_{1-4}$ alkyl)$_2$, CONHPh, NHCOPh, —$(CH_2)_n$—$C_{3-6}$ carbocycle substituted with 0-2 $R^c$, (a 5- to 6-membered heterocycle comprising carbon atoms and 1-4 heteroatoms selected from N, $NR^a$, O, and $S(O)_p$, wherein said heterocycle is substituted with 0-2 $R^c$),

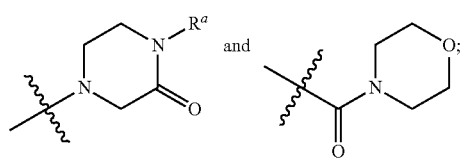

$R^{13}$ is independently selected from: $R^{12}$ and =O;

$R^{14}$ and $R^{16}$ are, at each occurrence, independently selected from: halogen, $C_{1-4}$ alkyl, $C_{1-4}$ alkoxy, $C_{1-4}$ haloalkyl, $C_{1-4}$ haloalkoxy, OH, $CH_2OH$, $N(C_{1-4}$ alkyl)$_2$, $CONH_2$, $CONH(C_{1-4}$ alkyl), $CON(C_{1-4}$ alkyl)$_2$, $OCH_2CONH_2$, $NHCO(C_{1-4}$ alkyl), $NHCO_2(C_{1-4}$ alkyl), $SO_2(C_{1-4}$ alkyl), —$(CH_2)_n$-phenyl, —O—$(CH_2)_n$-phenyl, and pyridylmethyl;

$R^{15}$ is, at each occurrence, independently selected from: OH, $C_{1-4}$ alkoxy, $C_{1-4}$ haloalkyl, $C_{1-4}$ haloalkoxy, $N(C_{1-4}$ alkyl)$_2$, $CONH_2$, $CONH(C_{1-4}$ alkyl), and $CON(C_{1-4}$ alkyl)$_2$;

$R^{17}$ is independently selected from: $R^{14}$ and =O;

$R^a$ is, at each occurrence, independently selected from the group consisting of H, $C_{1-4}$ alkyl, $CO(C_{1-4}$ alkyl), $CO_2(C_{1-4}$ alkyl), $SO_2(C_{1-4}$ alkyl), —$(CH_2)_n$-(pyrrolidinyl substituted with 0-1 $R^c$), —$(CH_2)_n$-(phenyl substituted with 0-1 $R^c$), and —CO(—$(CH_2)_n$-phenyl substituted with 0-1 $R^c$);

$R^b$ is, at each occurrence, independently selected from: H and $C_{1-4}$ alkyl;

$R^c$ is, at each occurrence, independently selected from: OH, $NH_2$, $C_{1-4}$ alkyl, halogen, $C_{1-4}$ alkoxy, $C_{1-4}$ haloalkyl, $C_{1-4}$ haloalkoxy, pyrrolidinyl, —$(CH_2)_n$-piperidinyl, Ph, and OPh;

n is, at each occurrence, independently selected from: 0 and 1;

p is, at each occurrence, independently selected from: 0, 1 and 2; and t is, at each occurrence, independently selected from: 0, 1, 2, 3 and 4.

In a second aspect, the present invention includes a compound of Formula (I), or a stereoisomer, a tautomer, a pharmaceutically acceptable salt, a polymorph, or a solvate thereof, within the scope of any of the above aspects, wherein:

$R^2$ is independently selected from: halogen, CN, $CH_2OH$, $C_{1-4}$ alkyl, —$CH_2$—$C_{1-4}$ alkoxy, $C_{1-4}$ alkoxy, $C_{1-4}$ haloalkyl, $C_{1-4}$ haloalkoxy, $C_{1-4}$ haloalkylthio, $SF_5$, $CO_2(C_{1-4}$ alkyl), $NR^6R^7$, $CONR^6R^7$, —$NHCO(C_{1-4}$ alkyl), $NO_2$, $SO_2NR^8R^9$, $SO_2R^8$, —$(O)_{0-1}$—$(C_{3-6}$ cycloalkyl), —$(O)_{0-1}$—$(CH_2)_{0-1}$-(phenyl substituted with 0-1 $R^{11}$ and 0-1 $R^{12}$), and —$(CH_2)_{0-1}$-(a heterocycle substituted with 0-1 $R^{11}$ and 0-1 $R^{13}$, wherein said heterocycle is a 5- to 10-membered heterocycle comprising carbon atoms and 1-4 heteroatoms selected from N, $NR^a$, O, and S);

$R^6$ is independently selected from: H, $C_{1-4}$ haloalkyl, and $C_{1-6}$ alkyl;

$R^{12}$ and $R^{13}$ are, at each occurrence, independently selected from: halogen, CN, $C_{1-4}$ alkyl, $C_{1-4}$ alkoxy, $C_{1-4}$ haloalkyl, $C_{1-4}$ haloalkoxy, $CH_2OH$, $CO_2(C_{1-4}$ alkyl), $SO_2(C_{1-4}$ alkyl), $C_{3-6}$ cycloalkyl, $CON(C_{1-4}$ alkyl)$_2$, $SO_2NH_2$, $SO_2NH(C_{1-4}$ alkyl), $SO_2N(C_{1-4}$ alkyl)$_2$, Ph, Bn, CONHPh, NHCOPh, pyrazolyl, pyrrolidinyl, piperidinyl, morpholinyl, piperazinyl,

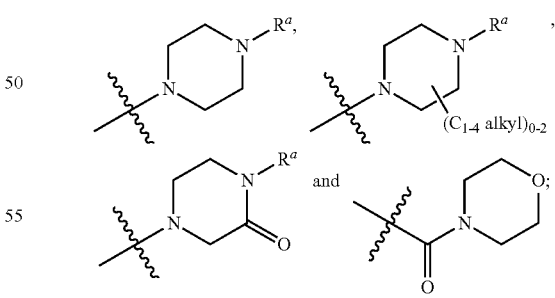

$R^{15}$ is, at each occurrence, independently selected from: OH, $C_{1-4}$ alkyl, $C_{1-4}$ alkoxy, $C_{1-4}$ haloalkyl, $N(C_{1-4}$ alkyl)$_2$, $CONH_2$, $CONH(C_{1-4}$ alkyl), and $CON(C_{1-4}$ alkyl)$_2$; and $R^{16}$ is independently selected from: halogen, $C_{1-4}$ alkoxy, and $SO_2(C_{1-4}$ alkyl).

In a third aspect, the present disclosure provides a compound of Formula (II):

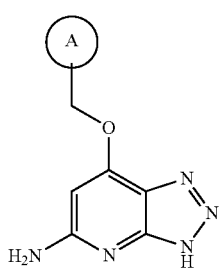
(II)

or a stereoisomer, a tautomer, a pharmaceutically acceptable salt, a polymorph, or a solvate thereof, within the scope of any of the first and second aspects.

In a fourth aspect, the present disclosure provides a compound of Formula (IIa):

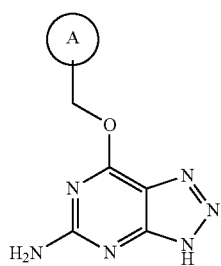
(IIa)

or a stereoisomer, a tautomer, a pharmaceutically acceptable salt, a polymorph, or a solvate thereof, within the scope of any of the first and second aspects; provided that ring A is other than thienyl substituted with halogen.

In a fifth aspect, the present disclosure provides a compound of Formula (I), (II) or (IIa), or a stereoisomer, a tautomer, a pharmaceutically acceptable salt, a polymorph, or a solvate thereof, within the scope of any of the above aspects; wherein:

ring A is independently selected from:

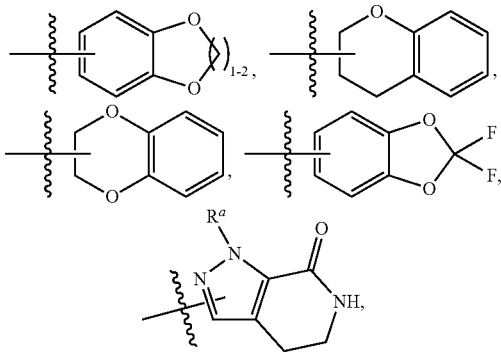

and a 5- to 10-membered heteroaryl comprising carbon atoms and 1-4 heteroatoms selected from N, NR$^a$, O, and S; wherein each ring moiety is substituted with 0-1 R$^2$ and 0-2 R$^3$; provided that ring A is other than thienyl substituted with halogen, when X is N and R$^1$ is H in Formula (I);

R$^2$ is independently selected from: SF$_5$, halogen, CN, CH$_2$OH, C$_{1-4}$ alkyl, C$_{1-4}$ alkoxy, C$_{1-4}$ haloalkyl, C$_{1-4}$ haloalkoxy, C$_{1-4}$ haloalkylthio, —CH$_2$(C$_{1-4}$ alkoxy), —(O)$_{0-1}$—(C$_{3-6}$ cycloalkyl), —(O)$_{0-1}$—(CH$_2$)$_{0-1}$-(phenyl substituted with 0-1 R$^{11}$ and 0-1 R$^{12}$), (pyridyl substituted with 0-1 R$^{11}$ and 0-1 R$^{13}$), and

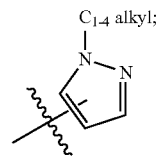
C$_{1-4}$ alkyl;

R$^3$ is, at each occurrence, independently selected from: halogen, CN, C$_{1-4}$ alkyl, C$_{1-4}$ alkoxy, C$_{1-4}$ haloalkyl, C$_{1-4}$ haloalkoxy, NO$_2$, CONH$_2$, and SO$_2$(C$_{1-4}$ alkyl);

R$^{11}$ is, at each occurrence, independently selected from: halogen, NH$_2$, C$_{1-4}$ alkoxy, C$_{1-4}$ haloalkyl, and C$_{1-4}$ haloalkoxy;

R$^{12}$ and R$^{13}$ are, at each occurrence, independently selected from: halogen, CN, C$_{1-4}$ alkyl, C$_{1-4}$ alkoxy, C$_{1-4}$ haloalkyl, C$_{1-4}$ haloalkoxy, CH$_2$OH, CO$_2$(C$_{1-4}$ alkyl), SO$_2$(C$_{1-4}$ alkyl), C$_{3-6}$ cycloalkyl, CON(C$_{1-4}$ alkyl)$_2$, SO$_2$NH$_2$, SO$_2$NH(C$_{1-4}$ alkyl), SO$_2$N(C$_{1-4}$ alkyl)$_2$, Ph, CONHPh, NHCOPh, pyrazolyl,

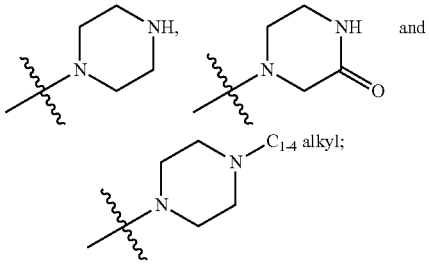

R$^a$ is, at each occurrence, independently selected from the group consisting of H, C$_{1-4}$ alkyl, CO(C$_{1-4}$ alkyl), CO$_2$(C$_{1-4}$ alkyl), SO$_2$(C$_{1-4}$ alkyl), —(CH$_2$)$_n$—(C$_{3-6}$ cycloalkyl substituted with 0-1 R$^c$), —(CH$_2$)$_n$-(phenyl substituted with 0-1 R$^c$), —CO(—(CH$_2$)$_n$-phenyl), —(CH$_2$)$_n$-(pyrrolidinyl substituted with 0-1 R$^c$), —(CH$_2$)$_n$-(imidazolyl substituted with 0-1 R$^c$), —(CH$_2$)$_n$-(piperidinyl substituted with 0-1 R$^c$), —(CH$_2$)$_n$-(pyridyl substituted with 0-1 R$^c$), and —(CH$_2$)$_n$-(pyrimidinyl substituted with 0-1 R$^c$).

In a sixth aspect, the present disclosure includes a compound of Formula (I) (II) or (IIa), or a stereoisomer, a tautomer, a pharmaceutically acceptable salt, a polymorph, or a solvate thereof, within the scope of any of the above aspects wherein:

ring A is independently selected from: furanyl, oxazolyl, thiazolyl, isoxazolyl, oxadiazolyl, pyridyl, pyrimidinyl, benzofuranyl, quinolinyl

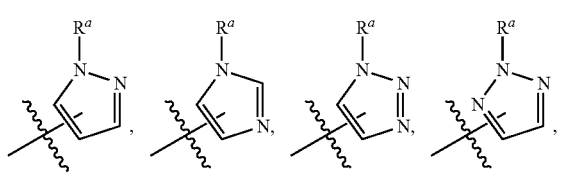

-continued

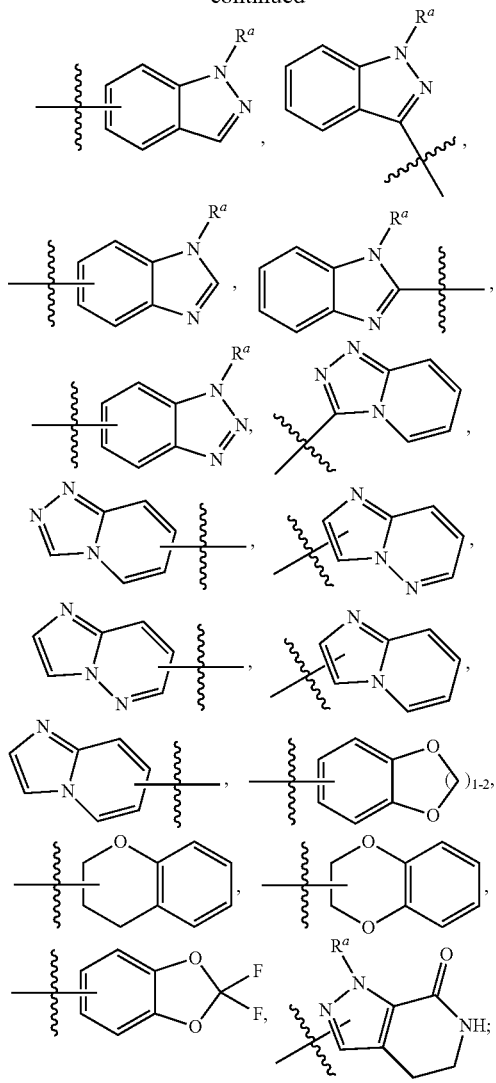

wherein each ring moiety is substituted with 0-1 $R^2$ and 0-1 $R^3$;

$R^2$ is, at each occurrence, independently selected from: $SF_5$, halogen, $C_{1-4}$ alkyl, $C_{1-4}$ alkoxy, $C_{1-4}$ haloalkyl, $C_{1-4}$ haloalkoxy, $CH_2OH$, —$CH_2(C_{1-4}$ alkoxy), —$(O)_{0-1}$—$(C_{3-6}$ cycloalkyl), —$(O)_{0-1}$—$(CH_2)_{0-1}$-(phenyl substituted with 0-2 $R^{12}$), pyridyl substituted with 0-1 $R^{13}$, and

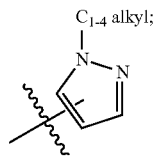

$R^3$ is, at each occurrence, independently selected from: CN, halogen, $C_{1-4}$ alkyl, and $C_{1-4}$ haloalkyl; and $R^{12}$ and $R^{13}$ are, at each occurrence, independently selected from: halogen, CN, $C_{1-4}$ alkyl, $C_{1-4}$ alkoxy, $C_{1-4}$ haloalkyl, $CH_2OH$, $NH(C_{1-4}$ alkyl), $SO_2(C_{1-4}$ alkyl), $C_{3-6}$ cycloalkyl,

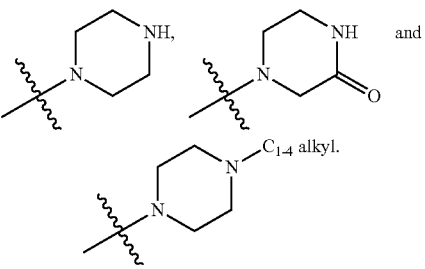

In a seventh aspect, the present disclosure includes a compound of Formula (I) or (II), or a stereoisomer, a tautomer, a pharmaceutically acceptable salt, a polymorph, or a solvate thereof, within the scope of any of the first, second, third, fifth and sixth aspects wherein:

ring A is independently selected from: furanyl, oxazolyl, thiazolyl, isoxazolyl, oxadiazolyl, pyridyl, pyrimidinyl, quinolinyl,

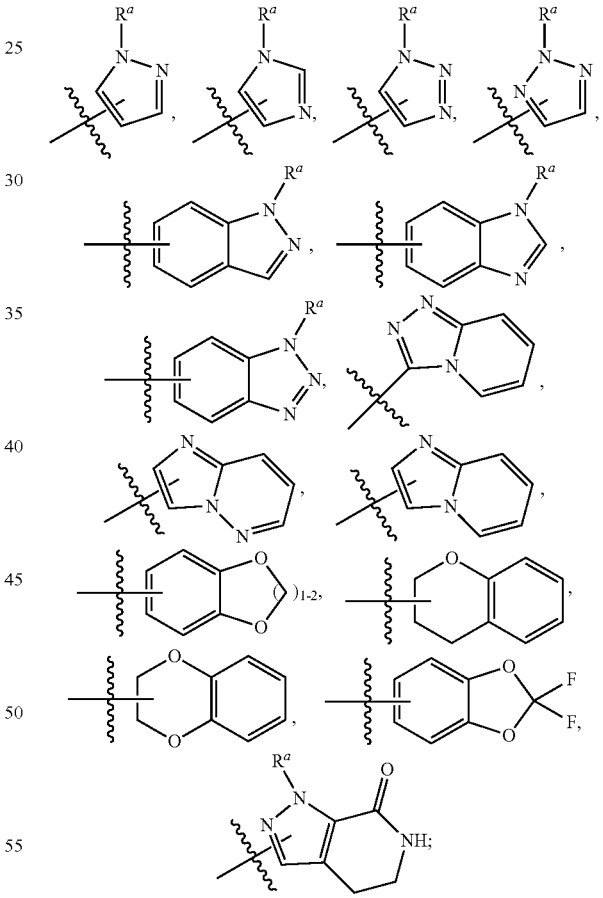

wherein each ring moiety is substituted with 0-1 $R^2$ and 0-1 $R^3$.

In an eighth aspect, the present disclosure includes a compound of Formula (I) or (IIa), or a stereoisomer, a tautomer, a pharmaceutically acceptable salt, a polymorph, or a solvate thereof, within the scope of any of the first, second, fourth, fifth and sixth aspects wherein:

ring A is independently selected from: isoxazolyl, thiazolyl, pyridyl, benzofuranyl, quinolinyl,

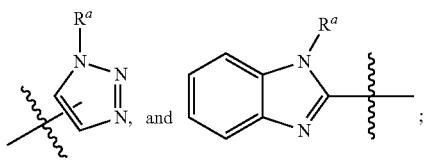

wherein each ring moiety is substituted with 0-1 $R^2$ and 0-1 $R^3$;

$R^2$ is, at each occurrence, independently selected from: halogen, $C_{1-4}$ alkyl, $C_{1-4}$ alkoxy, $C_{1-4}$ haloalkyl, $C_{1-4}$ haloalkoxy, —$(O)_{0-1}$—$(CH_2)_{0-1}$-(phenyl substituted with 0-2 $R^{12}$), and pyridyl substituted with 0-1 $R^{13}$;

$R^{12}$ and $R^{13}$ are, at each occurrence, independently selected from: halogen, CN, $C_{1-4}$ alkyl, $C_{1-4}$ alkoxy, and $C_{1-4}$ haloalkyl; and $R^a$ is, at each occurrence, independently selected from the group consisting of H, $C_{1-4}$ alkyl, and —$(CH_2)_n$-(phenyl substituted with 0-1 $R^c$).

In a ninth aspect, the present invention provides a compound selected from the exemplified examples or a stereoisomer, a tautomer, a pharmaceutically acceptable salt, a polymorph, or a solvate thereof.

In another aspect, the present invention provides a compound selected from any subset list of compounds within the scope of the ninth aspect.

In another embodiment, the compounds of the present invention have $IC_{50}$ values ≤10 μM, using the MPO peroxidation assay disclosed herein, preferably, $IC_{50}$ values ≤3 μM, more preferably, $IC_{50}$ values ≤0.3 μM, even more preferably, $IC_{50}$ values ≤0.1 μM.

In another embodiment, the compounds of the present invention have $IC_{50}$ values ≤10 μM, using the MPO chlorination assay disclosed herein, preferably, $IC_{50}$ values ≤3 μM, more preferably, $IC_{50}$ values ≤0.3 μM, even more preferably, $IC_{50}$ values ≤0.1 μM.

In another embodiment, the compounds of the present invention have $IC_{50}$ values ≤10 μM, using the EPX bromination assay described herein, preferably, $IC_{50}$ values ≤3 μM, more preferably, $IC_{50}$ values ≤0.3 μM, even more preferably, $IC_{50}$ values ≤0.1 μM.

II. Other Embodiments of the Invention

In another embodiment, the present invention provides a composition comprising at least one of the compounds of the present invention or a stereoisomer, a tautomer, a pharmaceutically acceptable salt, a polymorph, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, a polymorph, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment of diseases or disorders associated with the activity of MPO and/or EPX, alone, or optionally in combination with another compound of the present invention and/or at least one other type of therapeutic agent.

In another embodiment, the present invention provides a method for the treatment of diseases or disorders associated with the activity of MPO and/or EPX, comprising administering to a patient in need of such treatment a therapeutically effective amount of at least one of the compounds of the present invention, alone, or optionally in combination with another compound of the present invention and/or at least one other type of therapeutic agent.

In another embodiment, the present invention provides a method for the treatment of diseases or disorders associated with the activity of MPO and/or EPX, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment of diseases or disorders associated with the activity of MPO and/or EPX, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of diseases or disorders associated with the activity of MPO and/or EPX.

Examples of diseases or disorders associated with the activity of MPO and/or EPX that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, diuretics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, anti-hypercholesterolemic agents, cholesterol biosynthesis inhibitors (such as HMG CoA reductase inhibitors), acyl-coenzyme A:cholesterol acyltransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diuretics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 15th Edition, John Wiley & Sons, Inc., New York (2007). "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated, or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in, Allen, L. V., Jr., ed., *Remington: The Science and Practice of Pharmacy,* 22nd Edition, Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984); and f) Rautio, J., ed., *Prodrugs and Targeted Delivery* (*Methods and Principles in Medicinal Chemistry*), Vol 47, Wiley-VCH (2011).

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Ac: Acetic (AcOH: acetic acid, EtOAc: ethyl acetate)
ACN (or MeCN): acetonitrile
APF: aminophenyl fluorescein
BINAP: 2,2'-bis(diphenylphosphino)-1,1'-binaphthyl
Bn: benzyl
Boc: tert-butyl carbonyl
Boc$_2$O: Di-tert-butyl dicarbonate
Bu: butyl
dba (Pd$_2$(dba)$_3$): dibenzylideneacetone
DCM: dichloromethane
DEAD: diethyl azodicarboxylate
DIEA: diisopropylethylamine
DMAP: 4-dimethylaminopyridine
DME: Dimethoxyethane
DMF: dimethylformamide
DMSO: dimethyl sulfoxide
dppf (PdCl$_2$(dppf)): 1,1'-bis(diphenylphosphino)ferrocene
Et: ethyl (EtOH: ethanol, EtOAc: ethyl acetate)
HATU: 2-(7-Aza-1H-benzotriazole-1-yl)-1,1,3,3-tetramethyluronium hexafluorophosphate
hex: hexanes
HBTU: 2-(1H-Benzotriazole-1-yl)-1,1,3,3-tetramethyluronium hexafluorophosphate
i-Bu: isobutyl
i-Pr: isopropyl
Me: methyl (MeOH: methanol, MeCN: acetonitrile)

NMP: N-Methylpyrrolidone
Ph: phenyl
Pr: propyl
t-Bu: tert-butyl
TCA: Trichloroacetic acid
TFA: Trifluoroacetic acid
THF: tetrahydrofuran
Trityl or Trt: triphenylmethyl
Ts: tosyl Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York, N.Y. (1999). Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts, P. G. M. et al., *Protecting Groups in Organic Synthesis*, 4th Edition, Wiley (2007)). Protecting groups incorporated in making of the triazolopyridine and triazolopyrimidine compounds of the present invention, such as the trityl protecting group, may be shown as one regioisomer but may also exist as a mixture of regioisomers.

Compounds having the general Formula (I):

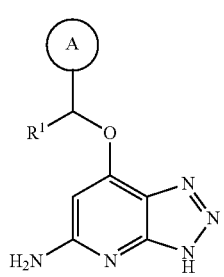

(I)

wherein A and R$^1$ are each defined above, can be prepared by the following one or more of the synthetic Schemes.

Scheme 1

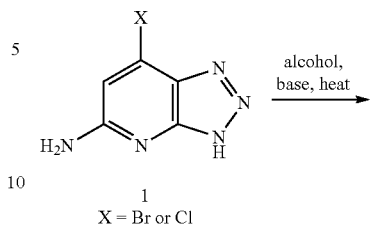

X = Br or Cl

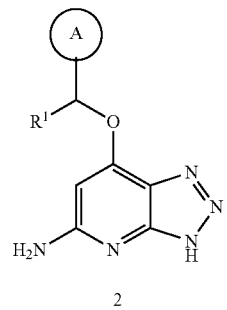

A mixture of chloro or bromotriazolopyridine 1 with a base such as sodium hydride or cesium carbonate and an alcohol can be heated in a suitable solvent such as DMSO to afford triazolopyridine 2. The synthesis of chloro or bromotriazolopyridine 1 is provided in the methods below as Intermediate 2 and Intermediate 3, respectively. Many alcohols are commercially available and can also be prepared by methods known in the art.

Scheme 2

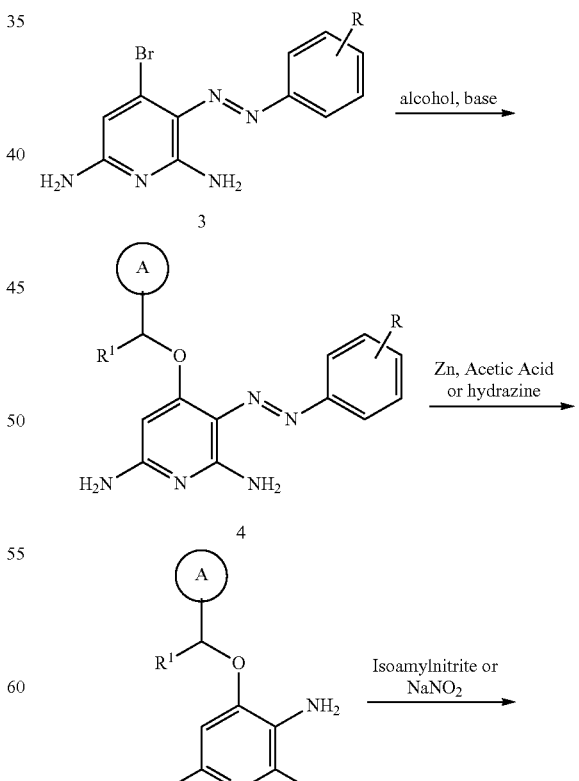

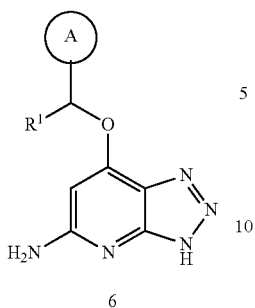

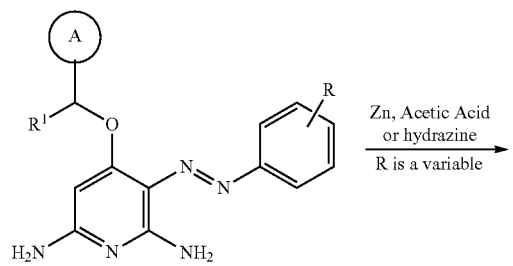

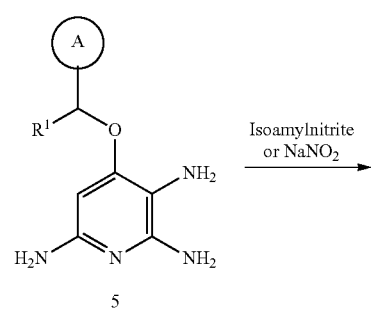

Alternatively to Scheme 1, diaza intermediate 3 can be heated with a base such as cesium carbonate and an alcohol in a solvent such as DMSO to yield ether 4. Intermediate 4 can be converted to triamine 5 by heating with hydrazine or with zinc in a mixture of acetic acid and ethanol or methanol. The triamine can be cyclized with isoamylnitrite or sodium nitrite or other reagent with similar reactivity to yield triazolopyridine 6. The synthesis of an example diaza intermediate 3 is described below in the synthesis methods as Intermediate 1.

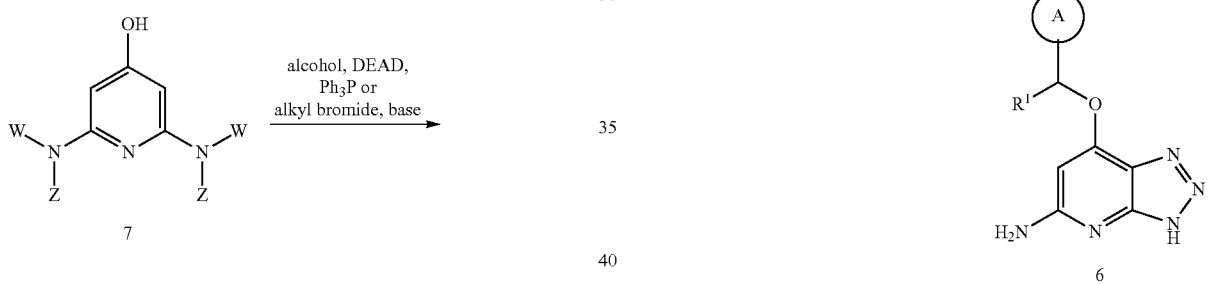

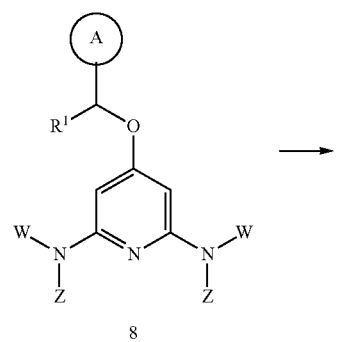

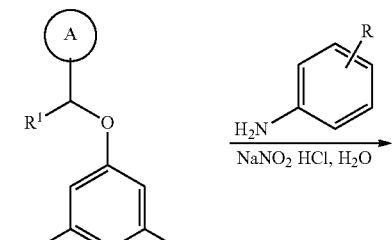

Pyridine ethers can also be prepared via Mitsunobu reaction or alkylation using Intermediate 7 where W is a suitable protecting group and Z is a protecting group or H. One example of a protecting group used in the invention is where W and Z are both equal to Boc. Once the protecting groups are removed, the subsequent pyridine diamine 9 can be diazotized with a diazonium salt prepared from anilines such as para-chloro aniline. The diaza species 4 can be converted into the desired triazolopyrine using the same synthetic sequence as shown in Scheme 2.

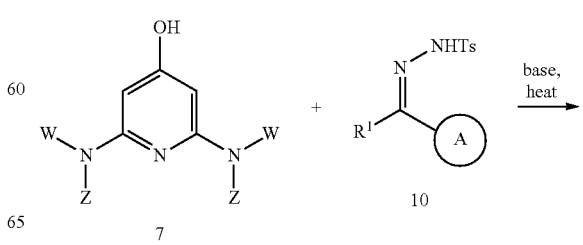

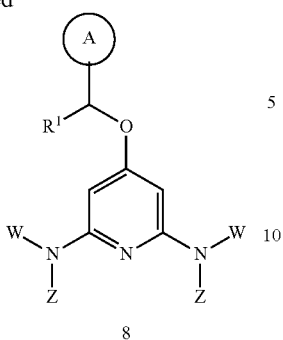

8

The ether linkage can also be formed using a reductive coupling of a tosylhydrazone (*Angew. Chem. Int. Ed.*, 49:4993-4996 (2010)) by heating hydrazone 10 with Intermediate 7 in the presence of base as depicted in Scheme 4. The resulting ether 8 can be converted into the corresponding triazolopyridine via the sequence shown in Scheme 3.

Scheme 5

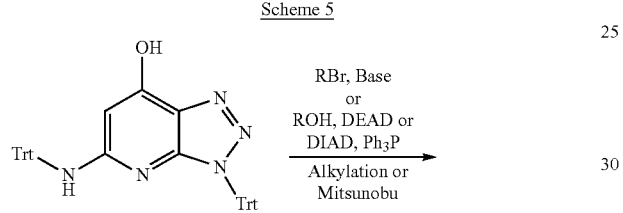

Intermediate 5

11

6

Pyridine ethers can also be prepared via Mitsunobu reaction or alkylation using trityl protected Intermediate 5. The resulting pyridyl ether 11 can be deprotected with an acid such as TFA and the trityl cation can be quenched by the addition of a scavenger such as triethyl silane followed by concentrated and purification to yield the desired compound.

The pyridyl ethers can also be formed by other methods known in the literature. For example, the appropriately protected pyridyl halide and an alcohol can be coupled using transition metal catalysis. (see *Angew. Chem. Int. Ed.*, 50:9943-9947 (2011); *Angew. Chem. Int. Ed.*, 48:6954-6971 (2009) and references therein).

Scheme 6

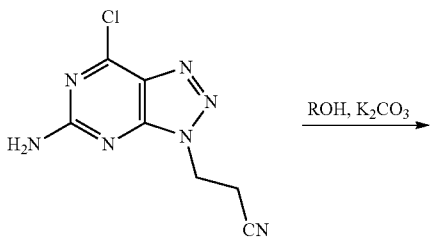

Intermediate 6

12

13

The thiopyrimidines can be prepared by treating Intermediate 6 with an appropriate alcohol (1-3 eq) and $K_2CO_3$ (2-10 eq) in DME and heating for 8-16 hours to yield ether 12. The ethyl cyano protecting group can be removed by treatment with potassium tert-butoxide (1-5 eq) to produce triazolopyrimidine 13.

The above compounds can be accessed through other starting materials such as 3-nitropyridines but these compounds should be handled with caution since derivatives can be highly energetic.

General Methods

The following methods were used in the exemplified Examples, except where noted otherwise.

Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. For highly polar amines, gradients of DCM and 1M $NH_3$ in MeOH were used. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (90% water, 10% ACN, 0.1% TFA) and Solvent B (10% water, 90% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM NH$_4$OAc) and Solvent B (98% ACN, 5% water, 10 mM NH$_4$OAc) or with gradients of Solvent A (95% water, 2% ACN, 0.1% NH$_4$OH) and Solvent B (98% ACN, 2% water, 0.1% NH$_4$OH).

Analytical HPLC: Methods Employed in Characterization of Examples

Products were analyzed by reverse phase analytical HPLC: carried out on a Shimadzu Analytical HPLC: system running Discovery VP software. RT=retention time.

Method A: Linear gradient of 0 to 100% B over 10 min, with 5 min hold at 100% B
UV visualization at 254 nm
Column: SunFire C18; 3.5 µm; 4.6×150 mm
Flow rate: 1 mL/min (Method A)
Solvent A: 10% acetonitrile, 90% water, 0.05% TFA
Solvent B: 10% water, 90% acetonitrile, 0.05% TFA Method B: Linear gradient of 0 to 100% B over 10 min, with 5 min hold at 100% B
UV visualization at 254 nm
Column: XBridge Phenyl 3.5 µm; 4.6×150 mm
Flow rate: 1 mL/min (Method A)
Solvent A: 10% acetonitrile, 90% water, 0.05% TFA
Solvent B: 10% water, 90% acetonitrile, 0.05% TFA Method C: Linear gradient: 0-100% B over 3 min, then a 0.75-min hold at 100% B
Temperature: 50° C.
UV visualization at 220 nm
Column: Waters Acquity UPLC BEH C18, 1.7 µm; 2.1×50 mm
Flow: 1.11 mL/min (Method A)
Solvent A: 5:95 acetonitrile:water with 0.1% TFA
Solvent B: 95:5 acetonitrile:water with 0.1% TFA Method D: Linear gradient: 0-100% B over 3 min, then a 0.75-min hold at 100% B
Temperature: 50° C.
UV visualization at 220 nm
Column: Waters Acquity UPLC BEH C18, 1.7 µm; 2.1×50 mm
Flow: 1.11 mL/min (Method A)
Solvent A: 5:95 acetonitrile:water with 10 mM ammonium acetate
Solvent B: 95:5 acetonitrile:water with 10 mM ammonium acetate Method E: Linear Gradient: 0.5 min hold at 0% B, 0-100% B over 4 minutes, then a 0.5-min hold at 100% B
Column: Waters BEH C18, 2.0×50 mm, 1.7-µm particles
Temperature: 40° C.
Flow: 1 mL/min
Solvent A: 5:95 acetonitrile:water with 10 mM ammonium acetate
Solvent B: 95:5 acetonitrile:water with 10 mM ammonium acetate LC/MS Methods Employed in Characterization of Examples Reverse phase analytical HPLC/MS was performed on Shimadzu LC 10AS systems coupled with Waters ZMD Mass Spectrometers (Methods A-E) or Waters Acquity system coupled with a Waters MICROMASS® ZQ Mass Spectrometer (Method F).

Method A: Linear gradient of 0 to 100% B over 4 min, with 1 min hold at 100% B
UV visualization at 220 nm
Column: PHENOMENEX® Luna C18 4.6×50 mm
Flow rate: 4 mL/min
Solvent A: 0.1% trifluoroacetic acid, 90% water, 10% acetonitrile
Solvent B: 0.1% trifluoroacetic acid, 90% acetonitrile, 10% water Method B: Linear gradient of 0 to 100% B over 4 min, with 1 min hold at 100% B
UV visualization at 220 nm
Column: PHENOMENEX® Luna C18 2×50 mm
Flow rate: 4 mL/min
Solvent A: 98% water, 2% methanol, 0.1% formic acid
Solvent B: Methanol, 0.1% formic acid Method C: Linear gradient of 0 to 100% B over 4 min, with 1 min hold at 100% B
UV visualization at 220 nm
Column: PHENOMENEX® Luna C18 4.6×50 mm
Flow rate: 4 mL/min
Solvent A: 0.1% trifluoroacetic acid, 90% water, 10% methanol
Solvent B: 0.1% trifluoroacetic acid, 90% methanol, 10% water Method D: Linear gradient of 0 to 100% B over 2 min, with 1 min hold at 100% B
UV visualization at 220 nm
Column: PHENOMENEX® Luna C18 2.0×30 mm
Flow rate: 1 mL/min
Solvent A: 0.1% trifluoroacetic acid, 90% water, 10% methanol
Solvent B: 0.1% trifluoroacetic acid, 90% methanol, 10% water Method E: Linear gradient of 0 to 100% B over 2 min, with 1 min hold at 100% B
UV visualization at 220 nm
Column: PHENOMENEX® Luna C18 2.0×30 mm
Flow rate: 1 mL/min
Solvent A: 98% water, 2% methanol, 0.1% formic acid
Solvent B: Methanol, 0.1% formic acid Method F: Linear gradient of 2 to 98% B over 1 min, with 0.5 min hold time at 98% B
UV visualization at 220 nm
Column: Waters BEH C18 2.1×50 mm
Flow rate: 0.8 mL/min
Solvent A: 0.05% TFA, 100% water
Solvent B: 0.05% TFA, 100% acetonitrile Preparative HPLC Methods Employed in the Purification of Products Method G: Linear gradient of 20 to 100% B over 10 min, with 2 min hold time at 100% B
Shimadzu LC-8A binary pumps
Shimadzu SPD-10A or 20A UV detector
UV visualization at 220 nm
Column: Waters SunFire 19×100 mm 5 µm C18
Flow rate: 20 mL/min
Solvent A: 0.1% TFA, 10% MeOH, 90% water
Solvent B: 0.1% TFA, 90% MeOH, 10% water Method J: Linear gradient of 20 to 100% B over 10 min, with 2 min hold time at 100% B
Shimadzu LC-8A binary pumps
Shimadzu SPD-10A or 20A UV detector
UV visualization at 220 nm
Column: PHENOMENEX® Luna Axia 30×100 mm 5 µm C18
Flow rate: 20 mL/min
Peak collection triggered by UV absorbance
Solvent A: 0.1% TFA, 10% MeOH, 90% water
Solvent B: 0.1% TFA, 90% MeOH, 10% water Method K: Linear gradient of 0 to 100% B over 10 min, with
2 min hold time at 100% B
Shimadzu LC-8A binary pumps
Shimadzu SPD-20A UV detector
UV visualization at 220 nm
Column: PHENOMENEX® Luna Axia 30×75 mm 5 µm C18
Flow rate: 20 mL/min
Peak collection triggered by UV absorbance
Solvent A: 0.1% TFA, 10% ACN, 90% water
Solvent B: 0.1% TFA, 90% ACN, 10% water NMR Employed in Characterization of Examples $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

IV. Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine ($Br^-$), iodine ($I^-$) and thiocyanate ($^-SCN$), only MPO is able to oxidize chloride ($Cl^-$) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J. Exp Med.*, 126:1063-1078 (1967); Klebanoff, S. J., *J. Bacteriol.*, 95:2131-2138 (1968); Klebanoff, S. J., *Science*, 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., *JCI*, 94:437-444 (1994); Bergt et al., *Proc. Natl. Acad. Sci.*, 101:13032-13037 (2004); Pennathur, S. et al., *JBC*, 279:42977-42983 (2004); Choi, D. K. et al., *J. Neurosci.*, 25(28):6394-6600 (2005)).

Eosinophil peroxidase (EPX) is a cationic heme-containing protein, and represents nearly 25% of the total mass of the secondary granule protein in eosinophils. It is a highly basic 77 kDa protein made up of two subunits containing a modified Fe-protoporphyrin-IX prosthetic group. EPX shares with MPO the ability to use $H_2O_2$ to oxidize thiocyanate, bromide, and nitrite in vivo to kill bacteria, and viruses (Jong, E. C. et al., *J. Immunol.*, 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay (Amplex Red Assay)

MPO peroxidation activity was measured in 100 mM KPi (pH 7.4) by utilizing the non-fluorescent reagent Amplex Red (Invitrogen Cat. #A12222) which can be oxidized to the highly fluorescent resorufin. Amplex Red is oxidized by the peroxidase action of MPO to resorufin. Reactions were carried out in 50 µL total volume by adding a 25 µL mixture of 200 µM myeloperoxidase and 40 nM $H_2O_2$ (Sigma #349887) to 100 nL inhibitor in 100% DMSO in a 384 well Perkin Elmer Optiplate. Enzyme and compound were preincubated for ten minutes at room temperature.

After the ten minute preincubation, 25 µL of an Amplex Red mixture containing 200 µM Amplex Red and 10 mM $H_2O_2$ was added to the plate. Kinetic determinations were carried out immediately on a Perkin Elmer Envision (15 minute kinetic read, Ex: 535 nm, Em: 590 nm).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B-A}{1+(C/x)^D}$$

where A=minimal Y value (activity level of inhibited sample), B=maximal Y value (activity level of uninhibited sample), C=Log $IC_{50}$, D=Hill Slope, x=concentration of inhibitor.

MPO Chlorination Assay (APF Assay)

MPO chlorination activity was measured in 100 mM KPi (pH 7.4) by utilizing the non-fluorescent reagent Aminophenyl fluorescein (APF, Invitrogen Cat. #A36003). APF is cleaved by (—OCl) to yield the fluorescent compound fluorescein. Reactions were carried out in 50 µL total volume by adding a 25 µL mixture of 200 µM myeloperoxidase and 120 mM NaCl to 100 nL inhibitor in 100% DMSO in a 384 well, non-binding surface clear bottom plate (Corning #3655). Enzyme, inhibitor, and chloride were preincubated for ten minutes at room temperature.

After the ten minute preincubation, 25 µL of an APF mixture containing 10 mM APF, 120 mM NaCl and 10 µM $H_2O_2$ was added to the plate using the internal dispensing system of a Hammatsu FDSS 6000. Kinetic determinations were carried out immediately on the FDSS 6000 (3 minute kinetic read, 1 read every second, Ex: 485 nm, Em: 535 nm). $IC_{50}$ values for inhibitors were calculated by taking the slope of the linear portion of the kinetic measurement (20 seconds to ~80-120 secs).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

EPX Bromination Assay

EPX bromination activity was measured in 100 mM KPi (pH 7.4) by monitoring the $H_2O_2$ catalyzed formation of 3-bromo tyrosine from tyrosine and potassium bromide. A 50 µl mixture of 0.6 µM EPX (Lee Biosolutions Cat. #342-60) was added to 100 nL inhibitor in 100% DMSO in a 384 well REMP plate. Enzyme and compound were preincubated for ten minutes at room temperature.

After the ten minute preincubation of enzyme and inhibitor, 25 µL of a mixture containing 400 µM tyrosine and 1200 µM potassium bromide was added to the plate containing enzyme and inhibitor, followed by the addition of 25 µl of 20 µM $H_2O_2$. The reaction was allowed to proceed for 15 minutes, at which time it was quenched with 10 µL of 20% TCA. The final concentrations of all components were 0.3 µM EPX, 100 µM tyrosine, 400 µM potassium bromide, 5 µM $H_2O_2$, 0.1% DMSO, 2.0% TCA.

$IC_{50}$ values were determined by determining the peak areas of 3-bromo-tyrosine present at the end of the 15 minute reaction and fitting the data to:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

Reversed-phase analysis was performed on a Waters Acquity Ultra Performance LC system using an Acquity UPLC BEH $C_{18}$ 1.7 µM, 2.1×50 mm analytical column. The column was maintained at 60° C. Samples were eluted using a gradient of 0%-100% B over 2.5 minutes, followed by equilibration with 100% A for 1 minute where A consisted of 0.1% TFA and B consisted of 90% MeOH/0.1% TFA at a flow rate of 0.6 mL/min. The retention time of 3-bromo tyrosine was 1.22 min.

The exemplified Examples disclosed below were tested in the MPO peroxidation assay described above and found having MPO inhibitory activity. A range of $IC_{50}$ values of ≤3 µM (3000 nM) was observed.

Some of the exemplified Examples disclosed below were tested in the MPO chlorination assay described above and found having MPO inhibitory activity. A range of $IC_{50}$ values of ≤3 µM 30000 nM) was observed.

Some compounds of the invention were tested in the EPX bromination assay described above and were found to inhibit EPX with a range of $IC_{50}$ values of ≤3 µM (3000 nM), as demonstrated by Example 6 (EPX $IC_{50}$=0.07 µM), Example 11 (EPX $IC_{50}$=0.04 µM), Example 15 (EPX $IC_{50}$=0.04 µM) and Example 55 (EPX $IC_{50}$=0.01 µM).

Table 1 below lists $IC_{50}$ values in the MPO peroxidation (Amplex Red) assay and/or MPO chlorination assay (APF) measured for the following examples.

TABLE 1

| Example No. | Amplex Red Assay $IC_{50}$ value (µM) | APF Assay $IC_{50}$ value (µM) |
|---|---|---|
| 6 | 0.02 | 0.13 |
| 11 | 0.02 | 0.17 |
| 12 | 0.02 | 0.08 |
| 13 | 0.03 | 0.10 |
| 14 | 0.12 | 0.12 |
| 15 | 0.02 | 0.06 |
| 28 | 2.40 | 1.19 |
| 32 | 0.61 | 0.32 |
| 34 | 1.39 | 0.79 |
| 43 | 0.76 | 1.52 |
| 46 | 0.09 | 0.47 |
| 53 | 0.08 | 0.10 |
| 55 | 0.01 | 0.08 |
| 57 | 0.08 | 0.32 |
| 61 | 0.09 | 0.91 |
| 85 | 1.08 | 0.64 |
| 86 | 2.03 | 1.10 |
| 90 | 0.11 | 0.05 |

The following Examples were tested in the MPO peroxidation assay described above and found having MPO inhibitory activity with $IC_{50}$ values of ≤0.06 µM (60 nM): 1, 2, 3, 7, 8, 9, 10, 16, 17, 18, 19, 20, 21, 39, 45, 49, 65, 66, 67, 72, 73, 78, 81, 82, 87, 89, 93, 95, 96, 97, 98, 99, 101, 104, 105, 107, and 110.

The following Examples were tested in the MPO peroxidation assay described above and found having MPO inhibitory activity in the range of $IC_{50}$ values between 0.06 µM (60 nM) and 0.15 µM (150 nM): 4, 5, 24, 25, 29, 30, 38, 42, 51, 54, 56, 63, 64, 68, 71, 84, 88, 91, 92, 103, 108, 111, 112, 113, 114, 115, 116, 118, 119, 121, 122, and 124.

The following Examples were tested in the MPO peroxidation assay described above and found having MPO inhibitory activity in the range of $IC_{50}$ values between 0.15 µM (150 nM) and 1.0 µM (1000 nM): 26, 27, 31, 36, 37, 38, 40, 55, 58, 67, 69, 71, 120, 124, 127, 129, 131, 140, 143, 146, 147, 152, 157, 158, 159, 160, 161, 162, 163, and 165.

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

As used herein, the term "patient" encompasses all mammalian species.

As used herein, the term "subject" refers to any human or non-human organism that could potentially benefit from treatment with a MPO inhibitor. Exemplary subjects include human beings of any age with risk factors for cardiovascular disease. Common risk factors include, but are not limited to, age, sex, weight, family history, or signs of insulin resistance such as acanthosis nigricans, hypertension, dyslipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit MPO and/or to prevent or treat the disorders listed herein. When applied to a combination, the term refers to combined amounts of the active ingredients that result in the preventive or therapeutic effect, whether administered in combination, serially, or simultaneously.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following examples demonstrate a partial scope of the invention and are not meant to be limiting of the scope of the invention.

General Synthesis Procedures:

General Scheme 1:

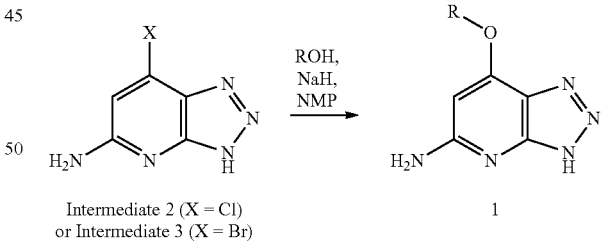

Intermediate 2 (X = Cl)
or Intermediate 3 (X = Br)

Compounds of the invention can be prepared by treating Intermediate 2 or 3 with an appropriately substituted alcohol and an appropriate base such as NaH in NMP or another solvent known to one skilled in the art with heat. For example, NaH (2.0-4.0 eq, 60% dispersion in oil) was added to a mixture of ROH (1.5-4.0 eq), 7-bromo-3H-[1,2,3]triazolo[4,5-b]pyridin-5-amine (Intermediate 3) or 7-chloro-3H-[1,2,3]triazolo[4,5-b]pyridin-5-amine (Intermediate 2, 1.0 eq) in NMP (0.10-0.50 M) and stirred at 100-130° C. for 1-3 days. The reaction was quenched with aqueous ammonium acetate, partially concentrated and purified by prep HPLC to yield the desired product 1.

General Scheme 2:

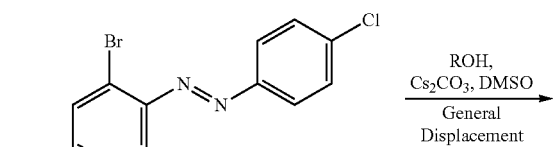

Intermediate 1

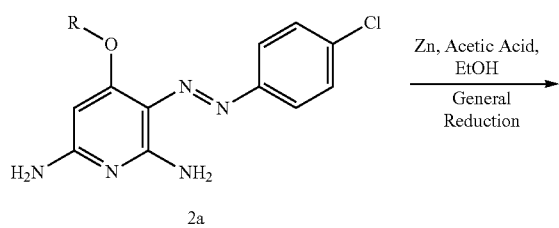

2a

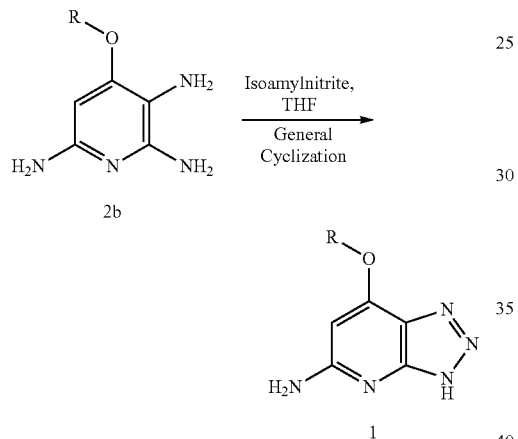

Alternatively compounds of the invention (1) can be prepared by reacting Intermediate 1 with an appropriately substituted alcohol (ROH) and a base such as $Cs_2CO_3$ in an appropriate solvent such as DMSO to afford ether 2a. Treatment with Zn and acetic acid in EtOH affords to diamine 2b. Cyclization with isoamylnitrite in THF affords compounds of the invention (1).

General Displacement

A mixture of (E)-4-bromo-3-((4-chlorophenyl)diazenyl)pyridine-2,6-diamine (Intermediate 1, 1.0 eq), ROH (1.0-3.0 eq) and an appropriate base such as $Cs_2CO_3$ (2.0 eq) in DMSO (0.10-0.30 M) was heated for 2 days at 70-110° C. The reaction mixture was diluted with water/brine and extracted with EtOAc. The combined organics were washed with brine, dried over $Na_2SO_4$ and concentrated in vacuo. The crude mixture was purified by column chromatography to yield the ether 2a.

General Reduction

A mixture of the diazo compound 2a (1.0 eq) and zinc (3.0-5.0 eq) in EtOH (0.10-0.20 M) and acetic acid (5.0-10 eq) was stirred at 40-70° C. for 15 min-5 h. The mixture was filtered and concentrated. The crude material was optionally redissolved in 7.0 M $NH_3$ (0.50 M) in MeOH and concentrated. The crude product was purified by column chromatography to yield the desired product 2b.

General Cyclization

Isoamyl nitrite (0.90-3.0 eq) was added to a mixture of the triamine 2b (1.0 eq) in THF (0.10 M) and acetic acid (0-10 eq), and the mixture was stirred at rt for 2 h-64 h. The reaction mixture was concentrated and purified by prep HPLC to yield the desired product 1.

General Scheme 3:

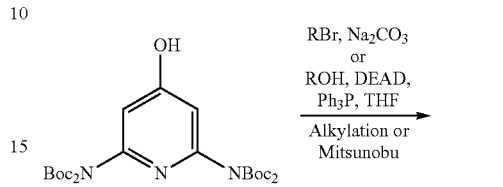

Intermediate 4

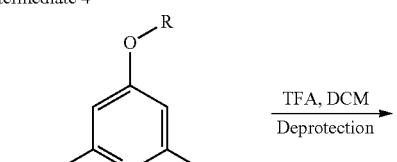

3a

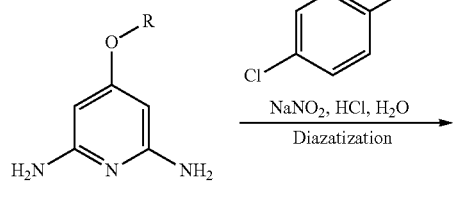

3b

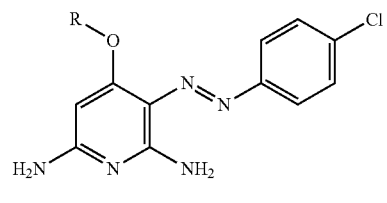

2a

Alternatively compounds of the invention (1) can be prepared by reacting Intermediate 4 with an appropriately substituted alkyl bromide (RBr) and a base such as $Na_2CO_3$ in an appropriate solvent such as DMSO or with an appropriately substituted alcohol (ROH) and DEAD and $PPh_3$ in an appropriate solvent such as THF to afford ether 3a. Deprotect of 3a with an acid such as TFA affords diamine 3b. Diazotization with of 3b with a diazonium salt derived from an aniline such as p-chloroaniline produces 3c. Intermediate 3c can be converted to compounds of the invention using procedures described in General Scheme 2.

General Alkylation

An alkyl bromide (1.0-1.5 eq) was added to a mixture of Intermediate 4 (1.0 eq), $Na_2CO_3$ or $K_2CO_3$ (2 eq) and TBABr (0.0-2.0 eq) in DMSO (0.10-0.30 M) and stirred 4-16 h. The mixture was diluted with EtOAc, washed with water and/or brine, dried over $Na_2SO_4$ and concentrated. The crude product was purified by flash chromatography to yield the compound 3a.

General Mitsunobu Procedure

DEAD or DIAD (2.0 eq) was added to a mixture of Intermediate 4 (1.0 eq), ROH (1.5 eq) and triphenylphosphine (2.0 eq) in THF (0.20 M) and stirred at rt 4-24 h. The reaction mixture was concentrated and the crude product was purified by flash chromatography to yield compound 3a.

General Boc Deprotection

TFA (equal volume to DCM) was added to a solution of the pyridine ether 3a in DCM (0.10-0.50 M) and stirred at rt for 1-8 h. The mixture was concentrated and crude 3b was used in the next reaction without purification.

General Diazotization

A solution of 6.0 N HCl (3.5 eq) was added to 4-chloroaniline (1.2 eq) with vigorous stirring at 0° C. A solution of sodium nitrite (1.0 eq) in water (1.0 M) was added to the flask. After stirring for 30 min, urea (0.10 eq) was added to destroy excess $NaNO_2$.

The above solution was added to a suspension of diaminopyridine 3b (1.0 eq) in water, EtOAc and MeOH (0.10 M, 5:2:1 ratio). After 30 min, sodium acetate (4.0 eq) was added and the mixture was stirred overnight. The mixture was partially concentrated and partitioned between EtOAc and $NaHCO_3$. The combined organics were washed with brine, dried over $Na_2SO_4$ and concentrated in vacuo to yield a solid that was carried into the next step without purification. The resulting product 2a can be converted into the desired triazolopyridine 1 using the chemistry described in General Scheme 2.

General Scheme 4:

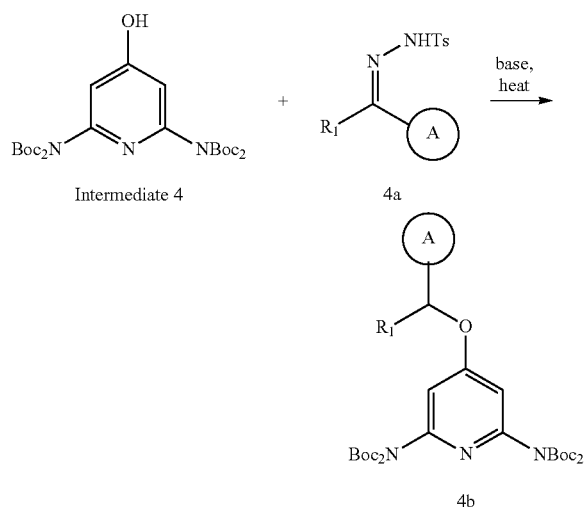

Alternatively compounds of the invention (1) can be prepared by reacting Intermediate 4 with tosylhydrazone with $K_2CO_3$ in an appropriate solvent such as dioxane to yield ether 4b. Intermediate 4b can be converted to compounds of the invention using procedures described in General Schemes 2 and 3.

A mixture of Intermediate 4 (1.0 eq), a tosylhydrazone (1.0 eq), and potassium carbonate (3.0-5.0 eq) in dioxane was stirred at 110° C. The reaction mixture was cooled to rt, diluted with EtOAc and filtered. Upon concentration in vacuo, the reaction mixture was purified by flash column chromatography to yield the ether 4a, which can be converted into the desired triazolopyridine 1 using the chemistry described in General Routes 2 and 3.

General Scheme 5:

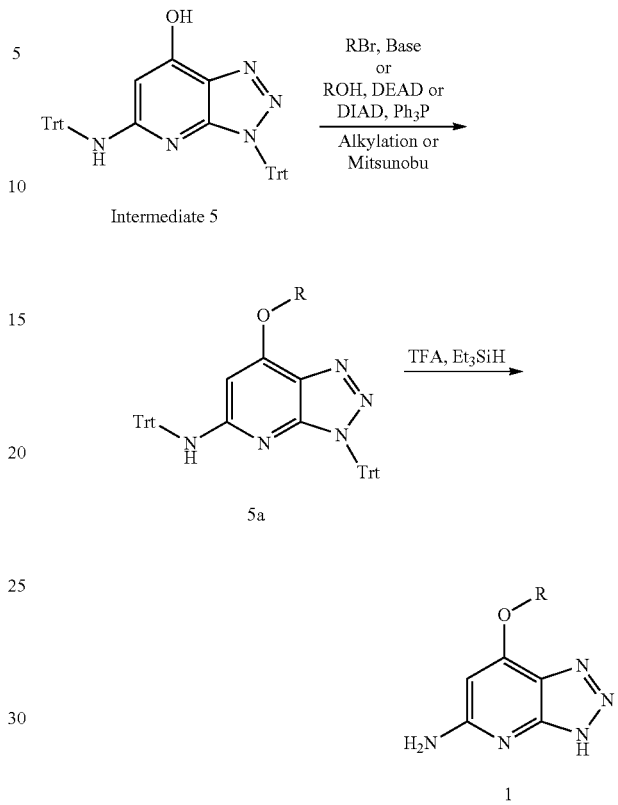

Alternatively compounds of the invention (1) can be prepared by reacting Intermediate 5 with an appropriately substituted alkyl bromide (RBr) and a base such as $Na_2CO_3$ in an appropriate solvent such as DMSO or with an appropriately substituted alcohol (ROH) and DEAD and $PPh_3$ in an appropriate solvent such as THF to afford ether 5a. Deprotection of 5a with an acid such as TFA in the presence of triethylsilane affords compounds of the invention.

General Alkylation

An alkyl bromide (1.0-1.5 eq) was added to a mixture of Intermediate 5 (1.0-2.0 eq), $Na_2CO_3$ or $K_2CO_3$ (2 eq) in DMSO (0.10-0.30 M), and the mixture was stirred 4-16 h. The mixture was diluted with EtOAc, washed with water and/or brine, dried over $Na_2SO_4$ or $MgSO_4$ and concentrated. Crude 5a was carried on to the General Trityl Deprotection.

General Mitsunobu Procedure

DEAD or DIAD (2.0 eq) was added to a mixture of Intermediate 4 (1.0 eq), ROH (1-2 eq) and triphenylphosphine (2.0 eq) in THF (0.05-0.50 M), and the mixture was stirred at rt 4-24 h. The reaction mixture was concentrated. Crude 5a was carried on to the General Trityl Deprotection.

General Trityl Deprotection

TFA was added to a solution of the pyridine ether 5a in DCM or THF (0.10-0.50 M) and stirred at rt for 1-8 h. Triethylsilane (2-10 eq) was added and the mixture was concentrated in vacuo. The crude material was purified by preparatory HPLC to obtain triazolopyridine compounds of the invention.

General Scheme 6:

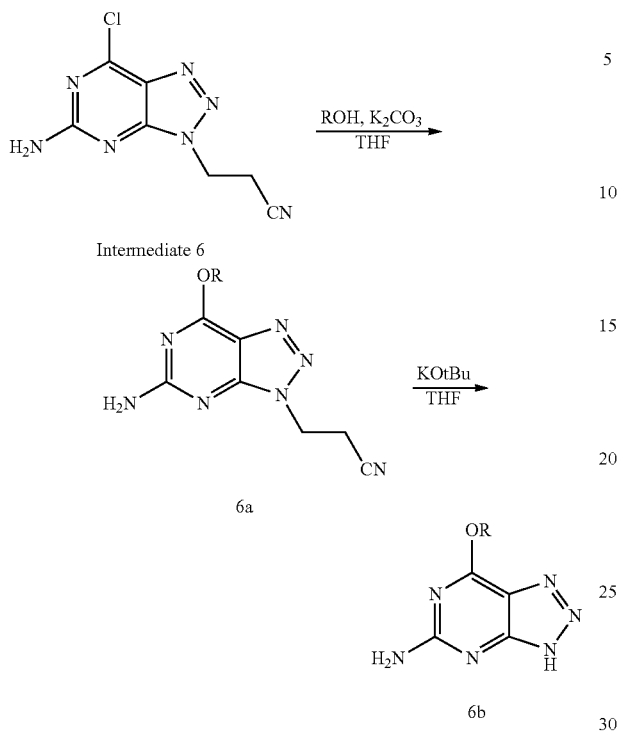

General Displacement

To a solution of Intermediate 6 (1.0 eq), ROH (1.5 eq) in DME (0.2 M) was added $K_2CO_3$ (3 eq). The reaction mixture was heated to 80° C. overnight. The solution was filtered and concentrated and the residue purified by silica gel chromatography to furnish the desired ether 6a.

Ethylcyano Deprotection

To a solution of the 3-(alkoxy)-3H-[1,2,3]triazolo[4,5-d]pyrimidin-3-yl)propanenitrile 6a in THF (0.1 M) at 0° C. was added KOtBu (1 eq). After 10-60 min, the reaction was quenched with AcOH (2 eq.), then concentrated. The residue was purified by preparative HPLC to furnish the desired product 6b.

Common Intermediates:

Intermediate 1: (E)-4-Bromo-3-((4-chlorophenyl)diazenyl)pyridine-2,6-diamine

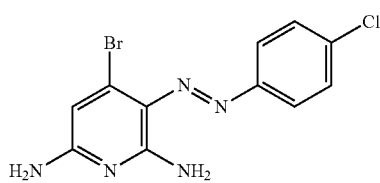 [SMILES: Nc1cc(Br)c(/N=N/c2ccc(Cl)cc2)c(N)n1]

A solution of HCl (34 mL, 200 mmol) was added to 4-chloroaniline (7.5 g, 59 mmol) with vigorous stirring at 0° C. A solution of sodium nitrite (3.7 g, 53 mmol) in water (20 mL) was added to the flask. After stirring for 30 min, urea (0.32 g, 5.3 mmol) was added to destroy excess $NaNO_2$. The above solution was poured into a heterogeneous mixture of 4-bromopyridine-2,6-diamine (10 g, 53 mmol) in water (300 mL) and was stirred for 1.5 h. Sodium acetate (15 g, 190 mmol) in 300 mL of water was added and the mixture was stirred overnight. The precipitate was collected by filtration and washed thoroughly with water (5×) and dried in vacuo. The remaining water was removed by azeotroping the solid with DCM/Acn to provide Intermediate 1 (17 g, 53 mmol, 99% yield) as a yellow solid. $^1$H NMR (500 MHz, DMSO-$d_6$) δ 9.65 (br. s., 1H), 7.78-7.70 (m, 2H), 7.65 (br. s., 1H), 7.56-7.47 (m, 2H), 7.04 (br. s., 2H), 6.43 (s, 1H).

Intermediate 2: 7-Chloro-3H-[1,2,3]triazolo[4,5-b]pyridin-5-amine

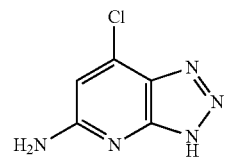 [SMILES: Nc1cc(Cl)c2nn[nH]c2n1]

Intermediate 2A: (E)-4-Chloro-3-((4-chlorophenyl)diazenyl)pyridine-2,6-diamine

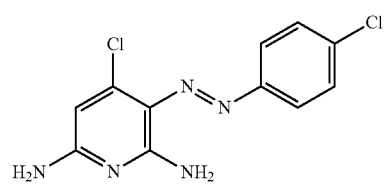 [SMILES: Nc1cc(Cl)c(/N=N/c2ccc(Cl)cc2)c(N)n1]

Intermediate 2A was synthesized using procedure similar to the Intermediate 1 synthesis procedure starting from 4-chloropyridine-2,6-diamine. MS (ESI) m/z 282.0 (M+H).

Intermediate 2B: 4-Chloropyridine-2,3,6-triamine

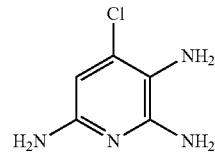

A mixture of (E)-4-chloro-3-((4-chlorophenyl)diazenyl)pyridine-2,6-diamine (7.0 g, 25 mmol) and zinc (4.9 g, 74 mmol) in EtOH (120 mL)/acetic acid (7.1 mL) was stirred at 70° C. for 2 h. The mixture was filtered and concentrated. The crude product was purified by column chromatography (2.0 M $NH_3$ in MeOH/DCM, 0-20% gradient) to yield Intermediate 2B (2.3 g, 14 mmol, 57% yield) as a brown solid.

Intermediate 2

Isoamyl nitrite (1.1 mL, 8.0 mmol) was added to a mixture of 4-chloropyridine-2,3,6-triamine (1.4 g, 8.8 mmol) in THF (50 mL) and acetic acid (2.5 mL), and the mixture was stirred at rt overnight. The reaction mixture was concentrated and purified by column chromatography (0% to 20% gradient, MeOH/DCM with 0.5% AcOH) to yield Intermediate 2 (600 mg, 3.5 mmol, 40% yield) as a brown solid. MS (ESI) m/z 170.1 (M+H).

Intermediate 3: 7-Bromo-3H-[1,2,3]triazolo[4,5-b]pyridin-5-amine

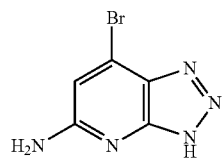

Intermediate 3 was synthesized from Intermediate 1 using the procedures described in the synthesis of Intermediate 2. MS (ESI) m/z 213.9/215.9 (M+H). $^1$H NMR (500 MHz, CD$_3$OD) δ 6.82 (s, 1H).

Intermediate 4: 2-[6-[Bis[(1,1-dimethylethoxy)carbonyl]amino]-1,4-dihydro-4-oxo-2-pyridinyl]-1,3-bis(1,1-dimethylethyl) ester

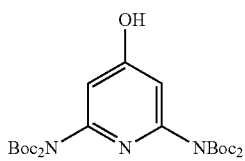

Intermediate 4A: 4-(Benzyloxy)pyridine-2,6-diamine

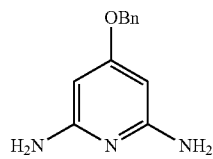

4-Benzyloxy-2,6-pyridine was synthesized from chelidamic acid as described in the literature (*Chem. Eur. J.*, 7(9):1889-1898 (2001)).

Intermediate 4B: Di-tert-butyl(4-(benzyloxy)pyridine-2,6-diyl)bis(tert-butoxycarbonylcarbamate)

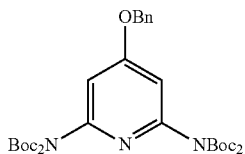

Boc$_2$O (13 mL, 56 mmol) and DMAP (0.55 g, 4.5 mmol) were added as solids to a solution of 4-(benzyloxy)pyridine-2,6-diamine (2.4 g, 11 mmol) in Acn (50 mL)/DCM (25 mL), and the mixture was stirred overnight at rt. An additional of 5.0 eq Boc$_2$O and 0.25 eq DMAP were added and the mixture was stirred overnight. The reaction was concentrated in vacuo. The crude product was purified by flash chromatography (loading in 10:1 Hexanes/EtOAc, 0% to 50% EtOAc in hexane over 30 min using a 120 g silica gel cartridge) to yield Intermediate 4B (5.7 g, 9.3 mmol, 83% yield) as a white solid. $^1$H NMR (500 MHz, CD$_3$OD-d$_4$) δ 7.47-7.44 (m, 2H), 7.41-7.36 (m, 2H), 7.35-7.30 (m, 1H), 6.96 (s, 2H), 5.26 (s, 2H), 1.42 (s, 36H).

Intermediate 4

A mixture of Intermediate 4B (5.7 g, 9.3 mmol) and Pd/C (500 mg, 0.47 mmol) in MeOH (100 mL) was stirred under H$_2$ (1.0 atm) overnight. The mixture was filtered and concentrated to yield Intermediate 4 (4.7 g, 8.9 mmol, 97% yield) as a clear foam. MS (ESI) m/z 526.2 (M+H).

Intermediate 5: 3-Trityl-5-(tritylamino)-3H-[1,2,3]triazolo[4,5-b]pyridin-7-ol

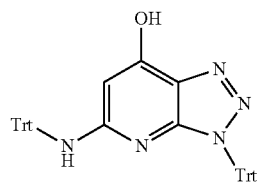

Intermediate 5A: (E)-4-(Benzyloxy)-3-((4-chlorophenyl)diazenyl)pyridine-2,6-diamine

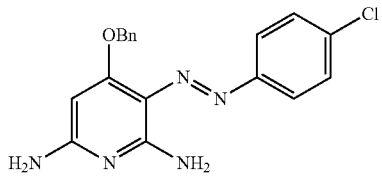 [SMILES: Nc1cc(OCc2ccccc2)c(/N=N/c2ccc(Cl)cc2)c(N)n1]

A solution of sodium nitrite (3.0 g, 44 mmol) in water (2 mL) was added to a slurry of 4-chloroaniline (5.6 g, 44 mmol) in 6 M HCl (15 mL, 88 mmol), and the reaction mixture was allowed to stir at rt for 30 minutes. The solution was added to a suspension of 4-(benzyloxy)pyridine-2,6-diamine (Intermediate 4a) (9.5 g, 44 mmol) in MeOH (440 mL). The resultant slurry was stirred at rt for 18 hrs. The reaction mixture was filtered to isolate (E)-4-(benzyloxy)-3-((4-chlorophenyl)diazenyl)pyridine-2,6-diamine (13 g, 37 mmol, 84% yield) as an orange solid. MS (ESI) m/z 354.1 (M+H).

Intermediate 5B: 4-(Benzyloxy)pyridine-2,3,6-triamine

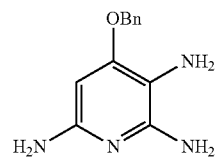 [SMILES: Nc1cc(OCc2ccccc2)c(N)c(N)n1]

Zinc (4.5 g, 69 mmol) was added portionwise to a solution of (E)-4-(benzyloxy)-3-((4-chlorophenyl)diazenyl)pyridine-2,6-diamine (12 g, 35 mmol) and acetic acid (7.9 mL) at 60° C. The reaction mixture was stirred until the color had disappeared, and TLC/LCMS analysis indicated starting material consumption. The reaction mixture was filtered through CELITE®, concentrated, and purified by column chromatography (eluting with a linear gradient of 0% to 40% MeOH in DCM over 28 minutes). Intermediate 5B (5.7 g, 25 mmol, 71% yield) was isolated as a brown solid. MS (ESI) m/z 231.1 (M+H).

Intermediate 5C: 7-(Benzyloxy)-3H-[1,2,3]triazolo[4,5-b]pyridin-5-amine

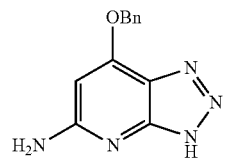

Isoamyl nitrite (2.8 mL, 21 mmol) was added to a solution of Intermediate 5B (4.7 g, 21 mmol) and acetic acid (5.9 mL) in THF (100 ml), and the solution was stirred for 1.5 hrs at rt. The reaction mixture was partially concentrated and then diluted with hexane to precipitate product. The solid was filtered and dried in vacuo to yield Intermediate 5C (4.1 g, 17 mmol, 83% yield) as a brown powder. MS (ESI) m/z 242.2 (M+H).

Intermediate 5D: 7-(Benzyloxy)-N,3-ditrityl-3H-[1,2,3]triazolo[4,5-b]pyridin-5-amine

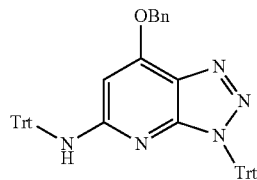

Triethylamine (3.6 mL, 26 mmol) was added to a suspension of Intermediate 5C (1.3 g, 5.2 mmol) and (chloromethanetriyl)tribenzene (2.9 g, 10 mmol) in DCM (52 mL), and the reaction mixture was stirred at rt for 18 hrs. The reaction mixture was concentrated and purified by column chromatography (EtOAc/hex) to yield Intermediate 5D (3.6 g, 5.0 mmol, 96% yield) as a tan solid.

Intermediate 5

Triethylsilane (0.90 mL, 5.6 mmol) and triethylamine (0.63 mL, 4.5 mmol) were added to a solution of palladium (II) acetate (0.042 g, 0.19 mmol) in DCM (5 mL), and the reaction mixture was stirred for 10 minutes. A solution of Intermediate 5D (2.7 g, 3.8 mmol) in DCM (7 mL) was added and stirring was continued overnight. MeOH (10 mL) was added, and the reaction mixture was stirred at rt for 2 h. The reaction mixture was concentrated in vacuo, diluted with EtOAc and washed with saturated aqueous ammonium chloride solution. The combined organics were dried over sodium sulfate and concentrated in vacuo. Intermediate 5 (2.3 g, 3.4 mmol, 89% yield) was isolated as a grayish solid. MS (ESI) m/z 636.2 (M+H). Intermediate 5 and compounds synthesized using Intermediate 5 as a starting material exist as a mixture of trityl isomers, but only one isomer is illustrated in this patent for these compounds.

Intermediate 6: 3-(5-Amino-7-chloro-3H-[1,2,3]triazolo[4,5-d]pyrimidin-3-yl)propanenitrile

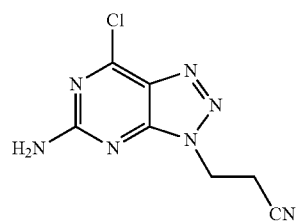 [SMILES: N#CCCn1nnc2c(Cl)nc(N)nc21]

Intermediate 6A: 3-((2,5-Diamino-6-chloropyrimidin-4-yl)amino)propanenitrile

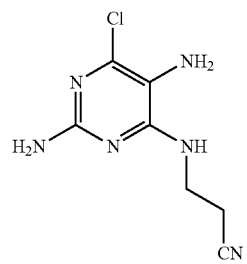 [SMILES: N#CCCNc1nc(N)nc(Cl)c1N]

Intermediate 6A was prepared according to U.S. Pat. No. 4,543,255. A mixture of 4,6-dichloropyrimidine-2,5-diamine[1] (2.0 g, 11 mmol) and 3-aminopropionitrile (4.1 mL, 56 mmol) was heated to 100° C. and stirred 1 h. The material was cooled to rt, concentrated to yield Intermediate 6A (2.4 g, 11 mmol, 100% yield) which was used in the subsequent step without purification. MS (ESI) m/z 213 (M+H).

Intermediate 6

To a solution of Intermediate 6A (2.4 g, 11 mmol) in AcOH (9.3 mL)/water (28 mL) was added NaNO$_2$ (0.93 g, 13 mmol) in water (19 mL) at 0° C. After 10 min, the reaction mixture was diluted with EtOAc and adjusted to pH=6 using sat. aq. NaHCO$_3$. The organic layer was washed with brine, dried over MgSO$_4$, filtered and concentrated. The residue was purified by filtration through a silica plug with EtOAc as the eluent and the resulting solution was concentrated to furnish Intermediate 6 (1.1 g, 5.0 mmol, 44% yield). MS (ESI) m/z 224.4 (M+H). $^1$H NMR (400 MHz, DMSO-d$_6$) δ 7.76 (br. s., 2H), 4.67 (t, J=6.3 Hz, 2H), 3.22 (t, J=6.3 Hz, 2H).

Example 1: 7-(Benzo[d][1,3]dioxol-5-ylmethoxy)-3H-[1,2,3]triazolo[4,5-b]pyridin-5-amine

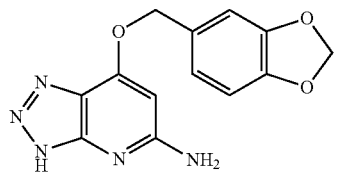 [SMILES: Nc1cc(OCc2ccc3c(c2)OCO3)c2nn[nH]c2n1]

NaH (56.6 mg, 1.415 mmol) was added to a mixture of benzo[d][1,3]dioxol-5-ylmethanol (110 mg, 0.71 mmol), and Intermediate 2 (20 mg, 0.093 mmol) in NMP (2 mL), and the mixture was stirred at 130° C. for 3 days. The reaction was quenched with aqueous ammonium acetate. The mixture was partially concentrated and purified by prep HPLC to yield Example 1 (6.0 mg, 0.019 mmol, 4.0% yield) as a white solid. MS (ESI) m/z 286.1 (M+H). $^1$H NMR (500 MHz, CD$_3$OD) δ 7.06-6.98 (m, 2H), 6.91-6.83 (m, 1H), 6.33 (s, 1H), 5.98 (s, 2H), 5.36 (s, 2H). Analytical HPLC Col A: 4.84 min, 90%; Col B: 4.84 min, 93%.

Example 2: 7-((2,3-Dihydrobenzo[b][1,4]dioxin-5-yl)methoxy)-3H-[1,2,3]triazolo[4,5-b]pyridin-5-amine

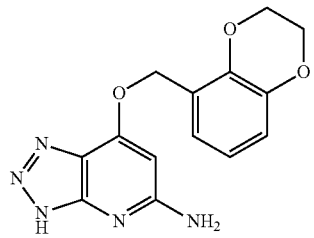 [SMILES: Nc1cc(OCc2cccc3c2OCCO3)c2nn[nH]c2n1]

Example 2A: (E)-3-((4-Chlorophenyl)diazenyl)-4-((2,3-dihydrobenzo[b][1,4]dioxin-5-yl)methoxy)pyridine-2,6-diamine

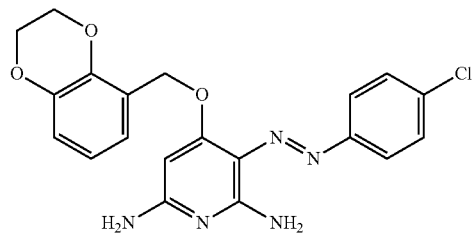 [SMILES: Nc1cc(OCc2cccc3c2OCCO3)c(/N=N/c2ccc(Cl)cc2)c(N)n1]

A mixture of Intermediate 1 (500 mg, 1.5 mmol), (2,3-dihydrobenzo[b][1,4]dioxin-5-yl)methanol (380 mg, 2.3 mmol) and Cs$_2$CO$_3$ (1000 mg, 3.1 mmol) in DMSO (5 mL) was stirred for 2 days at 120° C. The reaction mixture was diluted with water and brine (1:1, 50 mL) and extracted with EtOAc (2×30 mL). The combined organics were washed with brine, dried over Na$_2$SO$_4$ and concentrated in vacuo. The crude product was purified by column chromatography to yield the Example 2A (400 mg, 0.97 mmol, 63% yield), as a brown oil. MS (ESI) m/z 412.2 (M+H).

Example 2

A mixture of Example 2A (400 mg, 0.971 mmol) and zinc (190 mg, 2.9 mmol) in EtOH (5 mL)/acetic acid (0.28 mL) was stirred at 70° C. for 2 h. The mixture was filtered and concentrated. The crude was redissolved in ammonia in MeOH (7 M, 4 mL) and concentrated. The crude product was purified by column chromatography (2 M NH$_3$ in MeOH/CH$_2$Cl$_2$ 0-20%) to yield the intermediate triamine (82 mg, 0.28 mmol, 29% yield) as a black solid. Isoamyl nitrite (0.034 mL, 0.26 mmol) was added to a mixture of the triamine in THF (3 mL) and acetic acid (0.08 mL) and stirred at rt overnight. The reaction mixture was purified by prep HPLC to yield Example 2 (15 mg, 0.045 mmol, 16% yield) as a brown solid. MS (ESI) m/z 300.2 (M+H). $^1$H NMR (500 MHz, CD$_3$OD) δ 7.03 (dd, J=7.2, 1.9 Hz, 1H), 6.94-6.84 (m, 2H), 6.43 (s, 1H), 5.46 (s, 2H), 4.34-4.30 (m, 2H), 4.30-4.26 (m, 2H).

Example 3: 7-((2,2-Difluorobenzo[d][1,3]dioxol-4-yl)methoxy)-3H-[1,2,3]triazolo[4,5-b]pyridin-5-amine

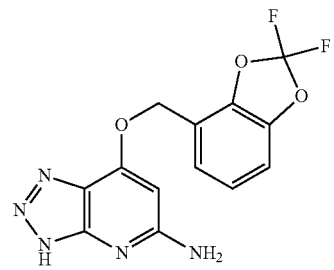 [SMILES: Nc1cc(OCc2cccc3c2OC(F)(F)O3)c2nn[nH]c2n1]

Example 3 was synthesized from (2,2-difluorobenzo[d][1,3]dioxol-4-yl)methanol and Intermediate 1 using General Route 2. MS (ESI) m/z 322.0 (M+H). $^1$H NMR (500 MHz, CD$_3$OD) δ 7.37 (dd, J=7.3, 1.8 Hz, 1H), 7.30-7.20 (m, 2H), 6.40 (s, 1H), 5.58 (s, 2H). Analytical HPLC Col A: 5.31 min, 93%; Col B: 5.83 min, 93%.

Example 4: 7-((1-Phenyl-1H-1,2,3-triazol-4-yl)methoxy)-3H-[1,2,3]triazolo[4,5-b]pyridin-5-amine

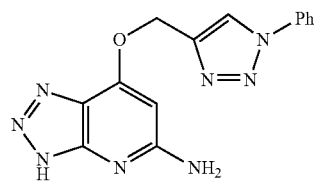 [SMILES: Nc1cc(OCc2cn(-c3ccccc3)nn2)c2nn[nH]c2n1]

Example 4 was synthesized from (1-phenyl-1H-1,2,3-triazol-4-yl)methanol and Intermediate 1 using General Route 2. MS (ESI) m/z 309.3 (M+H). $^1$H NMR (500 MHz, CD$_3$OD) δ 8.78 (s, 1H), 7.91-7.84 (m, 2H), 7.65-7.57 (m, 2H), 7.56-7.50 (m, 1H), 6.55 (s, 1H), 5.70 (s, 2H). Analytical HPLC Col A: 4.69 min, 92%; Col B: 5.45 min, 94%.

Example 5: 7-((6-(3-Fluorophenyl)pyridin-2-yl)methoxy)-3H-[1,2,3]triazolo[4,5-b]pyridin-5-amine

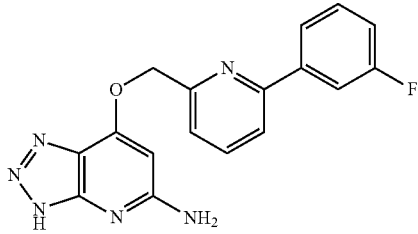 [SMILES: Nc1cc(OCc2cccc(-c3cccc(F)c3)n2)c2nn[nH]c2n1]

Example 5A: (6-(3-Fluorophenyl)pyridin-2-yl)methanol

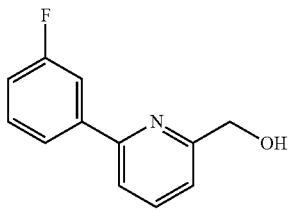 [SMILES: OCc1cccc(-c2cccc(F)c2)n1]

A mixture of (6-bromopyridin-2-yl)methanol (1.0 g, 5.3 mmol), (3-fluorophenyl)boronic acid (0.82 g, 5.9 mmol), PdCl$_2$(dppf)-CH$_2$Cl$_2$ Adduct (0.43 g, 0.53 mmol) and Na$_2$CO$_3$ (0.56 g, 5.3 mmol) in dioxane (15 mL) and water (1.5 mL) in a microwave vial was purged with argon for 20 min then subjected to wave irradiation conditions for 90 min at 130° C. The mixture was diluted with EtOAc and washed with water and brine. The organics were dried over Na$_2$SO$_4$ and concentrated in vacuo. The crude product was purified by column chromatography (EtOAc/hexanes, 0-80% gradient) to obtain Example 5A (1.0 g, 4.9 mmol, 93% yield).

Example 5

Example 5 was synthesized from Example 5A and Intermediate 1 using General Route 2. MS (ESI) m/z 337.3 (M+H). $^1$H NMR (500 MHz, CD$_3$OD) δ 7.98 (m, 1H), 7.92 (d, J=7.2 Hz, 1H), 7.86 (d, J=8.5 Hz, 1H), 7.81 (m, 1H), 7.63 (d, J=7.7 Hz, 1H), 7.50 (m, 1H), 7.21-7.14 (m, 1H), 6.47 (s, 1H), 5.68 (s, 2H).

Example 6: 7-((1-Ethyl-5-(trifluoromethyl)-1H-pyrazol-3-yl)methoxy)-3H-[1,2,3]triazolo[4,5-b]pyridin-5-amine

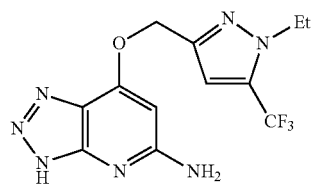 [SMILES: CCn1nc(COc2cc(N)nc3[nH]nnc23)cc1C(F)(F)F]

Example 6A: Di-tert-butyl(4-((1-ethyl-5-(trifluoromethyl)-1H-pyrazol-3-yl)methoxy) pyridine-2,6-diyl)bis(tert-butoxycarbonylcarbamate)

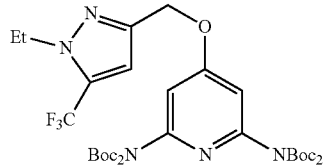

DEAD (0.24 mL, 1.5 mmol) was added to a mixture of Intermediate 4 (400 mg, 0.76 mmol), (1-ethyl-5-(trifluoromethyl)-1H-pyrazol-3-yl)methanol (220 mg, 1.1 mmol) and triphenylphosphine (400 mg, 1.5 mmol) in THF (4.0 mL), and the mixture was stirred at rt for 3 days. The mixture was concentrated, and the crude product was purified by flash chromatography (loading in chloroform, 0% to 75% EtOAc in hexane over 10 min using a 4 g silica gel cartridge) to yield Intermediate 6A (490 mg, 0.70 mmol, 92% yield) as a clear oil. MS (ESI) m/z 702.2 (M+H).

Example 6B: 4-((1-Ethyl-5-(trifluoromethyl)-1H-pyrazol-3-yl)methoxy)pyridine-2,6-diamine

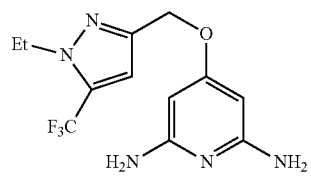 [SMILES: CCn1nc(COc2cc(N)nc(N)c2)cc1C(F)(F)F]

TFA (4 mL) was added to a solution of Example 6A (600 mg, 0.86 mmol) in DCM (4 mL), and the mixture was stirred at rt for 4 h. The mixture was concentrated, and the crude material was used in the next reaction without purification. MS (ESI) m/z 302.1 (M+H).

Example 6C: (E)-3-((4-Chlorophenyl)diazenyl)-4-((1-ethyl-5-(trifluoromethyl)-1H-pyrazol-3-yl)methoxy)pyridine-2,6-diamine

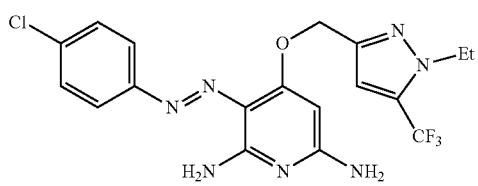 [SMILES: CCn1nc(COc2cc(N)nc(N)c2/N=N/c2ccc(Cl)cc2)cc1C(F)(F)F]

A solution of 6.0 N HCl (0.54 mL, 3.3 mmol) was added to 4-chloroaniline (120 mg, 0.94 mmol) with vigorous stirring at 0° C. A solution of sodium nitrite (59 mg, 0.86 mmol) in water (1.0 mL) was added. After stirring for 30 min, urea (5.1 mg, 0.085 mmol) was added to destroy excess NaNO$_2$. The above solution was added to a suspension of Example 6B (360 mg, 0.86 mmol) in a mixture of water (5 mL), EtOAc (2 mL) and MeOH (1 mL). After 30 min, sodium acetate (320 mg, 3.9 mmol) was added, and the mixture was stirred overnight. The mixture was partially concentrated and partitioned between EtOAc and NaHCO$_3$. The combined organics were washed with brine, dried over Na$_2$SO$_4$ and concentrated in vacuo to yield Example 6C as an orange solid that was carried into the next step without purification. MS (ESI) m/z 440.0 (M+H).

Example 6D: 4-((1-Ethyl-5-(trifluoromethyl)-1H-pyrazol-3-yl)methoxy)pyridine-2,3,6-triamine

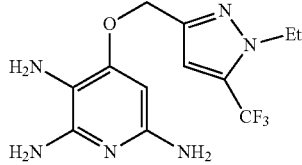 [SMILES: CCn1nc(COc2cc(N)nc(N)c2N)cc1C(F)(F)F]

A mixture of Example 6C (380 mg, 0.86 mmol) and zinc (170 mg, 2.6 mmol) in EtOH (4.3 mL)/acetic acid (250 µL, 4.3 mmol) was stirred at 70° C. for 2 h. The mixture was filtered and concentrated. The crude residue was dissolved in 4.0 mL of 7.0 M NH$_3$ in MeOH and concentrated. The crude product was purified by column chromatography (2.0 M NH$_3$ in MeOH/CH$_2$Cl$_2$, 0-20% gradient) to yield Example 6D (220 mg, 0.71 mmol, 83% yield). MS (ESI) m/z 317.1 (M+H).

Example 6

Isoamyl nitrite (86 µL, 0.64 mmol) was added to a mixture of Example 6D (220 mg, 0.71 mmol) in THF (7.0 mL) and acetic acid (200 µL) and the mixture was stirred at rt overnight. The mixture was concentrated and purified by preparatory HPLC to yield Example 6 (220 mg, 0.49 mmol, 69% yield) as a yellow solid. MS (ESI) m/z 328.2 (M+H). $^1$H NMR (500 MHz, CD$_3$OD) δ 6.95 (s, 1H), 6.48 (s, 1H), 5.48 (s, 2H), 4.33 (q, J=7.2 Hz, 2H), 1.48 (t, J=7.2 Hz, 3H). Analytical HPLC Col A: 5.23 min, 99%; Col B: 5.75 min, 99%.

Example 7: 7-(Quinolin-8-ylmethoxy)-3H-[1,2,3]triazolo[4,5-b]pyridin-5-amine

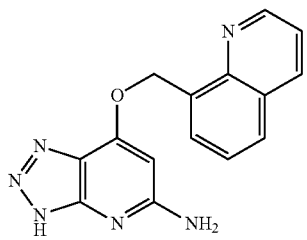 [SMILES: Nc1cc(OCc2cccc3cccnc23)c2nn[nH]c2n1]

Example 7 was synthesized from Intermediate 4 and 8-(bromomethyl) quinoline using General Route 3. MS (ESI) m/z 293 (M+H). $^1$H NMR (500 MHz, CD$_3$OD) δ 8.96 (dd, J=4.3, 1.8 Hz, 1H), 8.46 (dd, J=8.4, 1.8 Hz, 1H), 8.09-8.02 (m, 2H), 7.75-7.67 (m, 1H), 7.63 (dd, J=8.4, 4.3 Hz, 1H), 6.56 (s, 1H), 6.15 (s, 2H). Analytical HPLC Col A: 3.39 min, 81%; Col B: 3.52 min, 81%.

Example 8: 7-((1-Methyl-1H-indazol-7-yl)methoxy)-3H-[1,2,3]triazolo[4,5-b]pyridin-5-amine

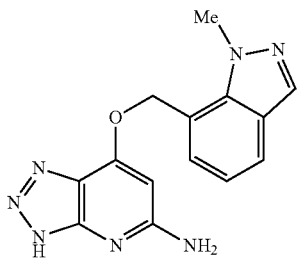 [SMILES: Cn1ncc2cccc(COc3cc(N)nc4[nH]nnc34)c21]

Example 8 was synthesized from Intermediate 4 and 7-(bromomethyl)-1-methyl-1H-indazole using General Route 3. MS (ESI) m/z 296 (M+H). $^1$H NMR (500 MHz, CD$_3$OD) δ 8.06 (s, 1H), 7.86 (dd, J=8.1, 1.0 Hz, 1H), 7.58 (d, J=6.9 Hz, 1H), 7.20 (dd, J=8.3, 7.2 Hz, 1H), 6.55 (s, 1H), 5.93 (s, 2H), 4.28 (s, 3H). Analytical HPLC Col A: 4.02 min, 90%; Col B: 4.21 min, 88%.

Example 9: 7-((1-Methyl-1H-indazol-6-yl)methoxy)-3H-[1,2,3]triazolo[4,5-b]pyridin-5-amine

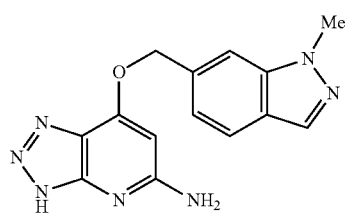 [SMILES: Cn1ncc2ccc(COc3cc(N)nc4[nH]nnc34)cc21]

Example 9 was synthesized from Intermediate 4 and (1-methyl-1H-indazol-6-yl)methanol using General Route 3. MS (ESI) m/z 296 (M+H). $^1$H NMR (500 MHz, CD$_3$OD) δ 8.02 (d, J=1.1 Hz, 1H), 7.82 (dd, J=8.3, 0.6 Hz, 1H), 7.75 (s, 1H), 7.32 (dd, J=8.4, 1.2 Hz, 1H), 6.43 (s, 1H), 5.63 (s, 2H), 4.09 (s, 3H). Analytical HPLC Col A: 3.84 min, 97%.

Example 10: 7-((2-(4-Fluorophenyl)-5-methyl-2H-1,2,3-triazol-4-yl)methoxy)-3H-[1,2,3]triazolo[4,5-b]pyridin-5-amine

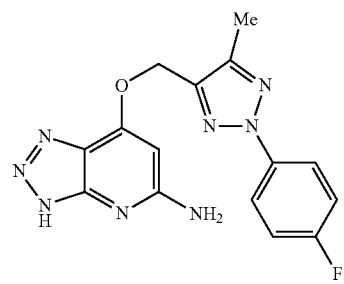 [SMILES: Cc1nn(-c2ccc(F)cc2)nc1COc1cc(N)nc2[nH]nnc12]

Example 10A: Ethyl 2-(2-(4-fluorophenyl)hydrazono)-3-oxobutanoate

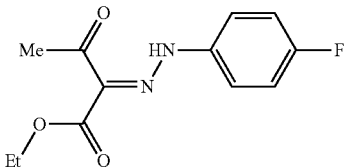 [SMILES: CCOC(=O)/C(=N/Nc1ccc(F)cc1)C(C)=O]

A solution of 4-fluoroaniline (0.85 mL, 9.0 mmol) in AcOH (6.0 mL), water (10 mL) and concentrated HCl (1.4 mL, 45 mmol) was cooled to <5° C. and a solution of sodium nitrite (0.75 g, 11 mmol) in water (10 mL) was added slowly. The reaction mixture turned from a brown solution to a thick yellow slush. The resultant mixture was slowly added to a mixture of ethyl 3-oxobutanoate (1.2 g, 9.0 mmol) and sodium acetate (3.7 g, 45 mmol) in 1.0 M sodium carbonate (10 mL) and EtOH (10 mL) at 0° C. The resulting mixture was stirred for 2 hrs and then diluted with H$_2$O (20 mL) and extracted with EtOAc (25 mL×2). The combined organics were washed with water (20 mL), brine (20 mL) and dried over Na$_2$SO$_4$. The solution was concentrated in vacuo to give the title product as a dark brown solid (2.3 g, 9.0 mmol, 100% yield), which was used without purification in the next step. MS (ESI) m/z 253.3 (M+H).

Example 10B: Ethyl 2-(4-fluorophenyl)-5-methyl-2H-1,2,3-triazole-4-carboxylate

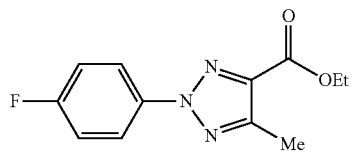 [SMILES: CCOC(=O)c1nn(-c2ccc(F)cc2)nc1C]

To a solution of Example 10A (2.2 g, 8.7 mmol) in EtOH (25 mL) was added copper (II) chloride (2.6 g, 19 mmol) and ammonium acetate (6.7 g, 87 mmol). The reaction mixture was refluxed for 6 hrs and then cooled to rt. The reaction mixture was poured into a mixture of ice and concentrated HCl, which caused precipitation of the product. The reaction mixture was then filtered and the solids washed with 2.0 N HCl. The resulting solid was purified by recrystallization from hot EtOH to afford the title compound as a light tan solid (1.6 g, 6.4 mmol, 74% yield). MS (ESI) m/z 250.3 (M+H).

Example 10C: (2-(4-Fluorophenyl)-5-methyl-2H-1,2,3-triazol-4-yl)methanol

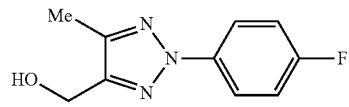 [SMILES: Cc1nn(-c2ccc(F)cc2)nc1CO]

To a solution of Example 10B (0.50 g, 2.0 mmol) in THF (10 mL) at 0° C. was added LiAlH$_4$ (0.15 g, 4.0 mmol). The reaction mixture was stirred for 2 hrs while gradually warming to rt. The reaction was quenched with 10% NaOH and then diluted with H$_2$O (20 mL) and extracted with EtOAc (25 mL×2). The combined extracts were washed with brine (20 mL), dried over Na$_2$SO$_4$ and concentrated in vacuo to give the title product as a tan solid (420 mg, 2.0 mmol, 100% yield). MS (ESI) m/z 208.3 (M+H).

Example 10

Example 10 was synthesized from Example 10C and Intermediate 4 using General Route 3. MS (ESI) m/z: 341.0 (M+H)$^+$. $^1$H NMR (500 MHz, CD$_3$OD) δ 8.02 (m, 2H), 7.24 (m, 2H), 6.52 (s, 1H), 5.64 (s, 2H), 2.46 (s, 3H). Analytical HPLC Col A: 5.93 min, 99%; Col B: 6.21 min, 97%.

Example 11: 7-((2-(4-Methoxyphenyl)-5-methyl-2H-1,2,3-triazol-4-yl)methoxy)-3H-[1,2,3]triazolo[4,5-b]pyridin-5-amine

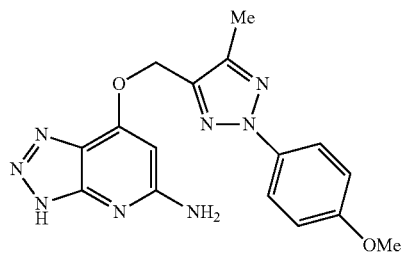 [SMILES: COc1ccc(-n2nc(C)c(COc3cc(N)nc4[nH]nnc34)n2)cc1]

Example 11 was synthesize from Intermediate 4 and 4-methoxyaniline using procedures described in Example 10. MS (ESI) m/z: 353.0 (M+H)$^+$. $^1$H NMR (500 MHz, CD$_3$OD) δ 7.98-7.80 (m, 2H), 7.13-6.93 (m, 2H), 6.50 (s, 1H), 5.62 (s, 2H), 3.84 (s, 3H), 2.47 (s, 3H). Analytical HPLC Col A: 5.73 min, 99%; Col B: 5.98 min, 98%.

Example 12: 7-((2-(3-Fluorophenyl)-5-methyl-2H-1,2,3-triazol-4-yl)methoxy)-3H-[1,2,3]triazolo[4,5-b]pyridin-5-amine

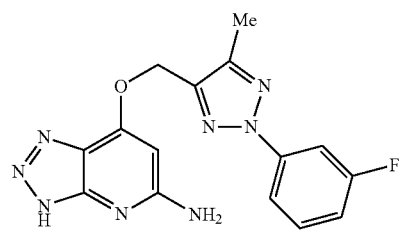 [SMILES: Cc1nn(-c2cccc(F)c2)nc1COc1cc(N)nc2[nH]nnc12]

Example 12 was synthesized from Intermediate 4 and 3-fluoroaniline using procedures described in Example 10. MS (ESI) m/z: 341.2 (M+H)$^+$. $^1$H NMR (500 MHz, CD$_3$OD) δ 7.88 (d, J=8.3 Hz, 1H), 7.80 (dt, J=9.9, 2.2 Hz, 1H), 7.53 (td, J=8.2, 6.2 Hz, 1H), 7.13 (td, J=8.4, 2.5 Hz, 1H), 6.58-6.41 (m, 1H), 5.67 (s, 2H), 2.56-2.41 (m, 3H). Analytical HPLC Col A: 6.20 min, 99%; Col B: 6.25 min, 97%.

Example 13: 7-((2-(3-Methoxyphenyl)-5-methyl-2H-1,2,3-triazol-4-yl)methoxy)-3H-[1,2,3]triazolo[4,5-b]pyridin-5-amine

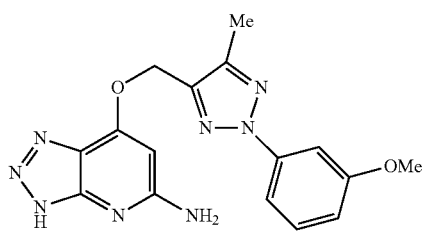 [SMILES: COc1cccc(-n2nc(C)c(COc3cc(N)nc4[nH]nnc34)n2)c1]

Example 13 was synthesized from Intermediate 4 and 3-methoxyaniline using procedures described in Example 10. MS (ESI) m/z: 353.2 (M+H)+. $^1$H NMR (500 MHz, CD$_3$OD) δ 7.69-7.49 (m, 2H), 7.38 (t, J=8.0 Hz, 1H), 6.92 (d, J=8.0 Hz, 1H), 6.50 (s, 1H), 5.63 (s, 2H), 3.86 (s, 3H), 2.47 (s, 3H). Analytical HPLC Col A: 5.96 min, 97%; Col B: 6.16 min, 95%.

Example 14: 7-((3-Phenylisoxazol-5-yl)methoxy)-3H-[1,2,3]triazolo[4,5-b]pyridin-5-amine

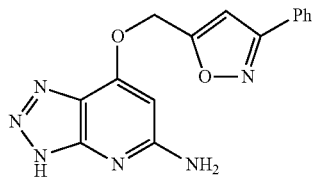 [SMILES: Nc1cc(OCc2cc(-c3ccccc3)no2)c2nn[nH]c2n1]

Example 14A: 5-(Bromomethyl)-3-phenylisoxazole

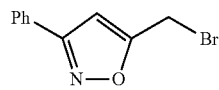 [SMILES: BrCc1cc(-c2ccccc2)no1]

(3-Phenylisoxazol-5-yl)methanol (2.0 g, 11 mmol) and phosphorus tribromide (1.1 ml, 11 mmol) in ether (30 mL) were stirred overnight at rt. The solution was partitioned between water/brine and ether. The organic layer was filtered through silica and concentrated to furnish Example 14A (1.5 g, 6.30 mmol, 55.2% yield) as a white solid. $^1$H NMR (500 MHz, CD$_3$OD) δ 7.83 (dd, J=7.8, 1.8 Hz, 2H), 7.58-7.40 (m, 3H), 6.88 (s, 1H), 4.55 (s, 2H).

Example 14

Example 14 was synthesized from Example 14A and Intermediate 4 using General Route 3. MS (ESI) m/z 309.2 (M+H). $^1$H NMR (500 MHz, CD$_3$OD) δ 7.89-7.84 (m, 2H), 7.55-7.42 (m, 3H), 7.02 (s, 1H), 6.46 (s, 1H), 5.65 (s, 2H). Analytical HPLC Col A: 5.36 min, 92%; Col B: 6.08 min, 97%.

Example 15: 7-((1-Methyl-1H-indazol-4-yl)methoxy)-3H-[1,2,3]triazolo[4,5-b]pyridin-5-amine

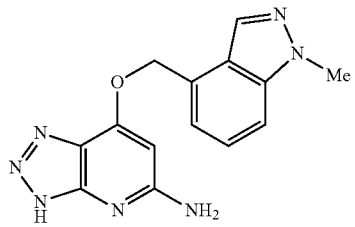 [SMILES: Cn1ncc2c(COc3cc(N)nc4[nH]nnc34)cccc21]

Example 15A: 4-(Bromomethyl)-1-methyl-1H-indazole

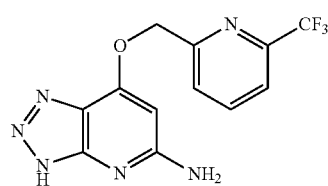 [SMILES: Nc1cc(OCc2cccc(C(F)(F)F)n2)c2nn[nH]c2n1]

Example 15A was synthesized using a method analogous to that used to make Example 14A. $^1$H NMR (500 MHz, CDCl$_3$) δ 8.16 (d, J=0.8 Hz, 1H), 7.38 (d, J=8.3 Hz, 1H), 7.33 (dd, J=8.5, 6.9 Hz, 1H), 7.16 (d, J=6.9 Hz, 1H), 4.81 (s, 2H), 4.10 (s, 3H).

Example 15

Example 15 was synthesized from Example 15A and Intermediate 4 using General Route 3. MS (ESI) m/z 296.2 (M+H). $^1$H NMR (500 MHz, CD$_3$OD) δ 8.23 (d, J=1.1 Hz, 1H), 7.64 (d, J=8.5 Hz, 1H), 7.50 (dd, J=8.4, 7.0 Hz, 1H), 7.36 (dd, J=7.0, 0.7 Hz, 1H), 6.43 (s, 1H), 5.86 (s, 2H), 4.12 (s, 3H). Analytical HPLC Col A: 3.99 min, 93%; Col B: 4.49 min, 93%.

Example 16: 7-((6-(Trifluoromethyl)pyridin-2-yl)methoxy)-3H-[1,2,3]triazolo[4,5-b]pyridin-5-amine Example 16 was synthesized from (6-(trifluoromethyl)pyridin-2-yl)methanol and Intermediate 4 using General Route 3. MS (ESI) m/z 311.1 (M+H). $^1$H NMR (500 MHz, CD$_3$OD) δ 8.84 (d, J=4.1 Hz, 1H), 8.31-8.22 (m, 1H), 7.66 (dd, J=8.0, 5.0 Hz, 1H), 6.46 (s, 1H), 5.78 (s, 2H).

Example 17: 7-((1-Methyl-5-phenyl-1H-pyrazol-3-yl)methoxy)-3H-[1,2,3]triazolo[4,5-b]pyridin-5-amine

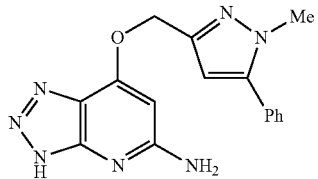 [SMILES: Cn1nc(COc2cc(N)nc3[nH]nnc23)cc1-c1ccccc1]

Example 17 was synthesized from (1-methyl-5-phenyl-1H-pyrazol-3-yl)methanol and Intermediate 4 using General Route 3. MS (ESI) m/z 322.1 (M+H). $^1$H NMR (500 MHz, CD$_3$OD) δ 7.52-7.40 (m, 5H), 6.57 (s, 1H), 6.53 (s, 1H), 5.47 (s, 2H), 3.88 (s, 3H). Analytical HPLC Col A: 5.12 min, 98%; Col B: 5.50 min, 92%.

Example 18: 7-((1-Methyl-3-phenyl-1H-pyrazol-5-yl)methoxy)-3H-[1,2,3]triazolo[4,5-b]pyridin-5-amine

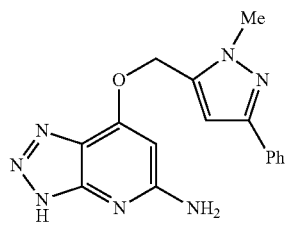 [SMILES: Cn1nc(-c2ccccc2)cc1COc1cc(N)nc2[nH]nnc12]

Example 18 was synthesized from (1-methyl-3-phenyl-1H-pyrazol-5-yl)methanol and Intermediate 4 using General Route 3. MS (ESI) m/z 322.1 (M+H). $^1$H NMR (500 MHz, CD$_3$OD) δ 7.77 (dd, J=8.4, 1.2 Hz, 2H), 7.43-7.36 (m, 2H), 7.35-7.27 (m, 1H), 6.88 (s, 1H), 6.48 (s, 1H), 5.64 (s, 2H), 4.00 (s, 3H). Analytical HPLC Col A: 5.10 min, 99%; Col B: 5.35 min, 93%.

Example 19: 7-((1-Ethyl-3-(trifluoromethyl)-1H-pyrazol-5-yl)methoxy)-3H-[1,2,3]triazolo[4,5-b]pyridin-5-amine

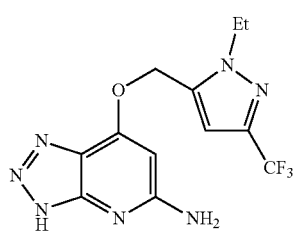 [SMILES: CCn1nc(C(F)(F)F)cc1COc1cc(N)nc2[nH]nnc12]

Example 19 was synthesized from (1-ethyl-3-(trifluoromethyl)-1H-pyrazol-5-yl)methanol and Intermediate 4 using General Route 3. MS (ESI) m/z 328.2 (M+H). $^1$H NMR (500 MHz, CD$_3$OD) δ 6.95 (s, 1H), 6.47 (s, 1H), 5.48 (s, 2H), 4.33 (q, J=7.2 Hz, 2H), 1.48 (t, J=7.2 Hz, 3H). Analytical HPLC Col A: 5.81 min, 98%; Col B: 5.89 min, 98%.

Example 20: 7-((3-Cyclopropyl-1-methyl-1H-pyrazol-5-yl)methoxy)-3H-[1,2,3]triazolo [4,5-b]pyridin-5-amine

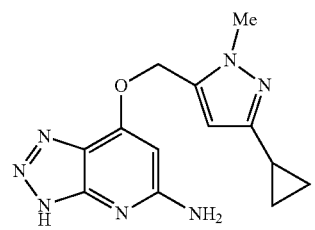 [SMILES: Cn1nc(C2CC2)cc1COc1cc(N)nc2[nH]nnc12]

Example 20 was synthesized from (3-cyclopropyl-1-methyl-1H-pyrazol-5-yl)methanol and Intermediate 4 using General Route 3. MS (ESI) m/z 284.1 (M+H). $^1$H NMR (500 MHz, ACN-d$_3$) δ 6.35 (s, 1H), 6.20 (s, 1H), 5.41 (s, 2H), 3.83 (s, 3H), 1.92-1.88 (m, 1H), 0.96-0.90 (m, 2H), 0.72-0.66 (m, 2H). Analytical HPLC Col A: 3.89 min, 97%; Col B: 4.10 min, 98%.

Example 21: 7-((5-Methyl-2-phenyl-2H-1,2,3-triazol-4-yl)methoxy)-3H-[1,2,3]triazolo [4,5-b]pyridin-5-amine

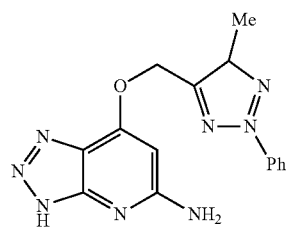

Example 21 was synthesized from Intermediate 1 and (5-methyl-2-phenyl-2H-1,2,3-triazol-4-yl)methanol using General Route 2. MS (ESI) m/z 323.0 (M+H). $^1$H NMR (400 MHz, CD$_3$OD) δ 8.10-7.99 (m, 2H), 7.57-7.45 (m, 2H), 7.39 (d, J=7.1 Hz, 1H), 6.50 (s, 1H), 5.65 (s, 2H), 2.48 (s, 3H). Analytical HPLC Col A: 6.88 min, 97%; Col B: 8.05 min, 96%.

Example 22: 7-((1-Phenyl-1H-pyrazol-4-yl)methoxy)-3H-[1,2,3]triazolo[4,5-b]pyridin-5-amine

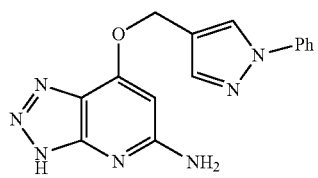 [SMILES: Nc1cc(OCc2cnn(-c3ccccc3)c2)c2nn[nH]c2n1]

Example 22A: (1-Phenyl-1H-pyrazol-4-yl)methanol

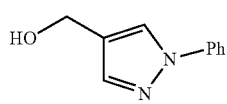 [SMILES: OCc1cnn(-c2ccccc2)c1]

To a solution of 1-phenyl-1H-pyrazole-4-carboxylic acid (590 mg, 3.1 mmol) in THF (6.9 mL) at rt was added borane-THF complex (6.2 mL, 6.2 mmol, 1 M in THF), and the reaction mixture was stirred over night. The mixture was quenched by the slow addition of 1M NaOH and pouring into water. The mixture was extracted with ether (2×). The combined organics were washed with water and brine, dried over $Na_2SO_4$, and concentrated to give Example 22A a white solid. MS (ESI) m/z 175.1 (M+H). The crude product was used in the next synthetic step without further purification.

Example 22

Example 22 was synthesized from Intermediate 4 and Example 22A using General Route 3. MS (ESI) m/z 308.1 (M+H). $^1$H NMR (400 MHz, $CD_3OD$) δ 8.44 (s, 1H), 7.87 (s, 1H), 7.72 (d, J=8.2 Hz, 2H), 7.50-7.42 (m, 2H), 7.37-7.26 (m, 1H), 6.40 (s, 1H), 5.46 (s, 2H). Analytical HPLC Col A: 4.85 min, 97%; Col B: 5.36 min, 94%.

Example 23: 7-((5-Isopropyl-1-phenyl-1H-1,2,3-triazol-4-yl)methoxy)-3H-[1,2,3]triazolo[4,5-b]pyridin-5-amine

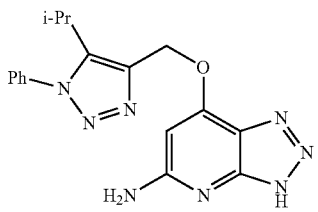 [SMILES: CC(C)c1c(COc2cc(N)nc3[nH]nnc23)nnn1-c1ccccc1]

Example 23A: (5-Isopropyl-1-phenyl-1H-1,2,3-triazol-4-yl)methanol

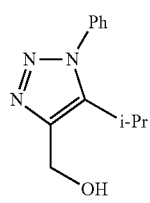

Example 23A was synthesized using a similar method to that was used to synthesize Example 22A using 5-isopropyl-1-phenyl-1H-1,2,3-triazole-4-carboxylic acid. MS (ESI) m/z 218.4 (M+H).

Example 23

Example 23 was synthesized from Intermediate 1 and Example 23A using General Route 2. MS (ESI) m/z 351.2 (M+H). $^1$H NMR (400 MHz, $CD_3OD$) δ 7.70-7.61 (m, 3H), 7.55-7.45 (m, 2H), 6.64 (s, 1H), 5.70 (s, 2H), 3.22-3.10 (m, 1H), 1.31 (d, J=1.0 Hz, 6H). Analytical HPLC Col A: 5.22 min, 97%; Col B: 5.81 min, 97%.

Example 24: 7-((3-Phenyl-1,2,4-oxadiazol-5-yl)methoxy)-3H-[1,2,3]triazolo[4,5-b]pyridin-5-amine

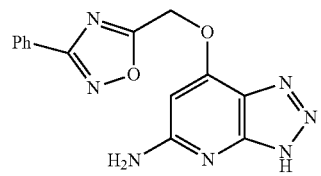 [SMILES: Nc1cc(OCc2nc(-c3ccccc3)no2)c2nn[nH]c2n1]

Example 24 was synthesized from (3-phenyl-1,2,4-oxadiazol-5-yl)methanol and Intermediate 4 using General Route 3. MS (ESI) m/z 310 (M+H). $^1$H NMR (500 MHz, $CD_3OD$) δ 8.16-8.04 (m, 2H), 7.63-7.50 (m, 3H), 6.45 (s, 1H), 5.96 (s, 2H). Analytical HPLC Col A: 5.52 min, 87%; Col B: 6.52 min, 84%.

Example 25: 7-((5-Phenyloxazol-2-yl)methoxy)-3H-[1,2,3]triazolo[4,5-b]pyridin-5-amine

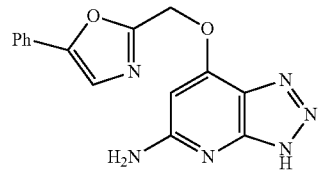 [SMILES: Nc1cc(OCc2ncc(-c3ccccc3)o2)c2nn[nH]c2n1]

Example 25 was synthesized from (3-phenyl-1,2,4-oxadiazol-5-yl)methanol and Intermediate 4 using General Route 3. MS (ESI) m/z 309 (M+H). $^1$H NMR (500 MHz, $CD_3OD$) δ 7.80-7.74 (m, 2H), 7.62 (s, 1H), 7.51-7.46 (m, 2H), 7.44-7.39 (m, 1H), 6.55 (s, 1H), 5.73 (s, 2H). Analytical HPLC Col A: 5.25 min, 97%; Col B: 6.36 min, 91%.

Example 26: 7-((2-Phenylthiazol-5-yl)methoxy)-3H-[1,2,3]triazolo[4,5-b]pyridin-5-amine

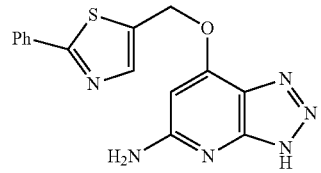

Example 26 was synthesized from 5-(bromomethyl)-2-phenylthiazole and Intermediate 4 using General Route 3. MS (ESI) m/z 325 (M+H). ¹H NMR (500 MHz, CD₃OD) δ 8.06-7.95 (m, 2H), 7.81 (s, 1H), 7.60-7.43 (m, 3H), 6.54 (s, 1H), 5.65 (s, 2H). Analytical HPLC Col A: 5.72 min, 98%; Col B: 6.13 min, 95%.

Example 27: 7-((2-(3,5-Difluorophenyl)-5-methyl-oxazol-4-yl)methoxy)-3H-[1,2,3]triazolo[4,5-b]pyridin-5-amine

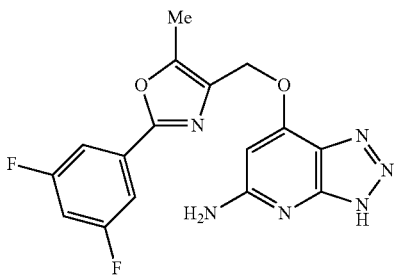 [SMILES: Cc1oc(-c2cc(F)cc(F)c2)nc1COc1cc(N)nc2[nH]nnc12]

Example 27 was synthesized from Intermediate 4 and 4-(chloromethyl)-2-(3,5-difluorophenyl)-5-methyloxazole using General Route 3. MS (ESI) m/z 359 (M+H). ¹H NMR (500 MHz, DMSO-d₆) δ 7.63 (dd, J=8.0, 2.2 Hz, 2H), 7.46 (m, 1H), 6.46 (s, 2H), 6.11 (s, 1H), 2.52 (s, 3H).

Example 28: 7-((1-Benzyl-1H-imidazol-5-yl)methoxy)-3H-[1,2,3]triazolo[4,5-b]pyridin-5-amine

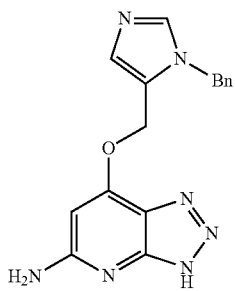 [SMILES: Nc1cc(OCc2cncn2Cc2ccccc2)c2nn[nH]c2n1]

DEAD (0.030 mL, 0.19 mmol) was added to a solution of Intermediate 5 (0.060 g, 0.094 mmol), (1-benzyl-1H-imidazol-5-yl)methanol (0.018 g, 0.094 mmol), and triphenylphosphine (0.050 g, 0.19 mmol) in THF (0.2 mL), and the solution was allowed to stir for 30 min at rt. The mixture was concentrated. The crude ether was dissolved in DCM (4 mL). TFA (1 mL) was added which turned the solution bright yellow. After 10 min, LCMS showed reaction completion. Triethylsilane (0.028 mL, 0.17 mmol) was added until the bright yellow color dissipated. The reaction mixture was concentrated in vacuo. The crude material was purified via preparative LC/MS to yield Example 28 (10 mg, 37% yield). MS (ESI) m/z 322 (M+H). ¹H NMR (500 MHz, DMSO-d₆) δ 9.19 (s, 1H), 7.90 (s, 1H), 7.41-7.30 (m, 5H), 6.06 (br. s., 1H), 5.54 (s, 2H), 5.50 (s, 2H).

Example 29: 7-((5-Chloro-[1,2,4]triazolo[4,3-a]pyridin-3-yl)methoxy)-3H-[1,2,3]triazolo[4,5-b]pyridin-5-amine

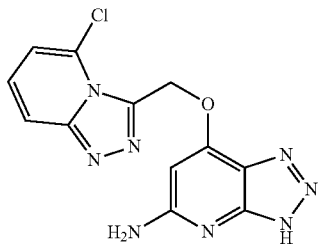 [SMILES: Nc1cc(OCc2nnc3cccc(Cl)n23)c2nn[nH]c2n1]

Example 29 was synthesized from Intermediate 4 and 5-chloro-3-(chloromethyl)-[1,2,4]triazolo[4,3-a]pyridine using General Route 3. MS (ESI) m/z 317 (M+H). ¹H NMR (500 MHz, DMSO-d₆) δ 8.02-7.86 (m, 1H), 7.51 (dd, J=9.1, 7.2 Hz, 1H), 7.33 (d, J=7.2 Hz, 1H), 6.33 (br. s., 1H), 6.06 (s, 2H).

Example 30: 7-((1-(Pyridin-2-yl)-1H-pyrazol-4-yl)methoxy)-3H-[1,2,3]triazolo[4,5-b]pyridin-5-amine

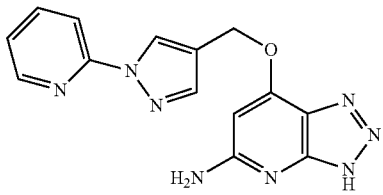 [SMILES: Nc1cc(OCc2cnn(-c3ccccn3)c2)c2nn[nH]c2n1]

Example 30 was synthesized from Intermediate 4 and (1-(pyridin-2-yl)-1H-pyrazol-4-yl)methanol using General Route 3. MS (ESI) m/z 309 (M+H). ¹H NMR (500 MHz, CD₃OD) δ 8.83 (d, J=0.5 Hz, 1H), 8.59-8.41 (m, 1H), 8.02-7.92 (m, 3H), 7.34 (ddd, J=6.5, 4.7, 1.9 Hz, 1H), 6.44 (s, 1H), 5.53 (s, 2H). Analytical HPLC Col A: 3.47 min, 88%; Col B: 4.03 min, 90%.

Example 31: 7-((2-(4-Chlorophenyl)-4-methylpyrimidin-5-yl)methoxy)-3H-[1,2,3]triazolo[4,5-b]pyridin-5-amine

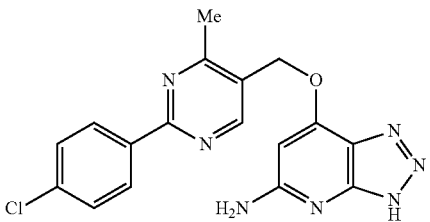 [SMILES: Cc1nc(-c2ccc(Cl)cc2)ncc1COc1cc(N)nc2[nH]nnc12]

Example 31 was synthesized from Intermediate 4 and (2-(4-chlorophenyl)-4-methylpyrimidin-5-yl)methanol using General Route 3. MS (ESI) m/z 368 (M+H). ¹H NMR (500 MHz, CD₃OD) δ 8.82 (s, 1H), 8.44-8.32 (d, J=8.5 Hz, 2H), 7.52-7.42 (d, J=8.5 Hz, 2H), 6.20 (s, 1H), 5.55 (s, 2H), 2.73 (s, 3H).

Example 32: 7-((2,3-Dihydrobenzo[b][1,4]dioxin-2-yl)methoxy)-3H-[1,2,3]triazolo[4,5-b]pyridin-5-amine

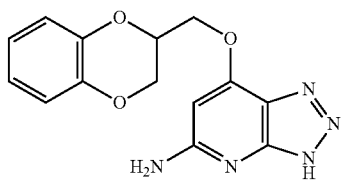 [SMILES: Nc1cc(OCC2COc3ccccc3O2)c2nn[nH]c2n1]

Example 32 was synthesized from (2,3-dihydrobenzo[b][1,4]dioxin-2-yl)methanol and Intermediate 4 using General Route 3. MS (ESI) m/z 300.0 (M+H). $^1$H NMR (500 MHz, DMSO-$d_6$) δ 6.96-6.89 (m, 2H), 6.89-6.83 (m, 2H), 6.17 (br. s., 1H), 4.76-4.70 (m, 1H), 4.61 (dd, J=11.0, 3.6 Hz, 1H), 4.54 (dd, J=10.9, 5.9 Hz, 1H), 4.47 (dd, J=11.6, 2.5 Hz, 1H), 4.22 (dd, J=11.4, 7.0 Hz, 1H).

Example 33: 7-(Chroman-2-ylmethoxy)-3H-[1,2,3]triazolo[4,5-b]pyridin-5-amine

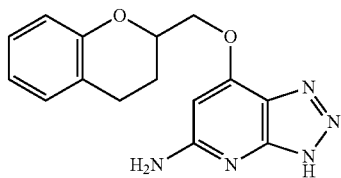 [SMILES: Nc1cc(OCC2CCc3ccccc3O2)c2nn[nH]c2n1]

Example 33 was synthesized from (1,2,3,4-tetrahydronaphthalen-1-yl)methanol and Intermediate 4 using General Route 3. MS (ESI) m/z 298.2 (M+H). $^1$H NMR (500 MHz, CDCl$_3$) δ 7.13-7.01 (m, 2H), 6.87-6.83 (m, 1H), 6.81-6.78 (m, 1H), 6.13 (s, 1H), 4.57-4.48 (m, 3H), 3.05-2.92 (m, 1H), 2.91-2.81 (m, 1H), 2.32-2.20 (m, 1H), 2.10-1.98 (m, 1H).

Example 34: 7-(Chroman-3-ylmethoxy)-3H-[1,2,3]triazolo[4,5-b]pyridin-5-amine

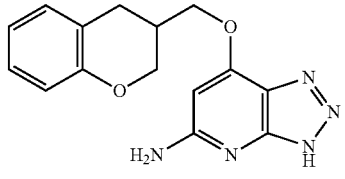 [SMILES: Nc1cc(OCC2COc3ccccc3C2)c2nn[nH]c2n1]

Example 34 was synthesized from chroman-3-ylmethanol and Intermediate 4 using General Route 3. MS (ESI) m/z 298.2 (M+H). $^1$H NMR (500 MHz, CDCl$_3$) δ 7.11-7.06 (m, 2H), 6.89-6.84 (m, J=7.4, 7.4, 1.1 Hz, 1H), 6.80 (dd, J=8.5, 1.1 Hz, 1H), 6.04 (s, 1H), 4.42-4.37 (m, J=10.7, 1.9 Hz, 1H), 4.34-4.30 (m, 2H), 4.28-4.20 (m, 3H), 3.09 (dd, J=16.6, 5.6 Hz, 1H), 2.84 (dd, J=16.5, 7.2 Hz, 1H), 2.78-2.69 (m, 1H).

Example 35: 7-((1-Methyl-1H-benzo[d]imidazol-4-yl)methoxy)-3H-[1,2,3]triazolo[4,5-b]pyridin-5-amine

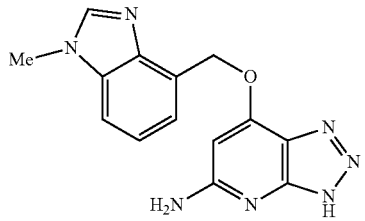 [SMILES: Cn1cnc2c(COc3cc(N)nc4[nH]nnc34)cccc21]

Example 35A: (1H-Benzo[d]imidazol-4-yl)methanol

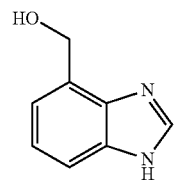 [SMILES: OCc1cccc2[nH]cnc12]

To a solution of 1H-benzo[d]imidazole-4-carboxylic acid, HCl (5.7 g, 29 mmol) in THF (20 mL) was added LiAlH$_4$ (86 mL, 86 mmol, 1 M in THF). The resulting reaction solution was heated at 50° C. for 3 h. The reaction mixture was quenched with 30 mL water, 30 mL 1N NaOH and 90 mL water. The mixture was stirred for 2 h, filtered and the solid was washed 3× with ether. The filtrates combined and extracted with EtOAc (3×), washed with NaHCO$_3$ solution and brine, dried over MgSO$_4$ and concentrated to obtain Example 35A as a yellow solid (66% yield). $^1$H NMR (500 MHz, DMSO-$d_6$) δ 8.21 (s, 1H), 7.53 (d, J=7.7 Hz, 1H), 7.37-6.60 (m, 2H), 4.90 (s, 2H).

Example 35B: 4-(((tert-Butyldimethylsilyl)oxy)methyl)-1H-benzo[d]imidazole

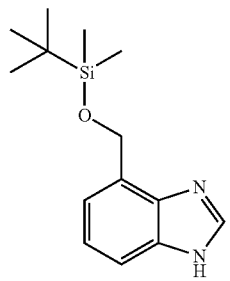 [SMILES: CC(C)(C)[Si](C)(C)OCc1cccc2[nH]cnc12]

To a solution of Example 35A (1.3 g, 8.8 mmol) in THF (5 mL) was added imidazole (0.72 g, 11 mmol) followed by TBS-Cl (1.6 g, 11 mmol). After stirring for 10 min, the reaction mixture was concentrated, and the residue was treated with saturated NaHCO$_3$, extracted with EtOAc (2×), washed with brine, dried over MgSO$_4$ and concentrated to obtain a colorless liquid. The crude was purified by column chromatography (EtOAc/hexane, 0-30% gradient) to obtain Example 35B (1.8 g, 6.9 mmol, 78% yield) as a white solid. $^1$H NMR (500 MHz, CDCl$_3$) δ 7.93 (s, 1H), 7.62-7.48 (m, 1H), 7.16-7.08 (m, 1H), 7.03-6.95 (m, 1H), 5.00 (s, 2H), 0.95-0.73 (m, 6H), 0.05-0.11 (m, 9H).

Example 35C: 4-(((tert-Butyldimethylsilyl)oxy) methyl)-1-methyl-1H-benzo[d]imidazole, and 7-(((tert-Butyldimethylsilyl)oxy)methyl)-1-methyl-1H-benzo[d]imidazole

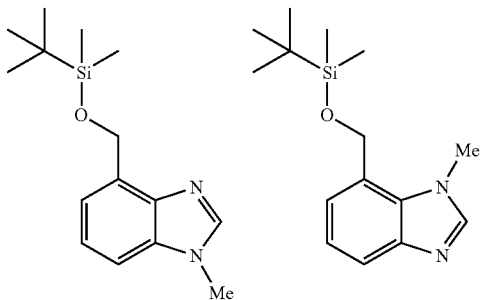 [SMILES: Cn1cnc2c(CO[Si](C)(C)C(C)(C)C)cccc21 ; Cn1cnc2cccc(CO[Si](C)(C)C(C)(C)C)c21]

To a solution of Example 35B (320 mg, 1.2 mmol) in THF (5 mL) was added NaH (60% in mineral oil) (99 mg, 2.5 mmol) followed by iodomethane (0.077 mL, 1.2 mmol). The reaction mixture was taken up in EtOAc, washed with saturated NaHCO$_3$, brine, dried over MgSO$_4$ and then concentrated to obtain a brown solid. The crude was purified by column chromatography (EtOAc/hexanes, 0-40% gradient). A mixture of 2 isomeric products was obtained (equal distribution).

Example 35D: (1-Methyl-1H-benzo[d]imidazol-4-yl)methanol, and (1-Methyl-1H-benzo[d]imidazol-7-yl)methanol

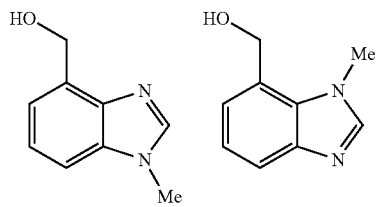

To a solution of Example 35C (600 mg) in THF (5 mL) was added HCl (1N, 5.0 mL). After stirring for 1 h, the reaction mixture was basified with saturated NaHCO$_3$, extracted with EtOAc (3×), washed with brine, dried over MgSO$_4$ and concentrated in vacuo to obtain a white solid (190 mg). MS (ESI) m/z 163.4 (M+H).

Example 35

Example 35 was synthesized from deprotected Example 35D and Intermediate 4 using General Route 3. MS (ESI) m/z 373 (M+H). $^1$H NMR (500 MHz, CD$_3$OD) δ 9.15 (s, 1H), 7.96-7.86 (m, 1H), 7.82-7.76 (m, 1H), 7.70-7.55 (m, 1H), 6.50 (s, 1H), 5.96 (s, 2H), 4.30 (s, 3H).

Example 36: 7-((1-Methyl-1H-benzo[d]imidazol-7-yl)methoxy)-3H-[1,2,3]triazolo[4,5-b]pyridin-5-amine

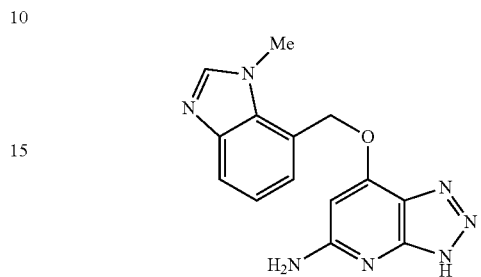

Example 36 was also isolated in the synthesis of Example 35. MS (ESI) m/z 373 (M+H). $^1$H NMR (500 MHz, CD$_3$OD) δ 8.87-8.79 (m, 1H), 7.90-7.78 (m, 1H), 7.73-7.65 (m, 1H), 7.62-7.47 (m, 1H), 6.46-6.36 (m, 1H), 5.88-5.79 (m, 2H), 4.15-4.00 (m, 3H).

Example 37: 7-((1-Benzyl-1H-benzo[d]imidazol-4-yl)methoxy)-3H-[1,2,3]triazolo[4,5-b]pyridin-5-amine

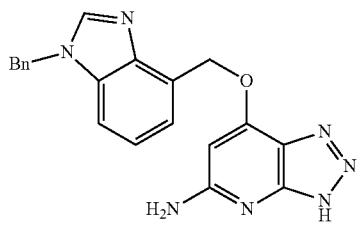 [SMILES: Nc1cc(OCc2cccc3c2ncn3Cc2ccccc2)c2nn[nH]c2n1]

Example 37A: (3-(Benzylamino)-2-nitrophenyl)methanol

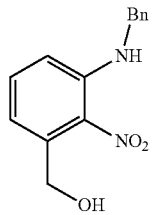

To a solution of (3-fluoro-2-nitrophenyl)methanol (700 mg, 4.1 mmol) in DMSO (2 mL) was added phenylmethanamine (880 mg, 8.2 mmol). The reaction mixture was heated at 80° C. for 2 h. The reaction mixture was extracted with EtOAc, washed with brine, dried over MgSO$_4$ and concentrated to obtain a reddish-orange solid. The product was triturated with ether to obtain Example 37A as a bright orange red solid. ¹H NMR (500 MHz, DMSO-d$_6$) δ 7.44-7.18 (m, 7H), 6.84 (dd, J=7.4, 1.1 Hz, 1H), 6.71 (d, J=8.3 Hz, 1H), 5.31 (t, J=5.8 Hz, 1H), 4.60 (d, J=5.8 Hz, 2H), 4.49 (d, J=6.1 Hz, 2H).

Example 37B: (2-Amino-3-(benzylamino)phenyl)methanol

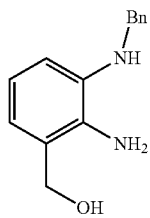 [SMILES: Nc1c(CO)cccc1NCc1ccccc1]

To a solution of (3-(benzylamino)-2-nitrophenyl)methanol (1.1 g, 4.3 mmol) in EtOH (10 mL) and acetic acid (1 mL) was added zinc (2.8 g, 43 mmol). The reaction mixture was heated at 70° C. for 2 h. The reaction mixture was extracted with EtOAc, washed brine, dried over MgSO$_4$ and concentrated to obtain a reddish-orange solid. The product was triturated with ether to obtain Example 37B (0.95 g, 4.2 mmol, 98% yield) as a red solid. ¹H NMR (500 MHz, DMSO-d$_6$) δ 7.42-7.28 (m, 6H), 7.25-7.16 (m, 2H), 6.50-6.42 (m, 1H), 6.41-6.36 (m, 1H), 6.34-6.29 (m, 1H), 4.41 (s, 2H), 4.34-4.25 (m, 2H).

Example 37C: (1-Benzyl-1H-benzo[d]imidazol-4-yl)methanol, HCl

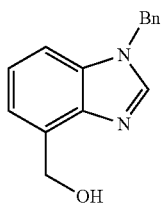 [SMILES: OCc1cccc2c1ncn2Cc1ccccc1]

To a mixture of Example 37B (0.95 g, 4.2 mmol) in 4M HCl (5 mL) was added formic acid (0.48 mL, 13 mmol). The reaction mixture was heated at reflux for 2 h, cooled to rt and basified with a Na$_2$CO$_3$ solution. The mixture was extracted with EtOAc (3×), washed with brine, dried over MgSO$_4$, and concentrated to obtain Example 37C (240 mg, 0.87 mmol, 21% yield) as a reddish solid. ¹H NMR (500 MHz, DMSO-d$_6$) δ 8.37 (s, 1H), 7.43-7.13 (m, 8H), 5.50 (s, 2H), 5.19-5.07 (m, 1H), 4.92 (d, J=5.5 Hz, 2H).

Example 37

Example 37 was obtained from Example 37C and Intermediate and Intermediate 4 using General Route 3. MS (ESI) m/z 372.3 (M+H). ¹H NMR (500 MHz, CD$_3$OD) δ 9.04 (s, 1H), 7.73 (d, J=8.5 Hz, 1H), 7.66 (d, J=7.2 Hz, 1H), 7.51 (m, 1H), 7.43-7.32 (m, 5H), 6.48 (s, 1H), 5.85 (s, 2H), 5.67 (s, 2H).

Example 38: 7-((1-Benzyl-1H-benzo[d][1,2,3]triazol-4-yl)methoxy)-3H-[1,2,3]triazolo [4,5-b]pyridin-5-amine

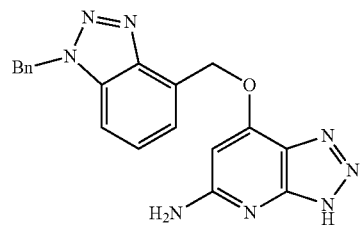 [SMILES: Nc1cc(OCc2cccc3c2nnn3Cc2ccccc2)c2nn[nH]c2n1]

Example 38A: Di-tert-butyl (4-((3-fluoro-2-nitrobenzyl)oxy)pyridine-2,6-diyl)bis(tert-butoxycarbonylcarbamate)

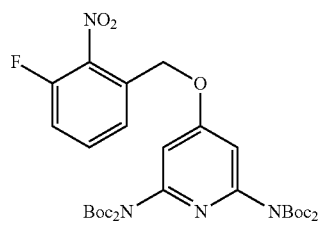

DEAD (2.0 mL, 13 mmol) was added to a mixture of Intermediate 4 (3.3 g, 6.3 mmol), (3-fluoro-2-nitrophenyl)methanol (1.1 g, 6.3 mmol) and triphenylphosphine (3.3 g, 13 mmol) in THF (8 mL). The reaction mixture was heated at 60° C. overnight. The mixture was concentrated and the crude product was purified by flash chromatography (0-50% gradient EtOAc in hexane) to yield Example 38A (4.2 g, 62 mmol, 99% yield) as a white solid. ¹H NMR (500 MHz, DMSO-d$_6$) δ 7.85-7.73 (m, 1H), 7.72-7.55 (m, 2H), 7.02 (s, 2H), 5.46 (s, 2H), 1.50-1.27 (m, 36H).

Example 38B: Di-tert-butyl (4-((3-(benzylamino)-2-nitrobenzyl)oxy)pyridine-2,6-diyl)bis (tert-butoxycarbonylcarbamate)

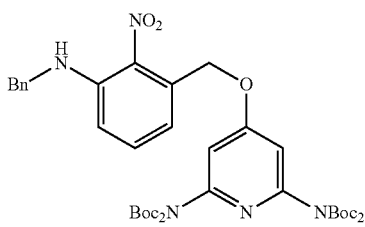

To a solution of Example 38A (0.50 g, 0.74 mmol) in DMSO (2 mL) was added phenylmethanamine (0.12 g, 1.1 mmol). The reaction mixture was heated at 60° C. for 2 h and then extracted with EtOAc, washed NaHCO₃ and brine, dried over MgSO₄ and concentrated to obtain Example 38B (0.57 g, 0.74 mmol, 99% yield) as a bright orange red solid. MS (ESI) m/z 766.5 (M+H).

Example 38C: Di-tert-butyl (4-((2-amino-3-(benzylamino)benzyl)oxy)pyridine-2,6-diyl) bis(tert-butoxycarbonylcarbamate)

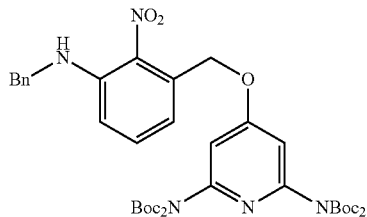

To a solution of Example 38B (600 mg, 0.78 mmol) in MeOH (20 mL) was added zinc powder (0.3 g, 0.8 mmol) followed by glacial acetic acid (0.11 mL). The resulting reaction mixture was heated at 50° C. for 2 h. The mixture was filtered through a pad of CELITE® and the filtrate was concentrated to obtain Example 38C (560 mg, 0.75 mmol, 96% yield) as an orange red product. MS (ESI) m/z 736.5 (M+H).

Example 38D: Di-tert-butyl (4-((1-benzyl-1H-benzo[d][1,2,3]triazol-4-yl)methoxy) pyridine-2,6-diyl)bis(tert-butoxycarbonylcarbamate)

To a solution of Example 38C (0.15 g, 0.20 mmol) in THF (4 mL) was added a solution of isoamyl nitrite (0.030 mL, 0.22 mmol). The resulting reaction solution was heated at 50° C. for 2 h. The crude mixture was diluted with saturated NaHCO₃ solution and extracted EtOAc (2×), washed with brine, dried over MgSO₄ and concentrated to obtain the title compound as an yellow solid. MS (ESI) m/z 747.5 (M+H).

Example 38

Example 38 was synthesized from Example 38D and Intermediate 4 using procedures found in General Route 3. MS (ESI) m/z 375 (M+H). ¹H NMR (500 MHz, CD₃OD) δ 7.76-7.70 (m, 1H), 7.67-7.54 (m, 2H), 7.35 (s, 5H), 6.51-6.47 (m, 1H), 5.99 (m, 4H).

Example 39: 7-((2-(2,4-Dichlorophenyl)-5-methyloxazol-4-yl)methoxy)-3H-[1,2,3]triazolo[4,5-b]pyridin-5-amine

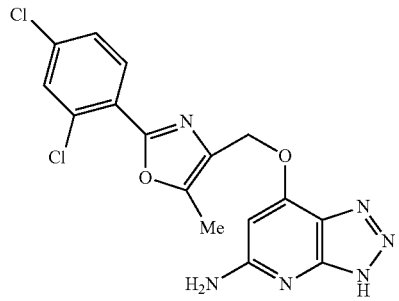 [SMILES: Cc1oc(-c2ccc(Cl)cc2Cl)nc1COc1cc(N)nc2[nH]nnc12]

4-(Chloromethyl)-2-(2,4-dichlorophenyl)-5-methyloxazole (24 mg, 0.087 mmol) was added to a mixture of Intermediate 5 (50 mg, 0.079 mmol) and K₂CO₃ (33 mg, 0.24 mmol) in DMSO (2 mL) and the reaction mixture was heated at 65° C. for 2 h. TFA (0.2 mL) was added to the reaction mixture followed by Et₃SiH (0.1 mL). The crude material was purified via preparative LC/MS to yield Example 39. (ESI) m/z 391 (M+H). ¹H NMR (500 MHz, CD₃OD) δ 7.90 (d, J=8.5 Hz, 1H), 7.66-7.55 (m, 1H), 7.41 (dd, J=8.4, 1.5 Hz, 1H), 6.25 (s, 1H), 5.38 (s, 2H), 2.54 (s, 3H).

Example 40: 7-((6-Chloroimidazo[1,2-b]pyridazin-2-yl)methoxy)-3H-[1,2,3]triazolo[4,5-b]pyridin-5-amine

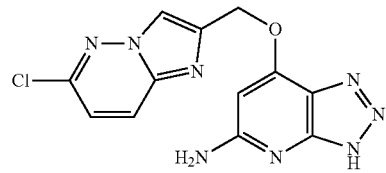 [SMILES: Nc1cc(OCc2cn3nc(Cl)ccc3n2)c2nn[nH]c2n1]

Example 40 was synthesized from Intermediate 5 and 6-chloro-2-(chloromethyl)imidazo[1,2-b]pyridazine using General Route 5. (ESI) m/z 317.1 (M+H). ¹H NMR (500 MHz, CD₃OD) δ 8.28 (s, 1H), 8.02-7.93 (m, 1H), 7.28 (d, J=9.6 Hz, 1H), 6.31 (s, 1H), 5.63 (s, 2H).

Example 41: 7-((3-Methyl-6-(trifluoromethyl)imidazo[1,2-a]pyridin-2-yl)methoxy)-3H-[1,2,3]triazolo[4,5-b]pyridin-5-amine

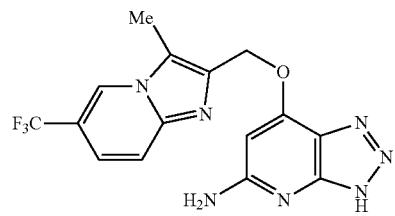 [SMILES: Cc1c(COc2cc(N)nc3[nH]nnc23)nc2ccc(C(F)(F)F)cn12]

6-Chloro-2-(chloromethyl)imidazo[1,2-b]pyridazine (19 mg, 0.094 mmol) was added to a mixture of 3-trityl-5-(tritylamino)-3H-[1,2,3]triazolo[4,5-b]pyridin-7-ol (50 mg, 0.079 mmol) and K$_2$CO$_3$ (33 mg, 0.24 mmol) in DMSO (2 mL) and the reaction mixture was heated at 65° C. for 1 h. TFA (0.2 mL) was added to the reaction mixture followed by triethylsilane (0.1 mL). The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 Acn:water with 0.1% ammonium hydroxide; Mobile Phase B: 95:5 Acn:water with 0.1% ammonium hydroxide; Gradient: 5-45% B over 20 minutes, then a 5-minute hold at 100% B; Flow: 20 mL/min. Fractions containing the desired product were combined and dried via centrifugal evaporation. (ESI) m/z 317 (M+H). $^1$H NMR (500 MHz, CD$_3$OD) δ 8.33-8.19 (m, 1H), 8.06-7.94 (m, 1H), 7.37-7.22 (m, 1H), 6.38-6.28 (m, 1H), 5.63 (s, 2H).

Example 42: 7-((2-Phenylthiazol-4-yl)methoxy)-3H-[1,2,3]triazolo[4,5-b]pyridin-5-amine

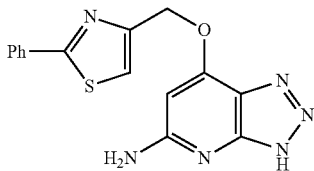 [SMILES: Nc1cc(OCc2csc(-c3ccccc3)n2)c2nn[nH]c2n1]

Example 42 was synthesized from Intermediate 5 and 4-(chloromethyl)-2-phenylthiazole using General Route 5. (ESI) m/z 364 (M+H). $^1$H NMR (500 MHz, CD$_3$OD) δ 7.95 (m, 2H), 7.70 (s, 1H), 7.48 (d, J=3.0 Hz, 3H), 6.43 (s, 1H), 5.61 (s, 2H).

Example 43: 7-((2-(4-Chloro-3-methoxyphenyl)-5-methyloxazol-4-yl)methoxy)-3H-[1,2,3]triazolo[4,5-b]pyridin-5-amine

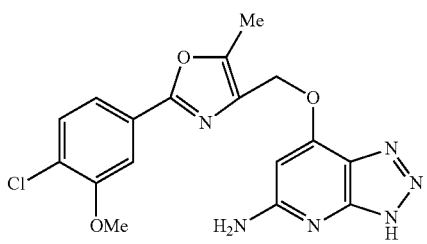 [SMILES: COc1cc(-c2nc(COc3cc(N)nc4[nH]nnc34)c(C)o2)ccc1Cl]

Example 43 was synthesized from Intermediate 5 and 2-(4-chloro-3-methoxyphenyl)-4-(chloromethyl)-5-methyloxazole using General Route 5. (ESI) m/z 325 (M+H). $^1$H NMR (500 MHz, DMSO-d$_6$) δ 7.63-7.57 (m, 2H), 7.57-7.53 (m, 1H), 6.51 (br. s., 2H), 6.10 (br. s., 1H), 5.29 (s, 2H), 3.96 (s, 3H), 2.51 (s, 2H).

Example 44: 7-((5-Ethyl-3-methylimidazo[1,2-a]pyridin-2-yl)methoxy)-3H-[1,2,3]triazolo[4,5-b]pyridin-5-amine

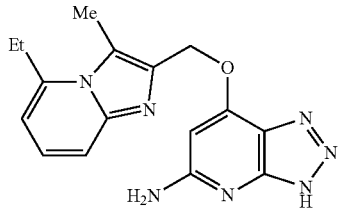 [SMILES: CCc1cccc2nc(COc3cc(N)nc4[nH]nnc34)c(C)n12]

Example 44 was synthesized from Intermediate 5 and 2-(chloromethyl)-5-ethyl-3-methylimidazo[1,2-a]pyridine using General Route 5. (ESI) m/z 387 (M+H).

Example 45: 2-(5-((5-Amino-3H-[1,2,3]triazolo[4,5-b]pyridin-7-yloxy)methyl)isoxazol-3-yl)benzonitrile

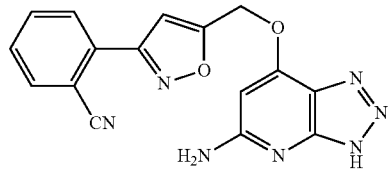 [SMILES: N#Cc1ccccc1-c1cc(COc2cc(N)nc3[nH]nnc23)on1]

Example 45 was synthesized from Intermediate 5 and 2-(5-(chloromethyl) isoxazol-3-yl)benzonitrile using General Route 5. (ESI) m/z 324 (M+H). $^1$H NMR (500 MHz, DMSO-d$_6$) δ 8.06 (d, J=7.7 Hz, 1H), 7.98 (d, J=7.7 Hz, 1H), 7.91-7.85 (m, 1H), 7.79-7.70 (m, 1H), 7.30 (s, 1H), 6.24-6.11 (m, 1H), 5.73 (s, 2H).

Example 46: 7-((5-Methyl-2-(4-(methylsulfonyl)phenyl)oxazol-4-yl)methylthio)-3H-[1,2,3]triazolo[4,5-b]pyridin-5-amine

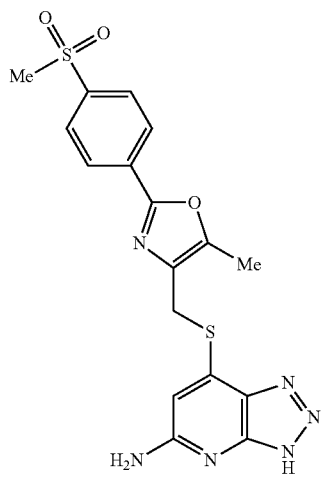 [SMILES: Cc1oc(-c2ccc(S(C)(=O)=O)cc2)nc1CSc1cc(N)nc2[nH]nnc12]

Example 46 was synthesized from Intermediate 5 and 4-(chloromethyl)-5-methyl-2-(4-(methylsulfonyl)phenyl)oxazole using General Route 5. (ESI) m/z 334 (M+H). $^1$H NMR (500 MHz, DMSO-d$_6$) δ 8.18 (d, J=8.5 Hz, 2H), 8.07 (d, J=8.5 Hz, 2H), 6.67-6.56 (m, 1H), 4.48 (s, 2H), 3.28 (s, 3H), 2.45 (s, 3H).

Example 47: 7-((3-(2,6-Dichlorophenyl)isoxazol-5-yl)methoxy)-3H-[1,2,3]triazolo[4,5-b]pyridin-5-amine

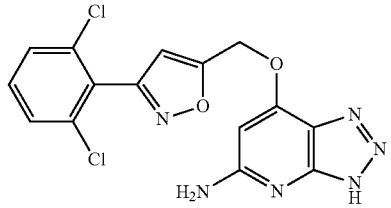 [SMILES: Nc1cc(OCc2cc(-c3c(Cl)cccc3Cl)no2)c2nn[nH]c2n1]

Example 47 was synthesized from Intermediate 5 and 5-(chloromethyl)-3-(2,6-dichlorophenyl)isoxazole using General Route 5. (ESI) m/z 377 (M+H). $^1$H NMR (500 MHz, DMSO-$d_6$) δ 7.72-7.66 (m, 2H), 7.64-7.54 (m, 1H), 6.98 (s, 1H), 6.55 (br. s., 2H), 6.14 (s, 1H), 5.69 (s, 2H).

Example 49: 7-((2-(4-Chlorophenyl)-4-methylthiazol-5-yl)methoxy)-3H-[1,2,3]triazolo [4,5-b]pyridin-5-amine

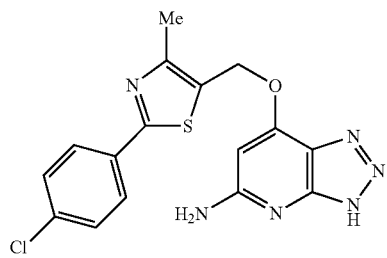 [SMILES: Cc1nc(-c2ccc(Cl)cc2)sc1COc1cc(N)nc2[nH]nnc12]

Example 49 was synthesized from (2-(4-chlorophenyl)-4-methylthiazol-5-yl)methanol and Intermediate 5 using General Route 5. MS (ESI) m/z 373.0 (M+H). $^1$H NMR (400 MHz, CD$_3$OD) δ 7.93 (d, J=8.6 Hz, 2H), 7.50 (d, J=8.8 Hz, 2H), 6.34 (s, 1H), 5.71 (s, 2H), 2.56 (s, 3H).

Example 51: 3-(((5-Amino-3H-[1,2,3]triazolo[4,5-b]pyridin-7-yl)oxy)methyl)-1-(3-chlorophenyl)-5,6-dihydro-1H-pyrazolo[3,4-c]pyridin-7(4H)-one

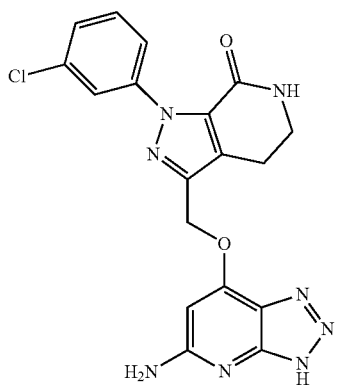 [SMILES: Nc1cc(OCc2nn(-c3cccc(Cl)c3)c3c2CCNC3=O)c2nn[nH]c2n1]

Example 51A: 2 1-(3-Chlorophenyl)-3-(hydroxymethyl)-5,6-dihydro-1H-pyrazolo[3,4-c]pyridin-7(4H)-one

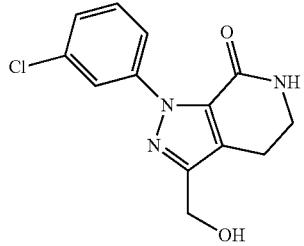 [SMILES: O=C1NCCc2c(CO)nn(-c3cccc(Cl)c3)c21]

To a solution of ethyl 1-(3-chlorophenyl)-7-oxo-4,5,6,7-tetrahydro-1H-pyrazolo[3,4-c]pyridine-3-carboxylate (100 mg, 0.31 mmol) in THF (1.5 mL) at rt was added LAH (24 mg, 0.63 mmol). The reaction mixture was stirred for 10 mins. The mixture was quenched with a few drops of 10% NaOH, diluted with water, and extracted with EtOAc. The combined organics were washed with brine, dried over Na$_2$SO$_4$ and concentrated in vacuo. The crude product was purified via column chromatography (0-100% EtOAc/hexanes) to yield Example 51A as a white solid (19 mg, 0.067 mmol, 21% yield). MS (ESI) m/z 278.0 (M+H).

Example 51

Example 51 was synthesized from Example 51A and Intermediate 5 using General Route 5. MS (ESI) m/z 411.1 (M+H). $^1$H NMR (400 MHz, CD$_3$OD) δ 7.70-7.61 (m, 1H), 7.54 (dd, J=3.1, 2.4 Hz, 1H), 7.49-7.39 (m, 2H), 6.44 (s, 1H), 5.59 (s, 2H), 3.60 (t, J=6.8 Hz, 2H), 2.98 (t, J=6.8 Hz, 2H).

Example 53: 7-((1-Benzyl-1H-indazol-3-yl)methoxy)-3H-[1,2,3]triazolo[4,5-b]pyridin-5-amine

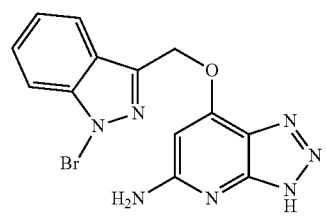 [SMILES: Nc1cc(OCc2nn(Br)c3ccccc23)c2nn[nH]c2n1]

Example 53A: (1-Benzyl-1H-indazol-3-yl)methanol

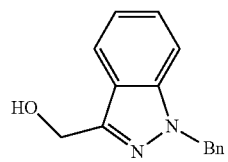 [SMILES: OCc1nn(Cc2ccccc2)c2ccccc12]

Example 53A was synthesized from 1-benzyl-1H-indazole-3-carboxylic acid in a manner similar to that described in Example 50A. MS (ESI) m/z 239.1 (M+H).

Example 53

Example 53 was synthesized from Example 53A and Intermediate 5 using General Route 5. MS (ESI) m/z 372.3 (M+H). $^1$H NMR (500 MHz, DMSO-d$_6$) δ 7.88 (d, J=8.3 Hz, 1H), 7.73 (d, J=8.5 Hz, 1H), 7.41 (t, J=7.7 Hz, 1H), 7.34-7.22 (m, 5H), 7.18 (t, J=7.4 Hz, 1H), 6.44 (br. s., 2H), 6.19 (s, 1H), 5.71 (s, 2H), 5.69 (s, 2H).

Example 54: 7-((4-Methyl-2-phenyloxazol-5-yl)methoxy)-3H-[1,2,3]triazolo[4,5-b]pyridin-5-amine

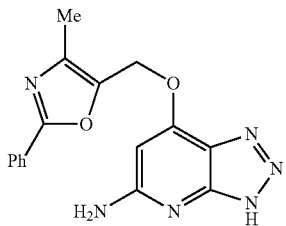 [SMILES: Cc1nc(-c2ccccc2)oc1COc1cc(N)nc2[nH]nnc12]

Example 54A: (4-Methyl-2-phenyloxazol-5-yl)methanol

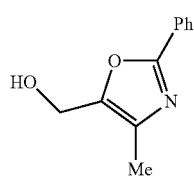

Example 54A was synthesized from methyl 4-methyl-2-phenyloxazole-5-carboxylate in a manner similar to that described in Example 51A. MS (ESI) m/z 190.1 (M+H).

Example 54

Example 54 was synthesized from Example 54A and Intermediate 5 using General Route 5. MS (ESI) m/z 322.25 (M+H). $^1$H NMR (500 MHz, DMSO-d$_6$) δ 7.99 (d, J=3.3 Hz, 2H), 7.54 (m, 3H), 6.52 (br. s., 2H), 6.13 (s, 1H), 5.51 (s, 2H), 2.28 (s, 3H).

Example 55: 7-((5-(Difluoromethyl)-2-phenyl-2H-1,2,3-triazol-4-yl)methoxy)-3H-[1,2,3]triazolo[4,5-b]pyridin-5-amine

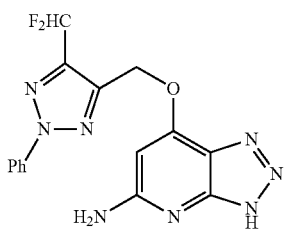 [SMILES: Nc1cc(OCc2nn(-c3ccccc3)nc2C(F)F)c2nn[nH]c2n1]

Example 55 was synthesized from ethyl 4,4-difluoro-3-oxobutanoate and aniline in a route similar to that described in preparing Example 10C, and Intermediate 5 using General Route 5. MS (ESI) m/z 359.15 (M+H). $^1$H NMR (500 MHz, DMSO-d$_6$) δ 8.06 (dd, J=8.7, 1.0 Hz, 2H), 7.65-7.38 (m, 4H), 6.21-6.11 (m, 1H), 5.66 (s, 2H).

Example 56: 7-((5-(Methoxymethyl)-2-phenyl-2H-1,2,3-triazol-4-yl)methoxy)-3H-[1,2,3]triazolo[4,5-b]pyridin-5-amine

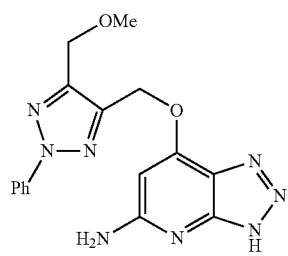

Example 56 was synthesized from ethyl 4-methoxy-3-oxobutanoate and aniline in a route similar to that described in preparing Example 10C, and Intermediate 5 using General Route 5. MS (ESI) m/z 353.2 (M+H). $^1$H NMR (500 MHz, DMSO-d$_6$) δ 8.02 (dd, J=8.5, 1.1 Hz, 2H), 7.64-7.54 (m, 2H), 7.50-7.39 (m, 1H), 6.30-6.10 (m, 1H), 5.58 (s, 2H), 4.68 (s, 2H), 3.30 (s, 3H).

Example 57: 7-((5-Ethyl-2-phenyl-2H-1,2,3-triazol-4-yl)methoxy)-3H-[1,2,3]triazolo [4,5-b]pyridin-5-amine

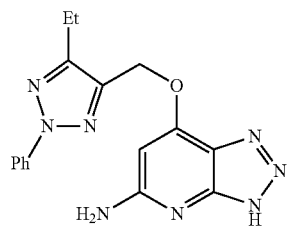

Example 57 was synthesized from ethyl 3-oxopentanoate and aniline in a route similar to that described in preparing Example 10C, and Intermediate 5 using General Route 5. MS (ESI) m/z 337.1 (M+H). $^1$H NMR (500 MHz, DMSO-d$_6$) δ 8.00 (d, J=8.0 Hz, 2H), 7.56 (t, J=7.8 Hz, 2H), 7.48-7.34 (m, 1H), 6.47 (br. s., 2H), 6.13 (br. s., 1H), 5.55 (s, 2H), 2.84 (q, J=7.1 Hz, 2H), 1.32-1.23 (m, 3H).

Example 58: 7-((2-(4-Bromophenyl)-5-methyl-2H-1,2,3-triazol-4-yl)methoxy)-3H-[1,2,3]triazolo[4,5-b]pyridin-5-amine

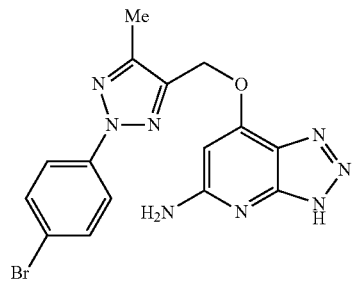 [SMILES: Cc1nn(-c2ccc(Br)cc2)nc1COc1cc(N)nc2[nH]nnc12]

Example 58 was synthesized from ethyl 3-oxobutanoate and 4-bromoaniline in a route similar to that described in preparing Example 10C, and Intermediate 5 using General Route 5. MS (ESI) m/z 401.0 (M+H). $^1$H NMR (500 MHz, DMSO-d$_6$) δ 7.96 (d, J=8.3 Hz, 2H), 7.77 (d, J=8.3 Hz, 2H), 6.54 (br. s., 2H), 6.14 (br. s., 1H), 5.55 (s, 2H), 2.45 (s, 3H).

Example 59: 7-((2-(6-Bromopyridin-3-yl)-5-methyl-2H-1,2,3-triazol-4-yl)methoxy)-3H-[1,2,3]triazolo[4,5-b]pyridin-5-amine

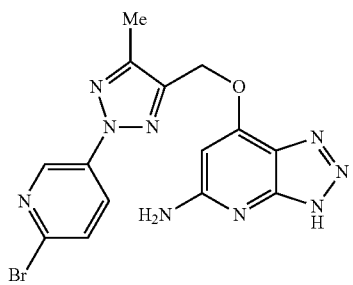

Example 59A: (2-(6-Bromopyridin-3-yl)-5-methyl-2H-1,2,3-triazol-4-yl)methanol

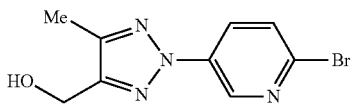

Example 59A was synthesized from ethyl 3-oxobutanoate and 6-bromopyridin-3-amine in a route similar to that described in preparing Example 10C. MS (ESI) m/z 269/271.

Example 59B: 7-((2-(6-Bromopyridin-3-yl)-5-methyl-2H-1,2,3-triazol-4-yl)methoxy)-N,3-dirityl-3H-[1,2,3]triazolo[4,5-b]pyridin-5-amine

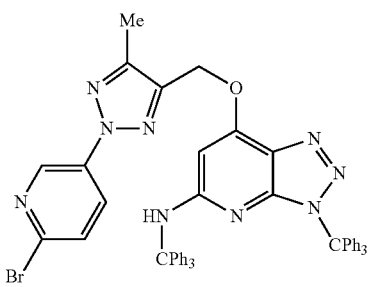

DIAD (0.24 mL, 1.2 mmol) was added to a solution of Intermediate 5 (38 mg, 0.61 mmol), Example 59A and triphenylphosphine (320 mg, 1.2 mmol) in THF (2 mL) at rt, and the solution was allowed to stir over night at rt. The reaction mixture was loaded directly on to a silica gel column and purified with 0-50% EtOAc/hexanes. The isolated brown oil was dissolved in small amount of DCM, and then MeOH was added to cause white ppt to form. Solvent removal formed a light brown solid (300 mg). MS (ESI) m/z 886/888.

Example 59

Example 59 was synthesized from Example 59B, and Intermediate 5 using General Route 5. MS (ESI) m/z 402.1 (M+H). $^1$H NMR (500 MHz, DMSO-d$_6$) δ 9.02 (br. s., 1H), 8.30 (d, J=8.5 Hz, 1H), 7.85 (d, J=8.5 Hz, 1H), 6.26 (br. s., 1H), 5.60 (br. s., 2H), 2.45 (s, 3H).

Example 60: 7-((5-Methyl-2-(6-(piperazin-1-yl)pyridin-3-yl)-2H-1,2,3-triazol-4-yl)methoxy)-3H-[1,2,3]triazolo[4,5-b]pyridin-5-amine

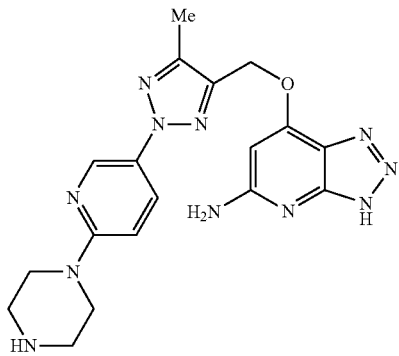 [SMILES: Cc1nn(-c2ccc(N3CCNCC3)nc2)nc1COc1cc(N)nc2[nH]nnc12]

Example 60A: (4-Methyl-2-phenyloxazol-5-yl)methanol

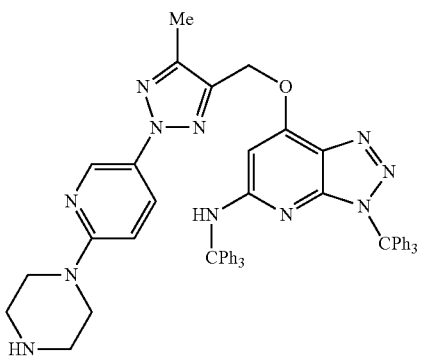

Example 59B (25 mg, 0.028 mmol) was added to a mixture of piperazine (4.9 mg, 0.056 mmol) and K$_2$CO$_3$ (12 mg, 0.085 mmol) in DMSO (0.30 mL). The reaction mixture was heated to 80° C. for 18 hrs in a sealed vessel. The reaction mixture was cooled to rt and diluted with EtOAc and water. The layers were separated, and the aqueous layer was adjusted to neutral pH and then extracted with EtOAc (3×). The combined extracts were washed with brine, dried over Na$_2$SO$_4$, and concentrated to give the Example 60A. MS (ESI) m/z 892.1 (M+H).

Example 60

Example 60 was synthesized from Example 60A and TFA using General Route 5. MS (ESI) m/z 408.2 (M+H). $^1$H NMR (500 MHz, DMSO-$d_6$) δ 8.71 (br. s., 1H), 8.10 (d, J=4.4 Hz, 1H), 7.95 (br. s., 1H), 7.01 (d, J=8.8 Hz, 1H), 6.56 (br. s., 2H), 6.14 (br. s., 1H), 5.49 (br. s., 2H), 3.00-2.83 (m, 5H), 2.73 (br. s., 2H), 2.41 (br. s., 3H), 1.90 (br. s., 1H).

Example 61: 4-(5-(4-(((5-Amino-3H-[1,2,3]triazolo[4,5-b]pyridin-7-yl)oxy)methyl)-5-methyl-2H-1,2,3-triazol-2-yl)pyridin-2-yl)piperazin-2-one

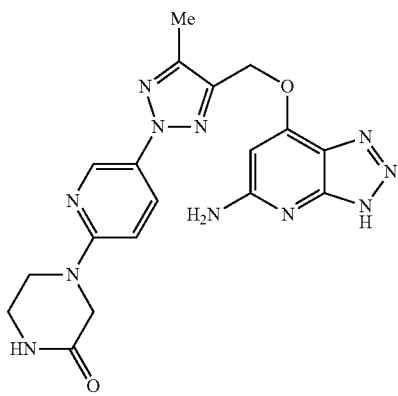 [SMILES: Cc1nn(-c2ccc(N3CCNC(=O)C3)nc2)nc1COc1cc(N)nc2[nH]nnc12]

Example 61 was synthesized from piperazin-2-one and Example 59B using a route similar to that described for Example 60. MS (ESI) m/z 422.1 (M+H). $^1$H NMR (500 MHz, DMSO-$d_6$) δ 8.73 (br. s., 1H), 8.20-8.07 (m, 2H), 6.98 (d, J=9.1 Hz, 1H), 6.49 (br. s., 2H), 6.11 (br. s., 1H), 5.50 (br. s., 2H), 4.06 (br. s., 2H), 3.79 (br. s., 2H), 2.41 (br. s., 3H).

Example 62: 7-((5-Methyl-2-(6-(methylamino)pyridin-3-yl)-2H-1,2,3-triazol-4-yl)methoxy)-3H-[1,2,3]triazolo[4,5-b]pyridin-5-amine

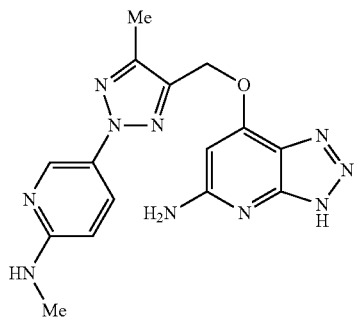 [SMILES: CNc1ccc(-n2nc(C)c(COc3cc(N)nc4[nH]nnc34)n2)cn1]

Example 62 was synthesized from methylamine and Example 59B using a route similar to that described for Example 60. MS (ESI) m/z 353.2 (M+H). $^1$H NMR (500 MHz, DMSO-$d_6$) δ 8.57 (br. s., 1H), 7.99-7.88 (m, 1H), 6.93 (br. s., 1H), 6.58 (d, J=8.8 Hz, 1H), 6.31 (br. s., 2H), 6.05 (br. s., 1H), 5.50 (br. s., 2H), 2.81 (br. s., 3H), 2.39 (br. s., 3H).

Example 63: 7-((5-Methyl-2-(4-(piperazin-1-yl)phenyl)-2H-1,2,3-triazol-4-yl)methoxy)-3H-[1,2,3]triazolo[4,5-b]pyridin-5-amine

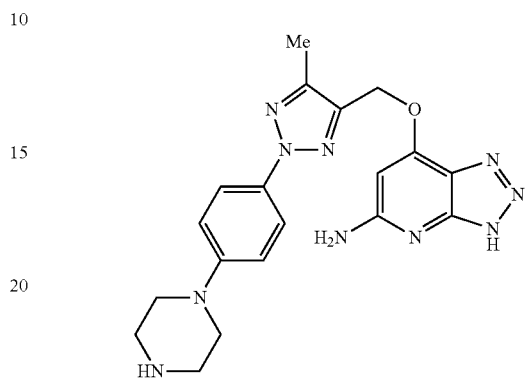

Example 63A: 7-((5-Methyl-2-(4-(piperazin-1-yl)phenyl)-2H-1,2,3-triazol-4-yl)methoxy)-N,3-ditrityl-3H-[1,2,3]triazolo[4,5-b]pyridin-5-amine

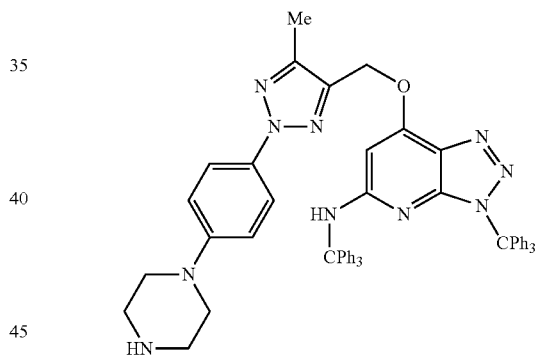

Example 59B (50 mg, 0.056 mmol), piperazine (5.8 mg, 0.068 mmol), sodium tert-butoxide (8.1 mg, 0.085 mmol), BINAP (1.1 mg, 1.7 μmol), and Pd$_2$(dba)$_3$ (0.52 mg, 0.56 μmol) were brought up in toluene (2.8 mL) in a sealed tube. The tube was purged with nitrogen, and the reaction mixture was stirred at 100° C. for 18 hrs. The mixture was diluted with 10 mL of DCM, washed with water and brine, dried over Na$_2$SO$_4$, and concentrated to give the crude product. MS (ESI) m/z 892 (M+H).

Example 63

Example 63 was synthesized from Example 63A and TFA using General Route 5. MS (ESI) m/z 407.25 (M+H). $^1$H NMR (500 MHz, DMSO-$d_6$) δ 8.74 (br. s., 2H), 7.87 (d, J=9.1 Hz, 2H), 7.15 (d, J=9.1 Hz, 2H), 6.17 (br. s., 1H), 5.50 (s, 2H), 3.25 (br. s., 6H), 2.89 (s, 1H), 2.73 (s, 1H), 2.41 (s, 3H).

Example 64: (5-(((5-Amino-3H-[1,2,3]triazolo[4,5-b]pyridin-7-yl)oxy)methyl)-2-phenyl-2H-1,2,3-triazol-4-yl)methanol

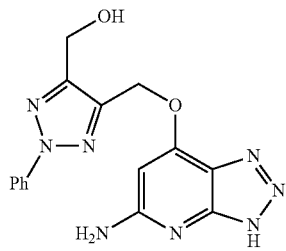 [SMILES: Nc1cc(OCc2nn(-c3ccccc3)nc2CO)c2nn[nH]c2n1]

Example 64A: Methyl 5-(hydroxymethyl)-2-phenyl-2H-1,2,3-triazole-4-carboxylate

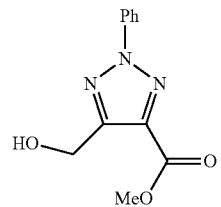

To a stirred solution of methyl 5-(methoxymethyl)-2-phenyl-2H-1,2,3-triazole-4-carboxylate (an intermediate prepared in Example 56) (150 mg, 0.61 mmol) in DCM (4.8 mL) at −78° C. was added BBr$_3$ (57 μl, 0.61 mmol) and the reaction mixture was stirred at −78° C. for 1 hour. The reaction mixture was quenched with saturated sodium bicarbonate solution and extracted with DCM (10 mL×2). The combined organic layers were dried over Na$_2$SO$_4$, filtered and concentrated. The crude product was purified by column chromatography (0-10% MeOH/DCM) to give the title compound (15 mg, 0.066 mmol). MS (ESI) m/z 216.0 (M+H—H$_2$O).

Example 64B: (2-Phenyl-5-(((3-trityl-5-(tritylamino)-3H-[1,2,3]triazolo[4,5-b]pyridin-7-yl)oxy)methyl)-2H-1,2,3-triazol-4-yl)methanol

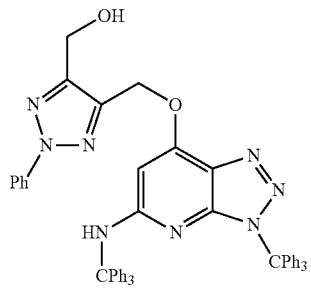

A solution of methyl 2-phenyl-5-(((3-trityl-5-(tritylamino)-3H-[1,2,3]triazolo [4,5-b]pyridin-7-yl)oxy)methyl)-2H-1,2,3-triazole-4-carboxylate (prepared from Example 64A and Intermediate 5 using procedures found in General Route 5) (50 mg, 0.059 mmol) in THF (1.0 mL) was cooled to −78° C. and to it was added LAH (4.5 mg, 0.12 mmol). After 2 hrs, the reaction was quenched with one drop of 1N NaOH, diluted with water (5 mL) and extracted with EtOAc (10 mL×2). The aqueous layer was brought to pH 7, and extracted once more with EtOAc. The combined extracts were washed with brine, dried over Na$_2$SO$_4$ and concentrated to give the crude product, (48 mg, 0.059 mmol).

Example 64

Example 64 was synthesized from Example 64B and TFA using procedures found in General Route 5. MS (ESI) m/z 339.1 (M+H). $^1$H NMR (500 MHz, DMSO-d$_6$) δ 8.03 (d, J=8.3 Hz, 2H), 7.59 (t, J=7.8 Hz, 2H), 7.49-7.41 (m, 1H), 6.56 (br. s., 2H), 6.16 (s, 1H), 5.58 (s, 2H), 4.76 (s, 2H).

Example 65: 5-(((5-Amino-3H-[1,2,3]triazolo[4,5-b]pyridin-7-yl)oxy)methyl)-2-phenyl-2H-1,2,3-triazole-4-carbonitrile

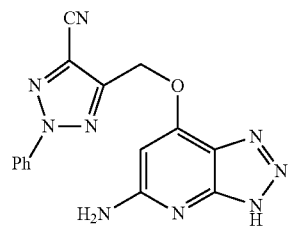 [SMILES: N#Cc1nn(-c2ccccc2)nc1COc1cc(N)nc2[nH]nnc12]

Example 65A: 2-Phenyl-5-(((3-trityl-5-(tritylamino)-3H-[1,2,3]triazolo[4,5-b]pyridin-7-yl)oxy)methyl)-2H-1,2,3-triazole-4-carboxamide

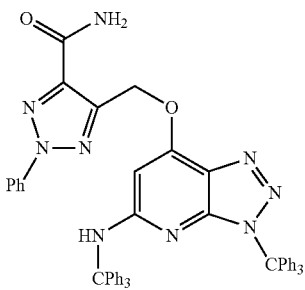

A solution of methyl 2-phenyl-5-(((3-trityl-5-(tritylamino)-3H-[1,2,3]triazolo [4,5-b]pyridin-7-yl)oxy)methyl)-2H-1,2,3-triazole-4-carboxylate (prepared from Example 64A and Intermediate 5 using procedures found in General Route 5) (120 mg, 0.14 mmol) in 7 N NH$_3$ in MeOH (2.0 mL) was heated to 80° C. in a sealed vial overnight. The reaction mixture was concentrated and purified by column chromatography (0-100% EtOAc/hexanes) to give the title compound, (19 mg, 0.023 mmol). MS (ESI) m/z 836.4 (M+H).

To a solution of Example 65A (30 mg, 0.036 mmol) in DCM (0.50 mL) at 0° C. was added pyridine (2.9 μL, 0.036 mmol), followed by TFAA (10 μL, 0.072 mmol). The reaction was stirred at rt overnight, and then TFA (0.30 mL)

was added. After 10 mins, a few drops of EtSiH were added to the reaction mixture and concentrated. The crude material was purified via preparative LC/MS with the following conditions: Column: Waters XBridge C18, 19×100 mm, 5-μm particles; Mobile Phase A: 5:95 Acn:water with 10-mM ammonium acetate; Mobile Phase B: 95:5 Acn:water with 10-mM ammonium acetate; Gradient: 10-50% B over 10 minutes, then a 5-minute hold at 100% B; Flow: 20 mL/min. Fractions containing the desired product were combined and dried via centrifugal evaporation to give the title compound (0.8 mg, 2.1 μmol). MS (ESI) m/z 334.0 (M+H). $^1$H NMR (500 MHz, DMSO-$d_6$) δ 8.09 (d, J=7.4 Hz, 2H), 7.65 (d, J=7.2 Hz, 3H), 6.56 (br. s., 1H), 6.11 (br. s., 1H), 5.82 (br. s., 2H).

Example 66: 7-((2-Benzyl-5-methyl-2H-1,2,3-triazol-4-yl)methoxy)-3H-[1,2,3]triazolo [4,5-b]pyridin-5-amine

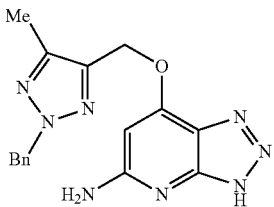 [SMILES: Cc1nn(Cc2ccccc2)nc1COc1cc(N)nc2[nH]nnc12]

Example 66A: Ethyl 5-methyl-2H-1,2,3-triazole-4-carboxylate

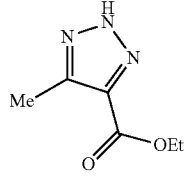 [SMILES: CCOC(=O)c1n[nH]nc1C]

To a solution of 5-methyl-2H-1,2,3-triazole-4-carboxylic acid (670 mg, 5.3 mmol) in EtOH (10 mL) at rt was added SOCl$_2$ (0.39 mL, 5.3 mmol). The reaction mixture was heated to 80° C. for 18 hrs. The reaction solution was diluted with EtOAc and water. The layers were separated, and the aqueous layer was extracted with EtOAc (3×). The combined extracts were washed with saturated aqueous NaHCO$_3$ and brine, dried over Na$_2$SO$_4$, and concentrated to give the title product (650 mg, 4.2 mmol, 80% yield) as a white powder. MS (ESI) m/z 156.0 (M+H).

Example 66B: Ethyl 2-benzyl-5-methyl-2H-1,2,3-triazole-4-carboxylate

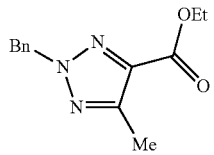

To a solution of Example 66A (110 mg, 0.73 mmol) and K$_2$CO$_3$ (220 mg, 1.6 mmol) in DMF (3.0 mL), was added (bromomethyl)benzene (140 mg, 0.81 mmol). The reaction mixture was stirred at rt for 18 hrs. The reaction mixture was diluted with EtOAc and water. The layers were separated, and the aqueous layer was extracted with EtOAc (3×). The combined extracts were washed with brine, dried over Na$_2$SO$_4$, and concentrated. The crude product was purified by column chromatography (4 g SiO$_2$, 15 mins, 0-50% EtOAc/hexanes). MS (ESI) m/z 246.1 (M+H). $^1$H NMR (400 MHz, CDCl$_3$) δ 7.39-7.32 (m, 5H), 5.57 (s, 2H), 4.42 (q, J=7.0 Hz, 2H), 2.51 (s, 3H), 1.42 (t, J=7.2 Hz, 3H).

Example 66

Example 66 was synthesized from (2-benzyl-5-methyl-2H-1,2,3-triazol-4-yl)methanol (obtained from Example 66B in a route similar to that described in preparing Example 10C) and Intermediate 5 using General Route 5. MS (ESI) m/z 336.9 (M+H). $^1$H NMR (500 MHz, DMSO-$d_6$) δ 7.41-7.25 (m, 5H), 6.53 (br. s., 2H), 6.07 (br. s., 1H), 5.57 (s, 2H), 5.38 (br. s., 2H), 2.28 (s, 3H).

Example 67: 7-((2-Cyclopentyl-5-methyl-2H-1,2,3-triazol-4-yl)methoxy)-3H-[1,2,3]triazolo[4,5-b]pyridin-5-amine

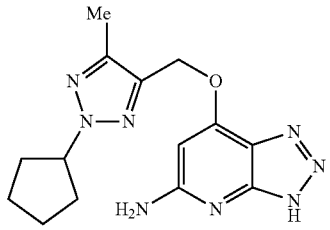 [SMILES: Cc1nn(C2CCCC2)nc1COc1cc(N)nc2[nH]nnc12]

Example 67 was synthesized from bromocyclopentane and Example 66A in a route similar to that described in preparing Example 66. MS (ESI) m/z 315.2 (M+H). $^1$H NMR (500 MHz, DMSO-$d_6$) δ 6.51 (br. s., 1H), 6.08 (br. s., 1H), 5.36 (s, 2H), 5.01-4.89 (m, 1H), 2.28 (s, 3H), 2.12 (dd, J=7.0, 6.2 Hz, 2H), 2.06-2.00 (m, 2H), 1.86-1.74 (m, 2H), 1.72-1.61 (m, 2H).

Example 68: 7-((5-Methyl-2-(piperidin-4-yl)-2H-1,2,3-triazol-4-yl)methoxy)-3H-[1,2,3]triazolo[4,5-b]pyridin-5-amine

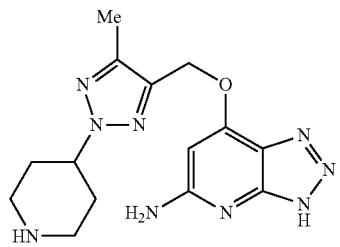 [SMILES: Cc1nn(C2CCNCC2)nc1COc1cc(N)nc2[nH]nnc12]

Example 68 was synthesized from tert-butyl 4-bromopiperidine-1-carboxylate and Example 66A in a route similar to that described in preparing Example 66. MS (ESI) m/z 330.20 (M+H). $^1$H NMR (500 MHz, DMSO-$d_6$) δ 6.49 (s, 2H), 6.09 (s, 1H), 5.36 (s, 2H), 4.56-4.50 (m, 1H), 3.09 (d, J=12.7 Hz, 2H), 2.72-2.66 (m, 2H), 2.29 (s, 3H), 2.06 (d, J=11.3 Hz, 2H), 1.95-1.86 (m, 2H).

Example 69: 7-((5-Methyl-2-(pyrrolidin-3-ylmethyl)-2H-1,2,3-triazol-4-yl)methoxy)-3H-[1,2,3]triazolo[4,5-b]pyridin-5-amine

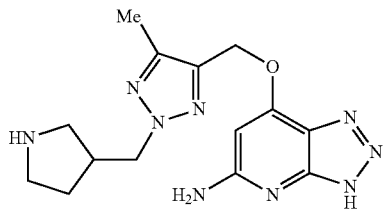 [SMILES: Cc1nn(CC2CCNC2)nc1COc1cc(N)nc2[nH]nnc12]

Example 69 was synthesized from tert-butyl 3-(bromomethyl)pyrrolidine-1-carboxylate and Example 66A in a route similar to that described in preparing Example 66. MS (ESI) m/z 330.1 (M+H). $^1$H NMR (400 MHz, CD$_3$OD) δ 6.52 (s, 1H), 5.56 (s, 2H), 4.61-4.45 (m, 2H), 3.52-3.38 (m, 2H), 3.29-3.09 (m, 2H), 3.06-2.91 (m, 1H), 2.39 (s, 3H), 2.27-2.14 (m, J=13.1, 5.2 Hz, 1H), 1.92-1.78 (m, 1H).

Example 70: 7-((2-((1R,4R)-4-Aminocyclohexyl)-5-methyl-2H-1,2,3-triazol-4-yl)methoxy)-3H-[1,2,3]triazolo[4,5-b]pyridin-5-amine

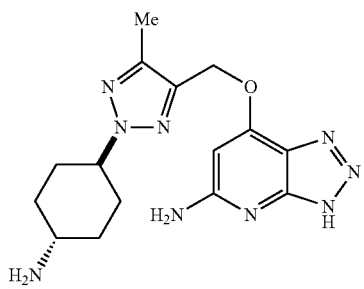

Example 70A: Ethyl 2-((1R,4R)-4-((tert-butoxycarbonyl)amino)cyclohexyl)-5-methyl-2H-1,2,3-triazole-4-carboxylate

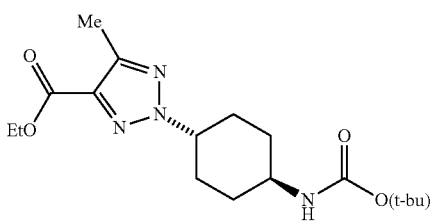

To a solution of Example 66A (40 mg, 0.26 mmol), tert-butyl ((1S,4S)-4-hydroxycyclohexyl)carbamate (67 mg, 0.31 mmol), and triphenylphosphine (140 mg, 0.52 mmol) in THF (2.0 mL) was added DIAD (0.10 mL, 0.52 mmol). The reaction solution was allowed to stir for 18 hrs at rt. The reaction solution was concentrated and purified by column chromatography (0-100% gradient, EtOAc/hexanes) to obtain Example 70A (50 mg, 0.14 mmol). MS (ESI) m/z 353.1 (M+H).

Example 70

Example 70 was synthesized from Example 70A in a route similar to that described in preparing Example 66. MS (ESI) m/z 344.20 (M+H). $^1$H NMR (500 MHz, DMSO-d$_6$) δ 6.43 (br. s., 1H), 6.07 (s, 1H), 5.35 (s, 2H), 4.38 (t, J=11.4 Hz, 1H), 2.78-2.66 (m, 1H), 2.30-2.24 (m, 3H), 2.08 (d, J=12.7 Hz, 2H), 1.93-1.76 (m, 6H), 1.27 (q, J=12.3 Hz, 2H).

Example 71: 7-((2-((1H-Imidazol-4-yl)methyl)-5-methyl-2H-1,2,3-triazol-4-yl)methoxy)-3H-[1,2,3]triazolo[4,5-b]pyridin-5-amine

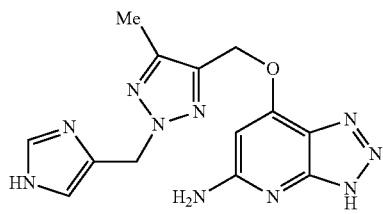 [SMILES: Cc1nn(Cc2c[nH]cn2)nc1COc1cc(N)nc2[nH]nnc12]

Example 71 was synthesized from tert-butyl 4-(chloromethyl)-1H-imidazole-1-carboxylate and Example 66A in a route similar to that described in preparing Example 66. MS (ESI) m/z 327.2 (M+H). $^1$H NMR (500 MHz, DMSO-d$_6$) δ 9.04 (s, 1H), 7.80 (s, 1H), 6.19 (br. s., 1H), 5.73 (s, 2H), 5.42 (s, 2H), 2.32 (s, 3H).

Example 72: 7-((5-Methyl-2-(3-methylcyclopentyl)-2H-1,2,3-triazol-4-yl)methoxy)-3H-[1,2,3]triazolo[4,5-b]pyridin-5-amine

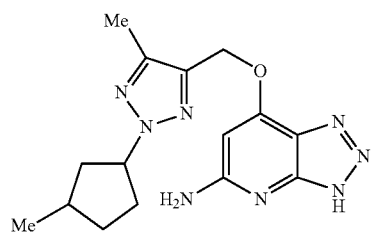 [SMILES: Cc1nn(C2CCC(C)C2)nc1COc1cc(N)nc2[nH]nnc12]

Example 72 was synthesized as a diastereomeric mixture from 3-methylcyclopentanol and Example 66A in a route similar to that described in preparing Example 70. MS (ESI) m/z 329.20 (M+H). $^1$H NMR (500 MHz, DMSO-d$_6$) δ 6.23 (br. s., 1H), 5.39 (s, 2H), 5.04-4.92 (m, 1H), 2.39-2.30 (m, 1H), 2.28 (s, 3H), 2.26-2.01 (m, 3H), 2.00-1.79 (m, 1H), 1.74-1.62 (m, 1H), 1.45-1.18 (m, 1H), 1.07-0.99 (m, 3H).

Example 73: 7-((5-Methyl-2-(((2S,4S)-4-phenoxy-pyrrolidin-2-yl)methyl)-2H-1,2,3-triazol-4-yl)methoxy)-3H-[1,2,3]triazolo[4,5-b]pyridin-5-amine

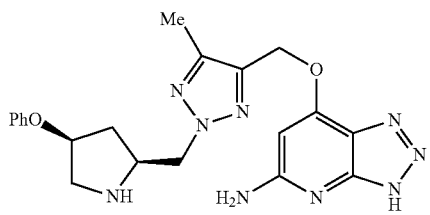 [SMILES: Cc1nn(C[C@@H]2C[C@H](Oc3ccccc3)CN2)nc1COc1cc(N)nc2[nH]nnc12]

Example 73A: (2S,4S)-tert-Butyl 2-(hydroxymethyl)-4-phenoxypyrrolidine-1-carboxylate

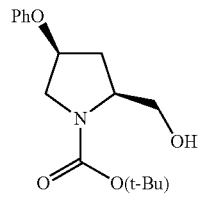

To a solution of (2S,4S)-1-(tert-butoxycarbonyl)-4-phenoxypyrrolidine-2-carboxylic acid (200 mg, 0.65 mmol) and N-methylmorpholine (110 µL, 0.98 mmol) in THF (6.5 mL) at 0° C. was added isobutyl chloroformate (100 µL, 0.78 mmol). The reaction mixture was stirred for 5 minutes before sodium borohydride (98 mg, 2.6 mmol) dissolved in 5 mL of water was added portionwise. The reaction mixture was allowed to warm to rt and stir over night. The reaction was quenched with saturated ammonium chloride and extracted with EtOAc (3×). The combined organics were washed with brine, dried with sodium sulfate, filtered and concentrated to yield the title compound as a clear oil (190 mg, 0.65 mmol). (ESI) m/z 238.1 (M-tBu+H).

Example 73

Example 73 was synthesized from Example 73A and Example 66A in a route similar to that described in preparing Example 70. MS (ESI) m/z 422.2 (M+H).

Example 74: 7-((5-Methyl-2-((5-phenylpyrrolidin-3-yl)methyl)-2H-1,2,3-triazol-4-yl)methoxy)-3H-[1,2,3]triazolo[4,5-b]pyridin-5-amine (Single Diastereomer, Undetermined Stereochemistry)

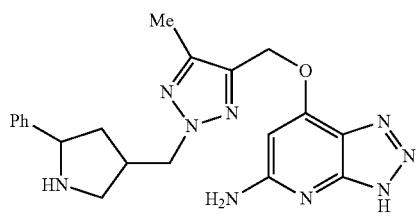 [SMILES: Cc1nn(CC2CNC(c3ccccc3)C2)nc1COc1cc(N)nc2[nH]nnc12]

Example 74 was prepared from Example 66A and tert-butyl 4-(hydroxymethyl)-2-phenylpyrrolidine-1-carboxylate (prepared from 1-(tert-butoxycarbonyl)-5-phenylpyrrolidine-3-carboxylic acid in a manner similar to Example 73A) in a route similar to that described in preparing Example 70. MS (ESI) m/z 406.2 (M+H). $^1$H NMR (400 MHz, CD$_3$OD) δ 7.51-7.40 (m, 5H), 6.45 (s, 1H), 5.54 (s, 2H), 4.74 (dd, J=12.2, 6.1 Hz, 1H), 4.70-4.58 (m, 2H), 3.67-3.55 (m, 1H), 3.46-3.36 (m, 1H), 3.27-3.16 (m, 1H), 2.63-2.53 (m, 1H), 2.39 (s, 3H), 2.20-2.02 (m, 1H).

Example 75: 7-((5-Methyl-2-((5-phenylpyrrolidin-3-yl)methyl)-2H-1,2,3-triazol-4-yl)methoxy)-3H-[1,2,3]triazolo[4,5-b]pyridin-5-amine (Enantiomer 1, Stereochemistry Unknown)

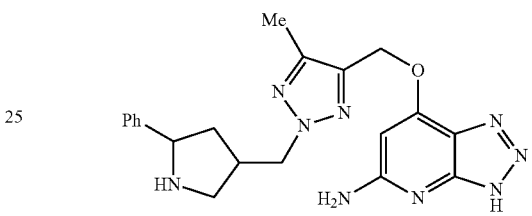

Example 75 was obtained by the chiral separation of the diastereomer Example 74 using SFC (column: Regis WHELK-O® 1, 30×250 mm, 5µ. Mobile Phase: 45% EtOH: DEA/55% CO$_2$. Flow conditions: 80 mL/min, 150 Bar, 40° C. Detector Wavelength: 220 nm. Injection Details: 0.75 mL of 22 mg/mL in EtOH). Two peaks collected in ethanol:DEA (0.1%). The first eluting peak (rt=6.54 mins) was collected as the title compound, in >99% ee.

Example 76: 7-((5-Methyl-2-((5-phenylpyrrolidin-3-yl)methyl)-2H-1,2,3-triazol-4-yl)methoxy)-3H-[1,2,3]triazolo[4,5-b]pyridin-5-amine (Enantiomer 2, Stereochemistry Unknown)

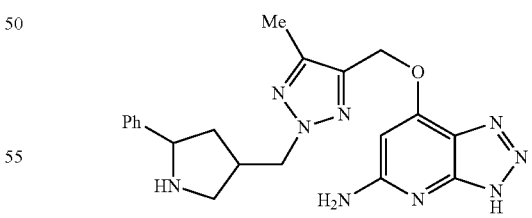

Example 76 was obtained by the chiral separation of the diastereomer Example 74 using SFC (column: Regis WHELK-O® 1, 30×250 mm, 5µ. Mobile Phase: 45% EtOH: DEA/55% CO$_2$. Flow conditions: 80 mL/min, 150 Bar, 40° C. Detector Wavelength: 220 nm. Injection Details: 0.75 mL of 22 mg/mL in EtOH). Two peaks collected in ethanol:DEA (0.1%). The second eluting peak (rt=11.44) was collected as the title compound, in 89% ee.

Example 77: 7-((5-Methyl-2-(3-(pyrrolidin-3-yl)benzyl)-2H-1,2,3-triazol-4-yl)methoxy)-3H-[1,2,3]triazolo[4,5-b]pyridin-5-amine

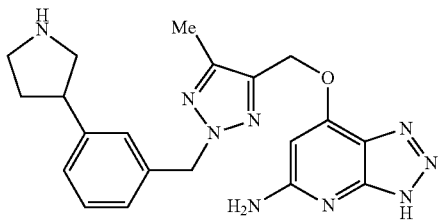 [SMILES: Cc1nn(Cc2cccc(C3CCNC3)c2)nc1COc1cc(N)nc2[nH]nnc12]

Example 77 was prepared from Example 66A and tert-butyl 3-(3-(hydroxymethyl)phenyl)pyrrolidine-1-carboxylate (prepared from 3-(1-(tert-butoxycarbonyl)pyrrolidin-3-yl)benzoic acid in a manner similar to Example 73A) in a route similar to that described in preparing Example 70. MS (ESI) m/z 406.25 (M+H). $^1$H NMR (500 MHz, DMSO-d$_6$) δ 7.33-7.18 (m, 3H), 7.12 (d, J=7.2 Hz, 1H), 6.48 (br. s., 2H), 6.09 (s, 1H), 5.54 (br. s., 2H), 5.38 (s, 2H), 3.37-3.31 (m, 1H), 3.24-3.09 (m, 2H), 3.05-2.98 (m, 1H), 2.80-2.75 (m, 1H), 2.29 (s, 3H), 2.19 (d, J=5.0 Hz, 1H), 1.89 (s, 2H), 1.74 (dt, J=19.3, 9.9 Hz, 1H).

Example 78: 7-((5-Methyl-2-(3-(piperidin-4-yl)benzyl)-2H-1,2,3-triazol-4-yl)methoxy)-3H-[1,2,3]triazolo[4,5-b]pyridin-5-amine

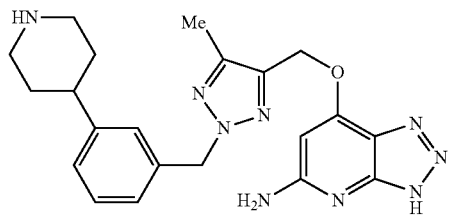 [SMILES: Cc1nn(Cc2cccc(C3CCNCC3)c2)nc1COc1cc(N)nc2[nH]nnc12]

Example 78A: Methyl 3-(piperidin-4-yl)benzoate

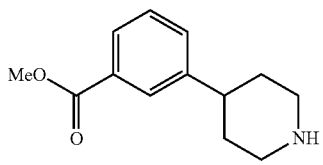

A solution of 3-(piperidin-4-yl)benzoic acid (480 mg, 2.3 mmol) and sulfuric acid (0.10 mL, 1.9 mmol) in MeOH (10 mL) was stirred at reflux over the weekend. After evaporation of the solvent, the residue was dissolved in 1N NaOH (to ensure basic conditions) and extracted with EtOAc (3×). The combined extracts were dried over sodium sulfate and evaporated to give the title compound as a colorless oil (470 mg, 2.1 mmol). MS (ESI) m/z 219.9 (M+H).

Example 78B: tert-Butyl 4-(3-(methoxycarbonyl)phenyl)piperidine-1-carboxylate

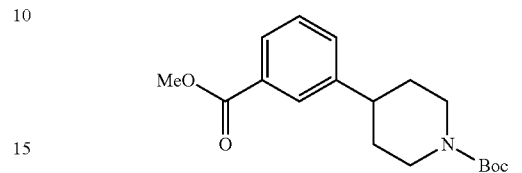

A solution of Example 78A (470 mg, 2.1 mmol) in THF (5.0 mL) was treated with DIEA (0.93 mL, 5.3 mmol) and di-tert-butyl dicarbonate (540 mg, 2.5 mmol). The mixture was stirred at rt overnight. The reaction mixture was washed with brine and dried over Na$_2$SO$_4$. The solvent was removed and the crude product was purified by column chromatography (12 g SiO$_2$, 0-100% EtOAc/hex) to give the title compound as a colorless oil (600 mg, 1.9 mmol). MS (ESI) m/z 319.9 (M+H). $^1$H NMR (500 MHz, CDCl$_3$) δ 7.92-7.85 (m, 2H), 7.42-7.33 (m, 2H), 4.37-4.14 (m, 2H), 3.94-3.84 (m, 3H), 2.88-2.75 (m, 2H), 2.74-2.66 (m, 1H), 1.87-1.78 (m, 2H), 1.70-1.59 (m, 2H), 1.49 (s, 9H).

Example 78C: tert-Butyl 4-(3-(hydroxymethyl)phenyl)piperidine-1-carboxylate

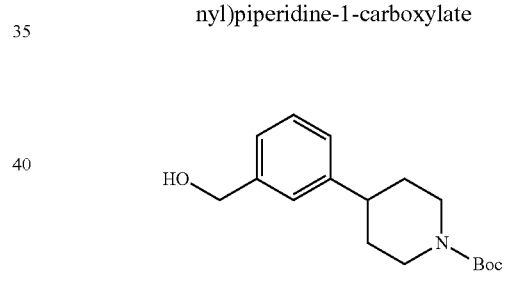

To a cooled (0° C.) solution of Example 78B (600 mg, 1.9 mmol) in THF (9.4 mL) under argon, was added a solution of LiBH$_4$ in THF (1.9 mL, 3.8 mmol) dropwise. The reaction solution was stirred for 1 h at 0° C., then overnight at rt. The reaction solution was cooled to 0° C. and the pH of the solution was adjusted to pH 1 with 1 M HCl. The reaction solution was stirred for 30 mins, then adjusted to pH 9-10 with K$_2$CO$_3$. The reaction solution was extracted with EtOAc (2×). The combined extracts were washed with brine, dried over Na$_2$SO$_4$, filtered and evaporated to give the title compound as a colorless oil (540 mg, 0.92 mmol). MS (ESI) m/z 236.0 (M-tBu+H).

Example 78

Example 78 was synthesized from Example 78C and Example 66A in a route similar to that described in preparing Example 70. MS (ESI) m/z 420.3 (M+H). $^1$H NMR (500 MHz, DMSO-d$_6$) δ 8.67 (br. s., 1H), 8.38 (br. s., 1H), 7.39-7.28 (m, 1H), 7.20-7.13 (m, 3H), 6.20 (br. s., 1H), 5.57 (s, 2H), 5.40 (s, 2H), 3.36 (d, J=11.8 Hz, 2H), 2.99 (q, J=11.7

Hz, 2H), 2.86-2.77 (m, 1H), 2.29 (s, 3H), 1.91 (br. s., 2H), 1.82-1.67 (m, 2H), 1.08 (d, J=6.3 Hz, 1H).

Example 79: 7-((5-Methyl-2-(3-(piperidin-4-ylmethyl)benzyl)-2H-1,2,3-triazol-4-yl)methoxy)-3H-[1,2,3]triazolo[4,5-b]pyridin-5-amine

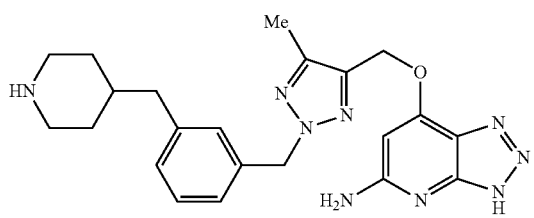 [SMILES: Cc1nn(Cc2cccc(CC3CCNCC3)c2)nc1COc1cc(N)nc2[nH]nnc12]

Example 79 was synthesized from methyl 3-(piperidin-4-ylmethyl)benzoate in a route similar to that described in preparing Example 78. MS (ESI) m/z 434.3 (M+H).

Example 80: 7-((2-Benzyl-5-(trifluoromethyl)-2H-1,2,3-triazol-4-yl)methoxy)-3H-[1,2,3]triazolo[4,5-b]pyridin-5-amine

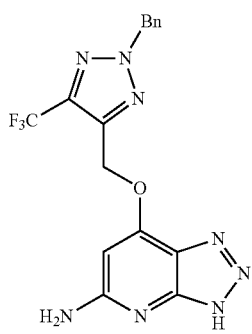 [SMILES: Nc1cc(OCc2nn(Cc3ccccc3)nc2C(F)(F)F)c2nn[nH]c2n1]

Example 80A: 1-(Azidomethyl)-4-methoxybenzene

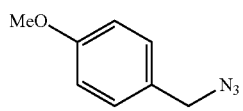

To a solution of 1-(bromomethyl)-4-methoxybenzene (1.0 g, 5.0 mmol) in DMF (20 mL) was added NBu$_4$Cl (0.025 g, 0.090 mmol) and NaN$_3$ (0.42 g, 6.5 mmol). The reaction mixture was stirred at rt for 3 h. The reaction solution was diluted with EtOAc and washed with water (3×), followed by brine, and then dried over Na$_2$SO$_4$ and concentrated. The crude product was purified by column chromatography (40 g SiO$_2$, 0-100% EtOAc/hexanes, 20 mins) to give the title compound (730 mg, 4.5 mmol). $^1$H NMR (400 MHz, CDCl$_3$) δ 7.29-7.24 (m, 2H), 6.92 (d, J=8.6 Hz, 2H), 4.28 (s, 2H), 3.83 (s, 3H).

Example 80B: Ethyl 1-(4-methoxybenzyl)-5-(trifluoromethyl)-1H-1,2,3-triazole-4-carboxylate, and Ethyl 1-(4-methoxybenzyl)-4-(trifluoromethyl)-1H-1,2,3-triazole-5-carboxylate

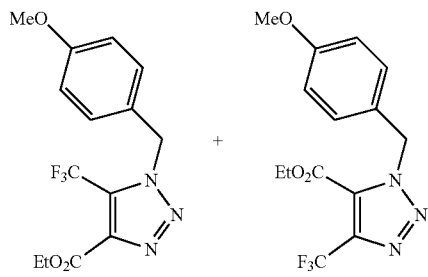 [SMILES: CCOC(=O)c1nnn(Cc2ccc(OC)cc2)c1C(F)(F)F ; CCOC(=O)c1c(C(F)(F)F)nnn1Cc1ccc(OC)cc1]

A solution of ethyl 4,4,4-trifluorobut-2-ynoate (44 mg, 0.26 mmol) and Example 80A (43 mg, 0.26 mmol) in toluene (3.0 mL) was heated to 95° C. in a sealed tube for 3 hrs. The reaction mixture was concentrated and purified by column chromatography (4 g SiO$_2$, 0-100% EtOAc/hexanes, 15 mins) to give the title compound (87 mg, 0.26 mmol). MS (ESI) m/z 330 (M+H).

Example 80C: Ethyl 5-(trifluoromethyl)-1H-1,2,3-triazole-4-carboxylate

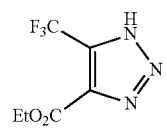 [SMILES: CCOC(=O)c1nn[nH]c1C(F)(F)F]

A solution of Example 80B (87 mg, 0.26 mmol) in TFA (2.0 mL) was heated to 60° C. for 4 h. The reaction mixture was concentrated, and then diluted with water and EtOAc. The layers were separated, and the organics were washed with saturated aqueous NaHCO$_3$, followed by brine, dried over Na$_2$SO$_4$ and concentrated to give the title product (55 mg, 0.26 mmol). MS (ESI) m/z 210.0 (M+H).

Example 80

Example 80 was synthesized from Example 80C and (bromomethyl)benzene in a route similar to that described in preparing Example 66. MS (ESI) m/z 391.15 (M+H). $^1$H NMR (500 MHz, DMSO-d$_6$) δ 7.43-7.31 (m, 6H), 6.94 (d, J=8.5 Hz, 1H), 6.12 (br. s., 1H), 5.81 (s, 2H), 5.72 (s, 1H), 5.57 (s, 2H).

Example 81: 7-((5-Bromo-2-methoxypyridin-3-yl)methoxy)-3H-[1,2,3]triazolo[4,5-b]pyridin-5-amine

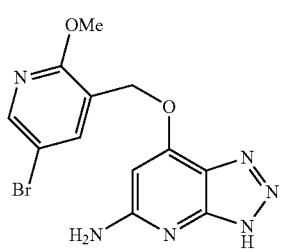 [SMILES: COc1ncc(Br)cc1COc1cc(N)nc2[nH]nnc12]

Example 81 was synthesized from Intermediate 4 and (5-bromo-2-methoxypyridin-3-yl)methanol via General Route 3. MS (ESI) m/z 353 (M+H).

Example 82: 7-((5-(Trifluoromethyl)furan-2-yl)methoxy)-3H-[1,2,3]triazolo[4,5-b]pyridin-5-amine

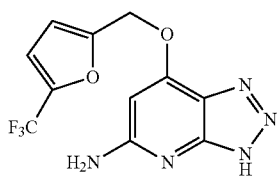 [SMILES: Nc1cc(OCc2ccc(C(F)(F)F)o2)c2nn[nH]c2n1]

Example 82 was synthesized from Intermediate 4 and (5-(trifluoromethyl) furan-2-yl)methanol using General Route 3. MS (ESI) m/z 300 (M+H).

Example 84: 7-((1-(Pyrimidin-2-yl)piperidin-4-yl)methoxy)-3H-[1,2,3]triazolo[4,5-b]pyridin-5-amine

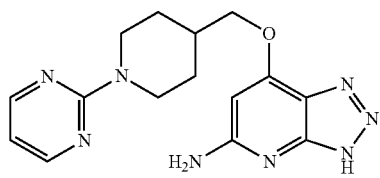 [SMILES: Nc1cc(OCC2CCN(c3ncccn3)CC2)c2nn[nH]c2n1]

Example 84 was synthesized from Intermediate 4 and (1-(pyrimidin-2-yl)piperidin-4-yl)methanol using General Route 3. MS (ESI) m/z 327 (M+H).

Example 85: 7-((1-(1,6-Dihydropyrimidin-2-yl)piperidin-4-yl)methoxy)-3H-[1,2,3]triazolo[4,5-b]pyridin-5-amine

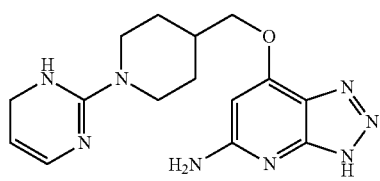 [SMILES: Nc1cc(OCC2CCN(C3=NC=CCN3)CC2)c2nn[nH]c2n1]

Example 85 was a side-product that formed during the Reduction Step of the synthesis of Example 84. MS (ESI) m/z 329 (M+H).

Example 86: 7-((1-(Methylsulfonyl)piperidin-2-yl)methoxy)-3H-[1,2,3]triazolo[4,5-b]pyridin-5-amine

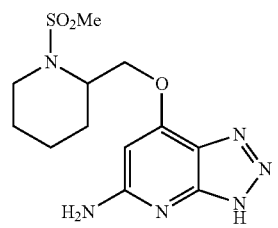 [SMILES: CS(=O)(=O)N1CCCCC1COc1cc(N)nc2[nH]nnc12]

Example 86 was synthesized from Intermediate 4 and (1-(methylsulfonyl) piperidin-2-yl)methyl methanesulfonate using General Route 3. MS (ESI) m/z 327 (M+H).

Example 87: 7-((5-Bromo-3-fluoropyridin-2-yl)methoxy)-3H-[1,2,3]triazolo[4,5-b]pyridin-5-amine

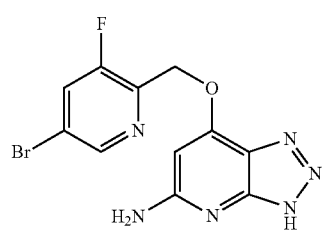 [SMILES: Nc1cc(OCc2ncc(Br)cc2F)c2nn[nH]c2n1]

Example 87 was synthesized from Intermediate 5 and (5-bromo-3-fluoropyridin-2-yl)methanol using General Route 5. MS (ESI) m/z 340 (M+H).

Example 88: 7-((2-Chloro-5-fluoropyridin-4-yl)methoxy)-3H-[1,2,3]triazolo[4,5-b]pyridin-5-amine

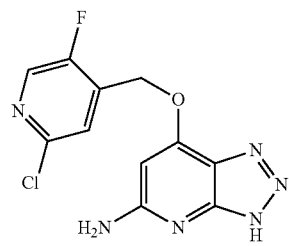 [SMILES: Nc1cc(OCc2cc(Cl)ncc2F)c2nn[nH]c2n1]

Example 88 was synthesized using Intermediate 5 and (2-chloro-5-fluoropyridin-4-yl)methanol using General Route 5. MS (ESI) m/z 295 (M+H).

Example 89: 7-((3-Fluoropyridin-2-yl)methoxy)-3H-[1,2,3]triazolo[4,5-b]pyridin-5-amine

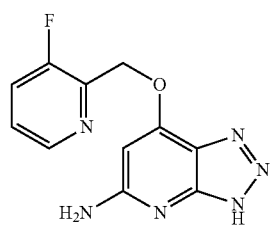 [SMILES: Nc1cc(OCc2ncccc2F)c2nn[nH]c2n1]

Example 89 was synthesized using Intermediate 5 and (3-fluoropyridin-2-yl)methanol using General Route 5. MS (ESI) m/z 261 (M+H).

Example 90: 7-((2-Chloropyridin-3-yl)methoxy)-
3H-[1,2,3]triazolo[4,5-b]pyridin-5-amine

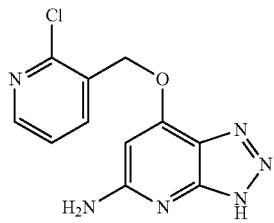 [SMILES: Nc1cc(OCc2cccnc2Cl)c2nn[nH]c2n1]

Example 90 was synthesized using Intermediate 5 and (2-chloropyridin-3-yl)methanol using General Route 5. MS (ESI) m/z 277 (M+H).

Example 91: 7-((4-Chloropyridin-3-yl)methoxy)-
3H-[1,2,3]triazolo[4,5-b]pyridin-5-amine

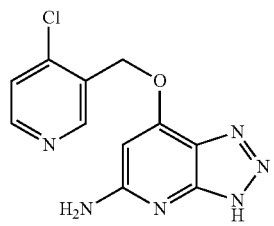 [SMILES: Nc1cc(OCc2cnccc2Cl)c2nn[nH]c2n1]

Example 91 was synthesized using Intermediate 5 and (4-chloropyridin-3-yl)methanol using General Route 5. MS (ESI) m/z 277 (M+H).

Example 92: 7-((5-Bromopyridin-2-yl)methoxy)-
3H-[1,2,3]triazolo[4,5-b]pyridin-5-amine

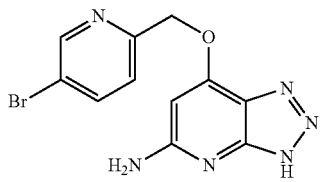 [SMILES: Nc1cc(OCc2ccc(Br)cn2)c2nn[nH]c2n1]

Example 92 was synthesized using Intermediate 5 and (5-bromopyridin-2-yl)methanol using General Route 5. MS (ESI) m/z 321 (M+H).

Example 93: 7-((5-Bromo-1-methyl-1H-pyrazol-3-yl)methoxy)-3H-[1,2,3]triazolo[4,5-b]pyridin-5-amine

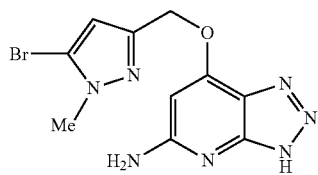 [SMILES: Cn1nc(COc2cc(N)nc3[nH]nnc23)cc1Br]

Example 93 was synthesized using Intermediate 5 and (5-bromo-1-methyl-1H-pyrazol-3-yl)methanol using General Route 5. MS (ESI) m/z 325 (M+H).

Example 95: 7-((6-Bromo-3-fluoropyridin-2-yl)methoxy)-3H-[1,2,3]triazolo[4,5-b]pyridin-5-amine

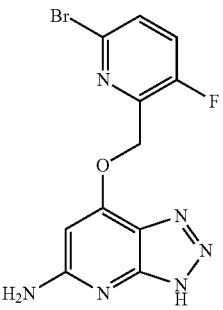 [SMILES: Nc1cc(OCc2nc(Br)ccc2F)c2nn[nH]c2n1]

Example 95A: 7-((6-Bromo-3-fluoropyridin-2-yl)methoxy)-N,3-ditrityl-3H-[1,2,3]triazolo[4,5-b]pyridin-5-amine

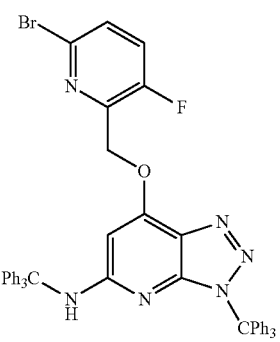

Example 95A and Example 95 was synthesized from on Intermediate 5 with (6-bromo-3-fluoropyridin-2-yl)methanol using General Route 5. MS (ESI) m/z 338 (M+H).

Example 96: 7-((3-Fluoro-6-(1-methyl-1H-pyrazol-3-yl)pyridin-2-yl)methoxy)-3H-[1,2,3]triazolo[4,5-b]pyridin-5-amine

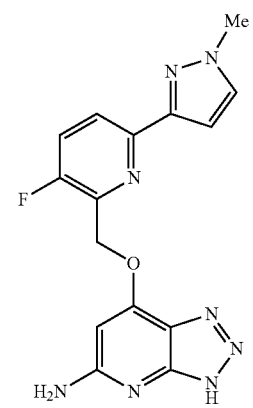 [SMILES: Cn1ccc(-c2ccc(F)c(COc3cc(N)nc4[nH]nnc34)n2)n1]

To a vial with a septum cap were added Example 95A (50 mg, 0.061 mmol), (1-methyl-1H-pyrazol-3-yl)boronic acid (8 mg, 0.061 mmol), K$_2$CO$_3$ (17 mg, 0.12 mmol), and tetrakis(triphenylphosphine)palladium(0) (7 mg, 6.1 μmol). The vial was evacuated and back-filled with argon three times. Degassed DMF (2.7 mL) and water (0.3 mL) were added. The reaction mixture was stirred at 90° C. for 1.5 h. The crude reaction was then diluted with DCM (4 mL), filtered, and used as such in the next reaction. To the above solution was added TFA (1 mL) to produce a bright yellow solution. After 1 minute, triethylsilane (20 μL, 120 mmol) was added and the reaction mixture was concentrated in vacuo. The crude product was purified by prep HPLC to yield Example 96 (1.9 mg, 9% yield over 2 steps). MS (ESI) m/z 341 (M+H). $^1$H NMR (500 MHz, DMSO-d$_6$) δ 7.99-7.89 (m, 2H), 7.46 (d, J=1.7 Hz, 1H), 6.81 (d, J=1.7 Hz, 1H), 6.15 (br. s., 1H), 5.67 (s, 2H), 3.95 (s, 3H).

The compounds in the following table were synthesized in an analogous manner to Example 96 via a Suzuki reaction between the appropriate aryl halide and the corresponding boronic acid/ester, followed by deprotection of the trityl groups.

| Ex. No. | Structure | Name | Molecular Ion |
|---|---|---|---|
| 97 | 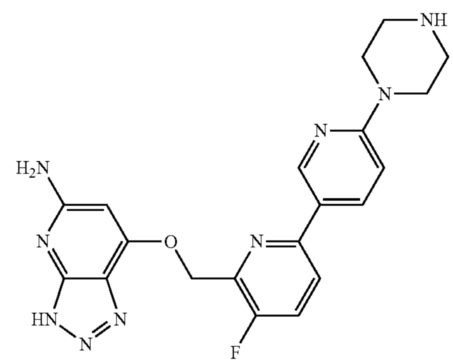 [SMILES: Nc1cc(OCc2nc(-c3ccc(N4CCNCC4)nc3)ccc2F)c2nn[nH]c2n1] | 7-((5-fluoro-6'-(piperazin-1-yl)-[2,3'-bipyridin]-6-yl)methoxy)-3H-[1,2,3]triazolo[4,5-b]pyridin-5-amine | MS (ESI) 422 [M + H]$^+$ |
| 98 | 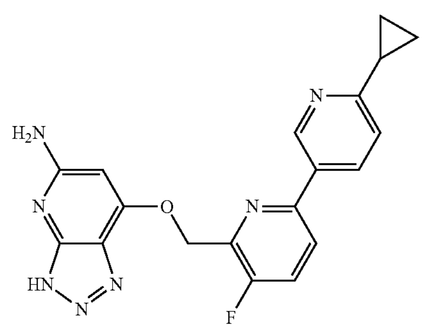 [SMILES: Nc1cc(OCc2nc(-c3ccc(C4CC4)nc3)ccc2F)c2nn[nH]c2n1] | 7-((6'-cyclopropyl-5-fluoro-[2,3'-bipyridin]-6-yl)methoxy)-3H-[1,2,3]triazolo[4,5-b]pyridin-5-amine | MS (ESI) 378 [M + H]$^+$ |
| 99 | 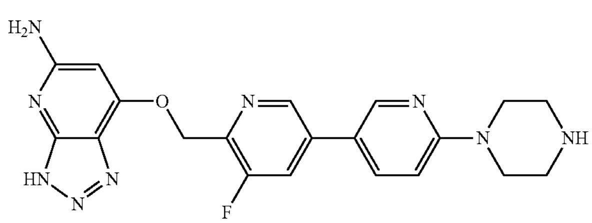 [SMILES: Nc1cc(OCc2ncc(-c3ccc(N4CCNCC4)nc3)cc2F)c2nn[nH]c2n1] | 7-((5-fluoro-6'-(piperazin-1-yl)-[3,3'-bipyridin]-6-yl)methoxy)-3H-[1,2,3]triazolo[4,5-b]pyridin-5-amine | MS (ESI) 422 [M + H]$^+$ |
| 100 | 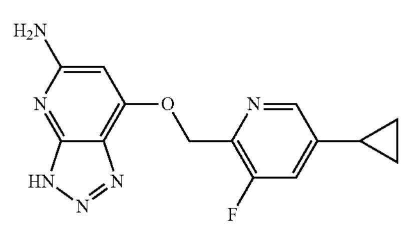 [SMILES: Nc1cc(OCc2ncc(C3CC3)cc2F)c2nn[nH]c2n1] | 7-((5-cyclopropyl-3-fluoropyridin-2-yl)methoxy)-3H-[1,2,3]triazolo[4,5-b]pyridin-5-amine | MS (ESI) 301 [M + H]$^+$ |

| Ex. No. | Structure | Name | Molecular Ion |
|---|---|---|---|
| 101 | 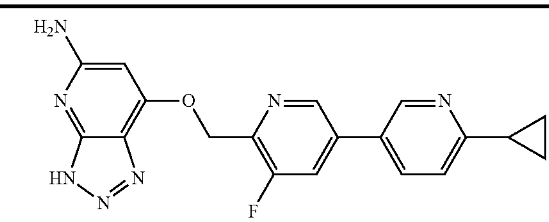 | 7-((6'-cyclopropyl-5-fluoro-[3,3'-bipyridin]-6-yl)methoxy)-3H-[1,2,3]triazolo[4,5-b]pyridin-5-amine | MS (ESI) 378 [M + H]$^+$ |
| 102 | 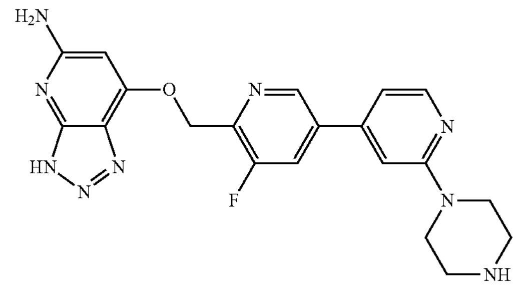 [SMILES: Nc1cc(OCc2ncc(-c3ccnc(N4CCNCC4)c3)cc2F)c2nn[nH]c2n1] | 7-((5-fluoro-2'-(piperazin-1-yl)-[3,4'-bipyridin]-6-yl)methoxy)-3H-[1,2,3]triazolo[4,5-b]pyridin-5-amine | MS (ESI) 422 [M + H]$^+$ |
| 103 | 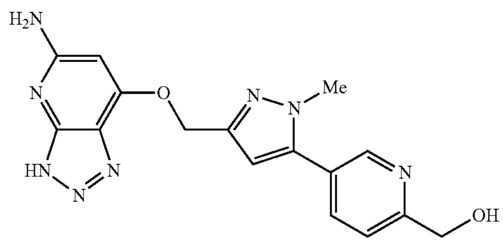 [SMILES: Cn1nc(COc2cc(N)nc3[nH]nnc23)cc1-c1ccc(CO)nc1] | (5-(3-(((5-amino-3H-[1,2,3]triazolo[4,5-b]pyridin-7-yl)oxy)methyl)-1-methyl-1H-pyrazol-5-yl)pyridin-2-yl)methanol | MS (ESI) 353 [M + H]$^+$ |
| 104 | 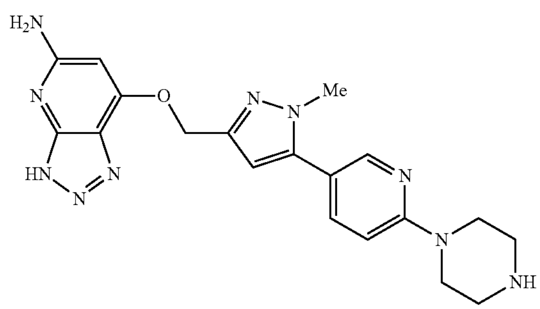 [SMILES: Cn1nc(COc2cc(N)nc3[nH]nnc23)cc1-c1ccc(N2CCNCC2)nc1] | 7-((1-methyl-5-(6-(piperazin-1-yl)pyridin-3-yl)-1H-pyrazol-3-yl)methoxy)-3H-[1,2,3]triazolo[4,5-b]pyridin-5-amine | MS (ESI) 407 [M + H]$^+$ |
| 105 | 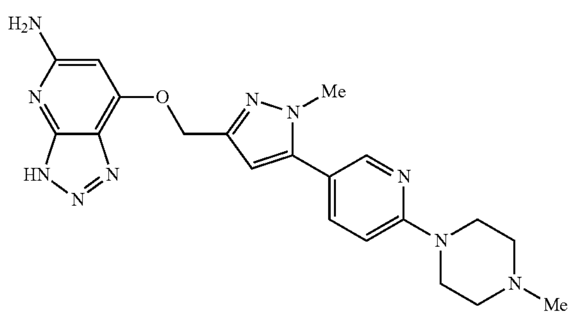 [SMILES: CN1CCN(c2ccc(-c3cc(COc4cc(N)nc5[nH]nnc45)nn3C)cn2)CC1] | 7-((1-methyl-5-(6-(4-methylpiperazin-1-yl)pyridin-3-yl)-1H-pyrazol-3-yl)methoxy)-3H-[1,2,3]triazolo[4,5-b]pyridin-5-amine | MS (ESI) 421 [M + H]$^+$ |
| 106 | 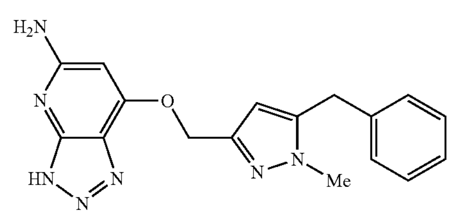 [SMILES: Cn1nc(COc2cc(N)nc3[nH]nnc23)cc1Cc1ccccc1] | 7-((5-benzyl-1-methyl-1H-pyrazol-3-yl)methoxy)-3H-[1,2,3]triazolo[4,5-b]pyridin-5-amine | MS (ESI) 336 [M + H]$^+$ |

-continued

| Ex. No. | Structure | Name | Molecular Ion |
|---|---|---|---|
| 107 | 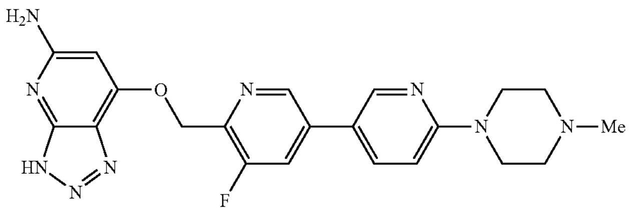 [SMILES: CN1CCN(c2ccc(-c3cnc(COc4cc(N)nc5[nH]nnc45)c(F)c3)cn2)CC1] | 7-((5-fluoro-6'-(4-methylpiperazin-1-yl)-[3,3'-bipyridin]-6-yl)methoxy)-3H-[1,2,3]triazolo[4,5-b]pyridin-5-amine | MS (ESI) 436 [M + H]+ |
| 108 | 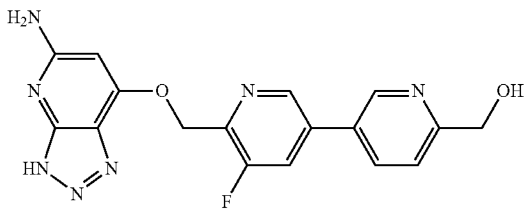 [SMILES: Nc1cc(OCc2ncc(-c3ccc(CO)nc3)cc2F)c2nn[nH]c2n1] | (6'-(((5-amino-3H-[1,2,3]triazolo[4,5-b]pyridin-7-yl)oxy)methyl)-5'-fluoro-[3,3'-bipyridin]-6-yl)methanol | MS (ESI) 368 [M + H]+ |
| 109 | 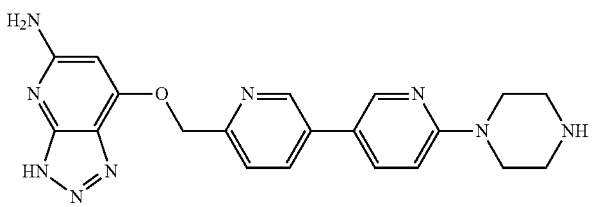 [SMILES: Nc1cc(OCc2ccc(-c3ccc(N4CCNCC4)nc3)cn2)c2nn[nH]c2n1] | 7-((6'-(piperazin-1-yl)-[3,3'-bipyridin]-6-yl)methoxy)-3H-[1,2,3]triazolo[4,5-b]pyridin-5-amine | MS (ESI) 404 [M + H]+ |
| 110 | 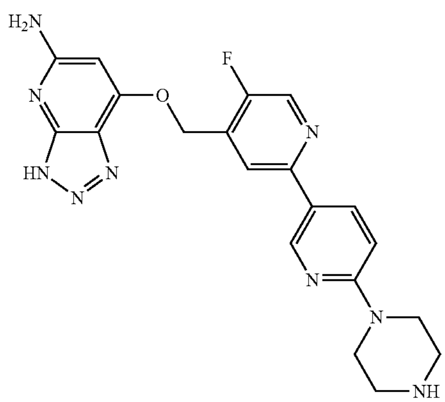 [SMILES: Nc1cc(OCc2cc(-c3ccc(N4CCNCC4)nc3)ncc2F)c2nn[nH]c2n1] | 7-((5-fluoro-6'-(piperazin-1-yl)-[2,3'-bipyridin]-4-yl)methoxy)-3H-[1,2,3]triazolo[4,5-b]pyridin-5-amine | MS (ESI) 422 [M + H]+ |
| 111 | 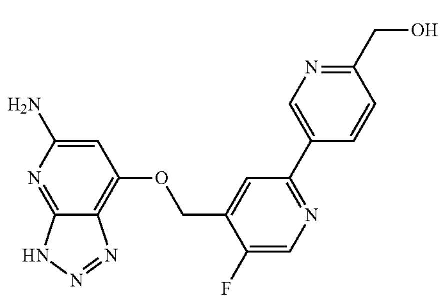 [SMILES: Nc1cc(OCc2cc(-c3ccc(CO)nc3)ncc2F)c2nn[nH]c2n1] | (4-(((5-amino-3H-[1,2,3]triazolo[4,5-b]pyridin-7-yl)oxy)methyl)-5-fluoro-[2,3'-bipyridin]-6'-yl)methanol | MS (ESI) 368 [M + H]+ |

Example 112: 7-(Benzofuran-4-ylmethoxy)-3H-[1,2,3]triazolo[4,5-d]pyrimidin-5-amine

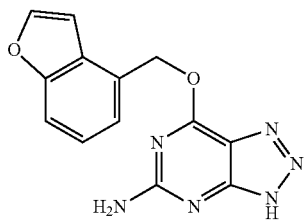 [SMILES: Nc1nc(OCc2cccc3occc23)c2nn[nH]c2n1]

Example 112A: 3-(5-Amino-7-(benzofuran-4-ylmethoxy)-3H-[1,2,3]triazolo[4,5-d]triazolo[4,5-d]pyrimidin-3-yl)propanenitrile

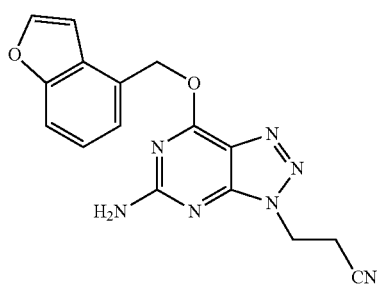 [SMILES: N#CCCn1nnc2c(OCc3cccc4occc34)nc(N)nc21]

To a solution of Intermediate 6 (0.10 g, 0.447 mmol) and benzofuran-4-ylmethanol (0.099 g, 0.67 mmol) in DME (2.2 mL) was added $K_2CO_3$ (0.19 g, 1.3 mmol) and the reaction mixture was heated at 80° C. overnight. The solution was filtered and concentrated, and the residue purified by silica gel chromatography to furnish Intermediate 112A. MS (ESI) m/z 336.1 (M+H).

Example 112

To a solution of Intermediate 112A (0.083 g, 0.25 mmol) in THF (2.5 mL) at 0° C. was added KOtBu (0.25 mL, 0.25 mmol). After 30 min, the reaction was quenched with AcOH (0.011 mL, 0.19 mmol), then concentrated. The residue was purified by preparative HPLC to furnish Example 112 (0.0034 g, 0.012 mmol, 4.9% yield). MS (ESI) m/z 283.1 (M+H). $^1$H NMR (500 MHz, DMSO-$d_6$) δ 8.05 (d, J=2.2 Hz, 1H), 7.63 (s, 1H), 7.44 (s, 1H), 7.39-7.31 (m, 1H), 7.18 (d, J=1.4 Hz, 1H), 7.07-6.99 (m, 2H), 5.84 (s, 2H).

The compounds in the following table were synthesized in an analogous manner to Example 112 via Intermediate 6 and the appropriate alcohol followed by deprotection of the ethylcyano group with tert-butoxide.

| Ex. No. | Structure | Name | Molecular Ion |
|---|---|---|---|
| 113 | 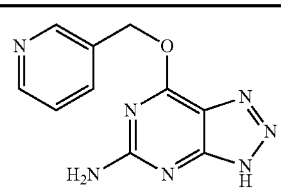 | 7-(pyridin-3-ylmethoxy)-3H-[1,2,3]triazolo[4,5-d]pyrimidin-5-amine | MS (ESI) 244 [M + H]⁺ |
| 114 | 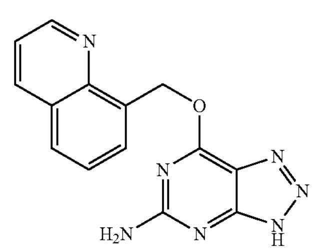 [SMILES: Nc1nc(OCc2cccc3cccnc23)c2nn[nH]c2n1] | 7-(quinolin-8-ylmethoxy)-3H-[1,2,3]triazolo[4,5-d]pyrimidin-5-amine | MS (ESI) 294 [M + H]⁺ |
| 115 | 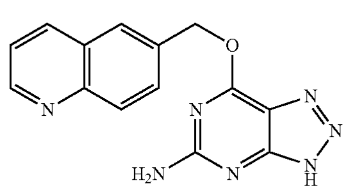 [SMILES: Nc1nc(OCc2ccc3ncccc3c2)c2nn[nH]c2n1] | 7-(quinolin-6-ylmethoxy)-3H-[1,2,3]triazolo[4,5-d]pyrimidin-5-amine | MS (ESI) 294 [M + H]⁺ |

-continued

| Ex. No. | Structure | Name | Molecular Ion |
|---|---|---|---|
| 116 | 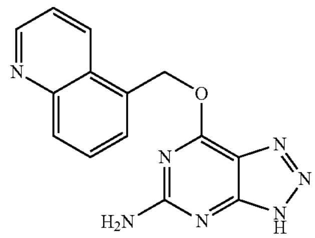 [SMILES: Nc1nc(OCc2cccc3ncccc23)c2nn[nH]c2n1] | 7-(quinolin-5-ylmethoxy)-3H-[1,2,3]triazolo[4,5-d]pyrimidin-5-amine | MS (ESI) 294 [M + H]+ |
| 117 | 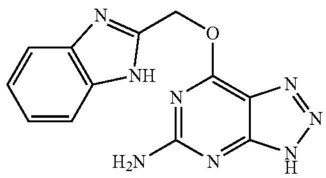 [SMILES: Nc1nc(OCc2nc3ccccc3[nH]2)c2nn[nH]c2n1] | 7-((1H-benzo[d]imidazol-2-yl)methoxy)-3H-[1,2,3]triazolo[4,5-d]pyrimidin-5-amine | MS (ESI) 283 [M + H]+ |
| 118 | 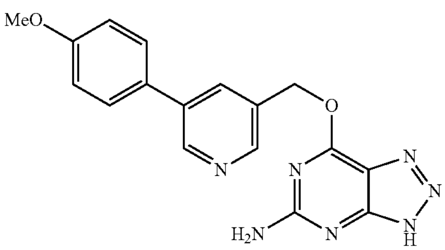 [SMILES: COc1ccc(-c2cncc(COc3nc(N)nc4[nH]nnc34)c2)cc1] | 7-((5-(4-methoxyphenyl)pyridin-3-yl)methoxy)-3H-[1,2,3]triazolo[4,5-d]pyrimidin-5-amine | MS (ESI) 350 [M + H]+ |
| 119 | 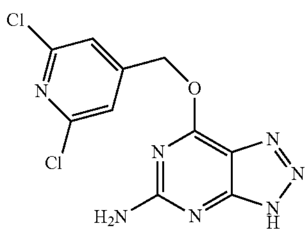 [SMILES: Nc1nc(OCc2cc(Cl)nc(Cl)c2)c2nn[nH]c2n1] | 7-((2,6-dichloropyridin-4-yl)methoxy)-3H-[1,2,3]triazolo[4,5-d]pyrimidin-5-amine | MS (ESI) 312 [M + H]+ |
| 120 | 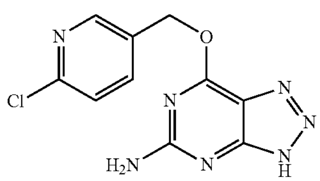 [SMILES: Nc1nc(OCc2ccc(Cl)nc2)c2nn[nH]c2n1] | 7-((6-chloropyridin-3-yl)methoxy)-3H-[1,2,3]triazolo[4,5-d]pyrimidin-5-amine | MS (ESI) 287 [M + H]+ |
| 121 | 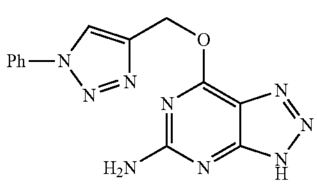 [SMILES: Nc1nc(OCc2cn(-c3ccccc3)nn2)c2nn[nH]c2n1] | 7-((1-phenyl-1H-1,2,3-triazol-4-yl)methoxy)-3H-[1,2,3]triazolo[4,5-d]pyrimidin-5-amine | MS (ESI) 310 [M + H]+ |
| 122 | 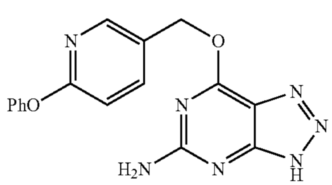 [SMILES: Nc1nc(OCc2ccc(Oc3ccccc3)nc2)c2nn[nH]c2n1] | 7-((6-phenoxypyridin-3-yl)methoxy)-3H-[1,2,3]triazolo[4,5-d]pyrimidin-5-amine | MS (ESI) 336 [M + H]+ |

| Ex. No. | Structure | Name | Molecular Ion |
|---|---|---|---|
| 123 | 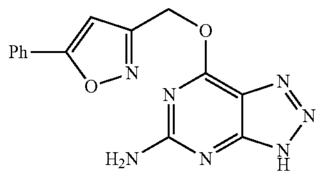 [SMILES: Nc1nc(OCc2cc(-c3ccccc3)on2)c2nn[nH]c2n1] | 7-((5-phenylisoxazol-3-yl)methoxy)-3H-[1,2,3]triazolo[4,5-d]pyrimidin-5-amine | MS (ESI) 310 [M + H]+ |
| 124 | 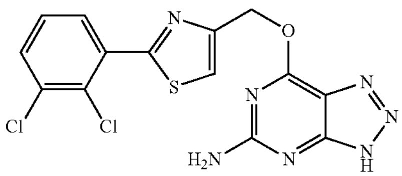 [SMILES: Nc1nc(OCc2csc(-c3cccc(Cl)c3Cl)n2)c2nn[nH]c2n1] | 7-((2-(2,3-dichlorophenyl)thiazol-4-yl)methoxy)-3H-[1,2,3]triazolo[4,5-d]pyrimidin-5-amine | MS (ESI) 394 [M + H]+ |
| 125 | 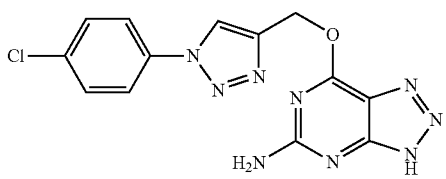 [SMILES: Nc1nc(OCc2cn(-c3ccc(Cl)cc3)nn2)c2nn[nH]c2n1] | 7-((1-(4-chlorophenyl)-1H-1,2,3-triazol-4-yl)methoxy)-3H-[1,2,3]triazolo[4,5-d]pyrimidin-5-amine | MS (ESI) 344 [M + H]+ |
| 126 | 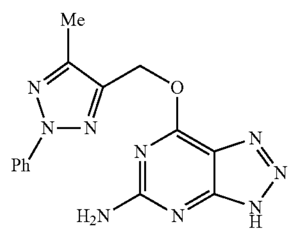 [SMILES: Cc1nn(-c2ccccc2)nc1COc1nc(N)nc2[nH]nnc12] | 7-((5-methyl-2-phenyl-2H-1,2,3-triazol-4-yl)methoxy)-3H-[1,2,3]triazolo[4,5-d]pyrimidin-5-amine | MS (ESI) 324 [M + H]+ |

What is claimed is:

1. The compound of the formula (I)

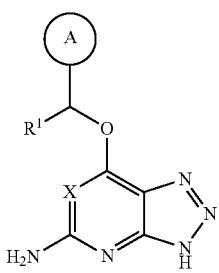

(I)

or a stereoisomer, a tautomer, or a pharmaceutically acceptable salt thereof, wherein:

ring A is independently a 5- to 10-membered heterocycle comprising carbon atoms and 1-4 heteroatoms selected from N, $NR^a$, O, and $S(O)_p$; wherein said heterocycle is substituted with 0-1 $R^2$ and 0-4 $R^3$;

X is independently CH or N;

$R^1$ is independently selected from: H, CN, $C_{1-6}$ alkyl, and $C_{1-6}$ haloalkyl;

provided that ring A is other than thienyl substituted with halogen, when X is N and $R^1$ is H;

$R^2$ is independently selected from: $SF_5$, $-(CH_2)_rOH$, $-(CH_2)_nR^4$, and $-(CH_2)_n(X_1)_n(CH_2)_nR^5$;

$X_1$ is independently selected from: O, S, CO and $SO_2$;

$R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);

$R^4$ is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, CN, $CO_2(C_{1-4}$ alkyl), $NO_2$, $NR^6R^7$, $CONR^6R^7$, $NHCOR^8$, $NHCO_2R^8$, $COR^{10}$, $SO_2NR^9R^{10}$, and $S(O)_pR^8$;

$R^5$ is independently selected from: $C_{3-10}$ carbocycle substituted with 0-2 $R^{11}$, phenyl substituted with 0-3 $R^{11}$ and 0-1 $R^{12}$, and 5- to 10-membered heterocycle comprising carbon atoms and 1-4 heteroatoms selected from N, $NR^a$, O, and $S(O)_p$; wherein said heterocycle is substituted with 0-2 $R^{11}$ and 0-1 $R^{13}$;

$R^6$ is, at each occurrence, independently selected from: H, $C_{1-4}$ haloalkyl, $C_{1-6}$ alkyl substituted with 0-2 $R^{15}$, $-(CH_2)_r-(C_{3-6}$ cycloalkyl substituted with 0-1 $R^{14}$), $-(CHR^b)_n$-(phenyl substituted with 0-1 $R^{16}$), $-(CH_2)_r$-(phenyl substituted with 0-1 $R^{16}$), $-(CH_2)_r$-(a 5- to 10-membered heterocycle comprising carbon atoms and 1-4 heteroatoms selected from N, $NR^a$, O, and $S(O)_p$, wherein said heterocycle is substituted with 0-1 $R^{17}$);

$R^7$ is, at each occurrence, independently selected from: H and $C_{1-4}$ alkyl substituted with $R^{11}$;

$R^8$ is, at each occurrence, independently selected from: $C_{1-4}$ alkyl, $-(CH_2)_r-C_{3-6}$ cycloalkyl, and $-(CH_2)_r$-phenyl;

$R^9$ is, at each occurrence, independently selected from: H and $C_{1-4}$ alkyl;

$R^{10}$ is, at each occurrence, independently selected from: $R^8$ and H;

$R^{11}$ is, at each occurrence, independently selected from: OH, $NH_2$, halogen, $C_{1-4}$ alkoxy, $C_{1-4}$ haloalkyl, and $C_{1-4}$ haloalkoxy;

$R^{12}$ is independently selected from: halogen, CN, $C_{1-4}$ alkyl, $C_{1-4}$ alkoxy, $C_{1-4}$ haloalkyl, $C_{1-4}$ haloalkoxy, $C_{1-4}$ alkylthio, OH, $CH_2OH$, $CO_2H$, $CO_2(C_{1-4}$ alkyl), $NH_2$, $CH_2NH_2$, $N(C_{1-4}$ alkyl$)_2$, $CH_2N(C_{1-4}$ alkyl$)_2$, $CONH_2$, $CON(C_{1-4}$ alkyl$)_2$, $SO_2NH_2$, $SO_2NH(C_{1-4}$ alkyl), $SO_2N(C_{1-4}$ alkyl$)_2$, CONHPh, NHCOPh, —$(CH_2)_n$—$(C_{3-6}$ carbocycle substituted with 0-2 $R^c$), (a 5- to 6-membered heterocycle comprising carbon atoms and 1-4 heteroatoms selected from N, $NR^a$, O, and $S(O)_p$, wherein said heterocycle is substituted with 0-2 $R^c$),

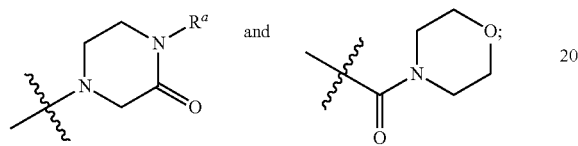
and $R^{13}$ is independently selected from: $R^{12}$ and =O;

$R^{14}$ and $R^{16}$ are, at each occurrence, independently selected from: halogen, $C_{1-4}$ alkyl, $C_{1-4}$ alkoxy, $C_{1-4}$ haloalkyl, $C_{1-4}$ haloalkoxy, OH, $CH_2OH$, $N(C_{1-4}$ alkyl$)_2$, $CONH_2$, $CONH(C_{1-4}$ alkyl), $CON(C_{1-4}$ alkyl$)_2$, $OCH_2CONH_2$, $NHCO(C_{1-4}$ alkyl), $NHCO_2(C_{1-4}$ alkyl), $SO_2(C_{1-4}$ alkyl), —$(CH_2)_n$-phenyl, —O—$(CH_2)_n$-phenyl, and pyridylmethyl;

$R^{15}$ is, at each occurrence, independently selected from: OH, $C_{1-4}$ alkoxy, $C_{1-4}$ haloalkyl, $C_{1-4}$ haloalkoxy, $N(C_{1-4}$ alkyl$)_2$, $CONH_2$, $CONH(C_{1-4}$ alkyl), and $CON(C_{1-4}$ alkyl$)_2$;

$R^{17}$ is independently selected from: $R^{14}$ and =O;

$R^a$ is, at each occurrence, independently selected from the group consisting of H, $C_{1-4}$ alkyl, $CO(C_{1-4}$ alkyl), $CO_2(C_{1-4}$ alkyl), $SO_2(C_{1-4}$ alkyl), —$(CH_2)_n$-(pyrrolidinyl substituted with 0-1 $R^c$), —$(CH_2)_n$-(phenyl substituted with 0-1 $R^c$), and —$CO(-(CH_2)_n$-phenyl substituted with 0-1 $R^c$);

$R^b$ is, at each occurrence, independently selected from: H and $C_{1-4}$ alkyl;

$R^c$ is, at each occurrence, independently selected from: OH, $NH_2$, $C_{1-4}$ alkyl, halogen, $C_{1-4}$ alkoxy, $C_{1-4}$ haloalkyl, $C_{1-4}$ haloalkoxy, pyrrolidinyl, —$(CH_2)_n$-piperidinyl, Ph, and OPh;

n is, at each occurrence, independently selected from: 0 and 1;

p is, at each occurrence, independently selected from: 0, 1 and 2; and t is, at each occurrence, independently selected from: 0, 1, 2, 3 and 4.

2. A compound according to claim 1 or a stereoisomer, a tautomer, or a pharmaceutically acceptable salt thereof, wherein:

$R^2$ is independently selected from: halogen, CN, $CH_2OH$, $C_{1-4}$ alkyl, —$CH_2$—$C_{1-4}$ alkoxy, $C_{1-4}$ alkoxy, $C_{1-4}$ haloalkyl, $C_{1-4}$ haloalkoxy, $C_{1-4}$ haloalkylthio, $SF_5$, $CO_2(C_{1-4}$ alkyl), $NR^6R^7$, $CONR^6R^7$, —$NHCO(C_{1-4}$ alkyl), $NO_2$, $SO_2NR^8R^9$, $SO_2R^8$, —$(O)_{0-1}$—$(C_{3-6}$ cycloalkyl), —$(O)_{0-1}$—$(CH_2)_{0-1}$-(phenyl substituted with 0-1 $R^{11}$ and 0-1 $R^{12}$), and —$(CH_2)_{0-1}$-(a heterocycle substituted with 0-1 $R^{11}$ and 0-1 $R^{13}$, wherein said heterocycle is a 5- to 10-membered heterocycle comprising carbon atoms and 1-4 heteroatoms selected from N, $NR^a$, O, and S);

$R^6$ is independently selected from: H, $C_{1-4}$ haloalkyl, and $C_{1-6}$ alkyl;

$R^{12}$ and $R^{13}$ are, at each occurrence, independently selected from: halogen, CN, $C_{1-4}$ alkyl, $C_{1-4}$ alkoxy, $C_{1-4}$ haloalkyl, $C_{1-4}$ haloalkoxy, $CH_2OH$, $CO_2(C_{1-4}$ alkyl), $SO_2(C_{1-4}$ alkyl), $C_{3-6}$ cycloalkyl, $CON(C_{1-4}$ alkyl$)_2$, $SO_2NH_2$, $SO_2NH(C_{1-4}$ alkyl), $SO_2N(C_{1-4}$ alkyl$)_2$, Ph, Bn, CONHPh, NHCOPh, pyrazolyl, pyrrolidinyl, piperidinyl, morpholinyl, piperazinyl,

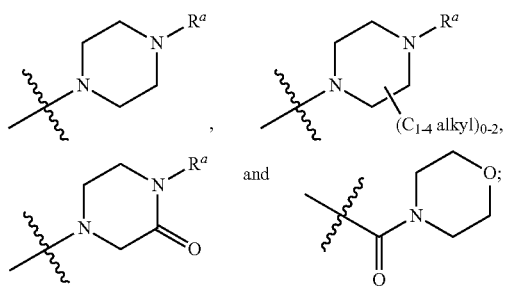

$R^{15}$ is, at each occurrence, independently selected from: OH, $C_{1-4}$ alkyl, $C_{1-4}$ alkoxy, $C_{1-4}$ haloalkyl, $N(C_{1-4}$ alkyl$)_2$, $CONH_2$, $CONH(C_{1-4}$ alkyl), and $CON(C_{1-4}$ alkyl$)_2$; and $R^{16}$ is independently selected from: halogen, $C_{1-4}$ alkoxy, and $SO_2(C_{1-4}$ alkyl).

3. A compound according to claim 2 of formula (II)

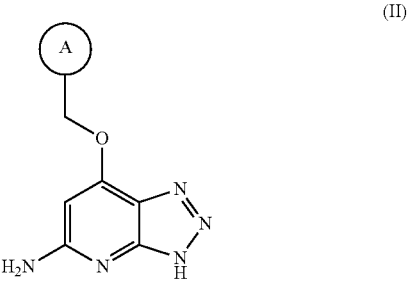

or a stereoisomer, a tautomer, or a pharmaceutically acceptable salt thereof.

4. A compound according to claim 2 of the formula (IIa)

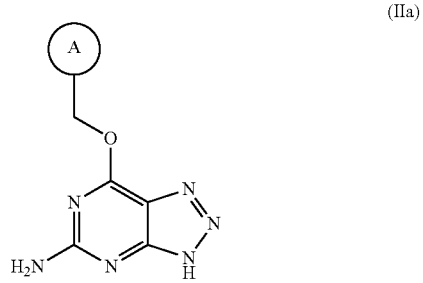

or a stereoisomer, a tautomer, or a pharmaceutically acceptable salt thereof, provided that ring A is other than thienyl substituted with halogen.

5. A compound according to claim 1
or a stereoisomer, a tautomer, or a pharmaceutically acceptable salt thereof, wherein:
ring A is independently selected from:

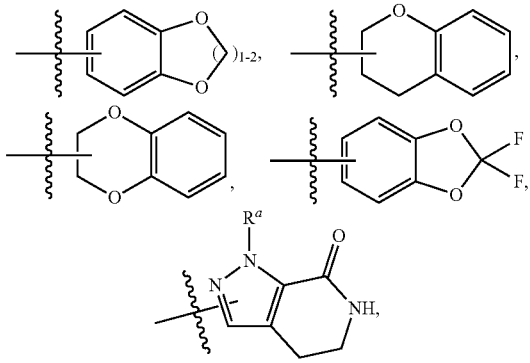

and a 5- to 10-membered heteroaryl comprising carbon atoms and 1-4 heteroatoms selected from N, NR$^a$, O, and S; wherein each ring moiety is substituted with 0-1 R$^2$ and 0-2 R$^3$; provided that ring A is other than thienyl substituted with halogen, when X is N and R$^1$ is H in Formula (I);

R$^2$ is independently selected from: SF$_5$, halogen, CN, CH$_2$OH, C$_{1-4}$ alkyl, C$_{1-4}$ alkoxy, C$_{1-4}$ haloalkyl, C$_{1-4}$ haloalkoxy, C$_{1-4}$ haloalkylthio, —CH$_2$(C$_{1-4}$ alkoxy), —(O)$_{0-1}$—(C$_{3-6}$ cycloalkyl), —(O)$_{0-1}$—(CH$_2$)$_{0-1}$-(phenyl substituted with 0-1 R$^{11}$ and 0-1 R$^{12}$), (pyridyl substituted with 0-1 R$^{11}$ and 0-1 R$^{13}$), and

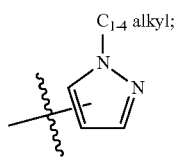

R$^3$ is, at each occurrence, independently selected from: halogen, CN, C$_{1-4}$ alkyl, C$_{1-4}$ alkoxy, C$_{1-4}$ haloalkyl, C$_{1-4}$ haloalkoxy, NO$_2$, CONH$_2$, and SO$_2$(C$_{1-4}$ alkyl);
R$^{11}$ is, at each occurrence, independently selected from: halogen, NH$_2$, C$_{1-4}$ alkoxy, C$_{1-4}$ haloalkyl, and C$_{1-4}$ haloalkoxy;
R$^{12}$ and R$^{13}$ are, at each occurrence, independently selected from: halogen, CN, C$_{1-4}$ alkyl, C$_{1-4}$ alkoxy, C$_{1-4}$ haloalkyl, C$_{1-4}$ haloalkoxy, CH$_2$OH, CO$_2$(C$_{1-4}$ alkyl), SO$_2$(C$_{1-4}$ alkyl), C$_{3-6}$ cycloalkyl, CON(C$_{1-4}$ alkyl)$_2$, SO$_2$NH$_2$, SO$_2$NH(C$_{1-4}$ alkyl), SO$_2$N(C$_{1-4}$ alkyl)$_2$, Ph, CONHPh, NHCOPh, pyrazolyl,

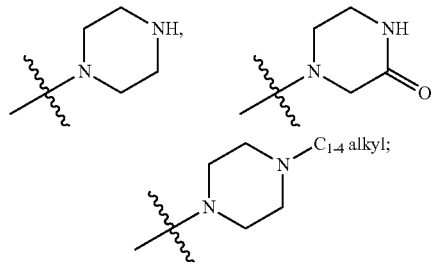

R$^a$ is, at each occurrence, independently selected from the group consisting of H, C$_{1-4}$ alkyl, CO(C$_{1-4}$ alkyl), CO$_2$(C$_{1-4}$ alkyl), SO$_2$(C$_{1-4}$ alkyl), —(CH$_2$)$_n$—(C$_{3-6}$ cycloalkyl substituted with 0-1 R$^c$), —(CH$_2$)$_n$-(phenyl substituted with 0-1 R$^c$), —CO(—(CH$_2$)$_n$-phenyl), —(CH$_2$)$_n$-(pyrrolidinyl substituted with 0-1 R$^c$), —(CH$_2$)$_n$-(imidazolyl substituted with 0-1 R$^c$), —(CH$_2$)$_n$-(piperidinyl substituted with 0-1 R$^c$), —(CH$_2$)$_n$-(pyridyl substituted with 0-1 R$^c$), and —(CH$_2$)$_n$-(pyrimidinyl substituted with 0-1 R$^c$).

6. A compound according to claim 5
or a stereoisomer, a tautomer, or a pharmaceutically acceptable salt, wherein:
ring A is independently selected from: furanyl, oxazolyl, thiazolyl, isoxazolyl, oxadiazolyl, pyridyl, pyrimidinyl, benzofuranyl, quinolinyl,

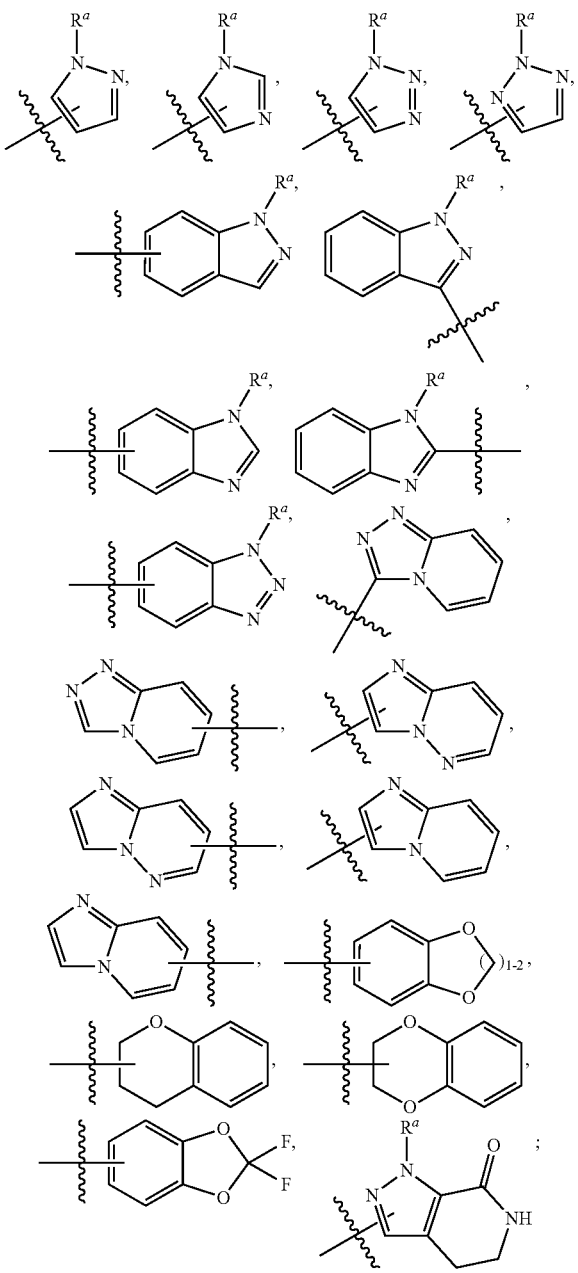

wherein each ring moiety is substituted with 0-1 $R^2$ and 0-1 $R^3$;

$R^2$ is, at each occurrence, independently selected from: $SF_5$, halogen, $C_{1-4}$ alkyl, $C_{1-4}$ alkoxy, $C_{1-4}$ haloalkyl, $C_{1-4}$ haloalkoxy, $CH_2OH$, —$CH_2(C_{1-4}$ alkoxy), —$(O)_{0-1}$—$(C_{3-6}$ cycloalkyl), —$(O)_{0-1}$—$(CH_2)_{0-1}$-(phenyl substituted with 0-2 $R^{12}$), pyridyl substituted with 0-1 $R^{13}$, and

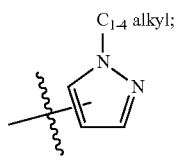

$R^3$ is, at each occurrence, independently selected from: CN, halogen, $C_{1-4}$ alkyl, and $C_{1-4}$ haloalkyl; and $R^{12}$ and $R^{13}$ are, at each occurrence, independently selected from: halogen, CN, $C_{1-4}$ alkyl, $C_{1-4}$ alkoxy, $C_{1-4}$ haloalkyl, $CH_2OH$, $NH(C_{1-4}$ alkyl), $SO_2(C_{1-4}$ alkyl), $C_{3-6}$ cycloalkyl,

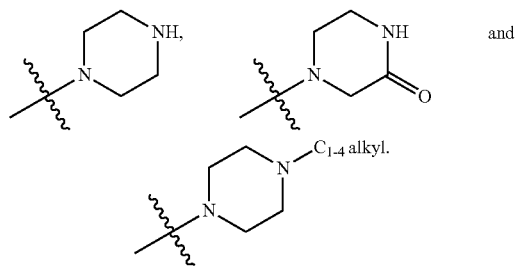

7. A compound according to claim 6 or a stereoisomer, a tautomer, or a pharmaceutically acceptable salt thereof, wherein:

ring A is independently selected from: furanyl, oxazolyl, thiazolyl, isoxazolyl, oxadiazolyl, pyridyl, pyrimidinyl, quinolinyl,

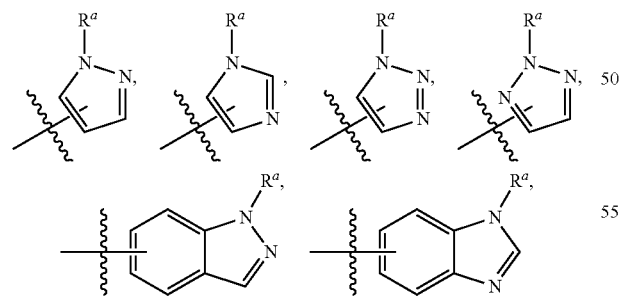

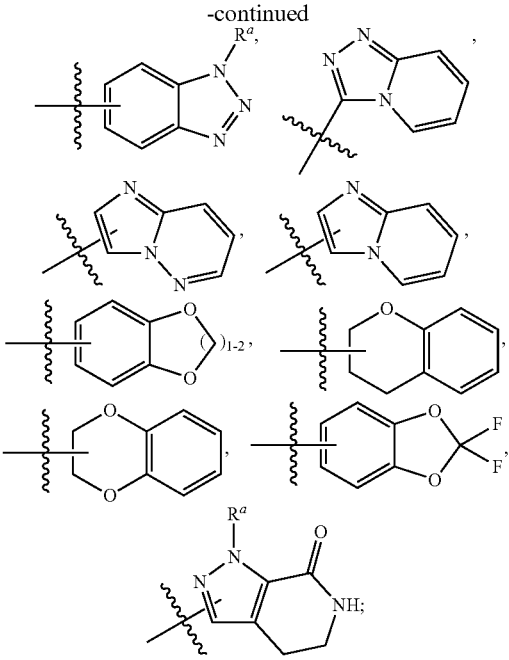

wherein each ring moiety is substituted with 0-1 $R^2$ and 0-1 $R^3$.

8. A compound according to claim 6 or a stereoisomer, a tautomer, or a pharmaceutically acceptable salt thereof, wherein:

ring A is independently selected from: isoxazolyl, thiazolyl, pyridyl, benzofuranyl, quinolinyl,

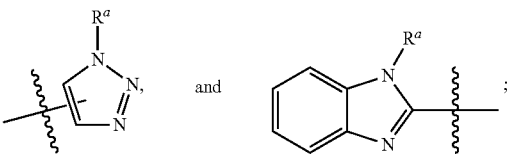

wherein each ring moiety is substituted with 0-1 $R^2$ and 0-1 $R^3$;

$R^2$ is, at each occurrence, independently selected from: halogen, $C_{1-4}$ alkyl, $C_{1-4}$ alkoxy, $C_{1-4}$ haloalkyl, $C_{1-4}$ haloalkoxy, —$(O)_{0-1}$—$(CH_2)_{0-1}$-(phenyl substituted with 0-2 $R^{12}$), and pyridyl substituted with 0-1 $R^{13}$;

$R^{12}$ and $R^{13}$ are, at each occurrence, independently selected from: halogen, CN, $C_{1-4}$ alkyl, $C_{1-4}$ alkoxy, and $C_{1-4}$ haloalkyl; and $R^a$ is, at each occurrence, independently selected from the group consisting of H, $C_{1-4}$ alkyl, and —$(CH_2)_n$-(phenyl substituted with 0-1 $R^c$).

9. A pharmaceutical composition, comprising a pharmaceutically acceptable carrier and a compound of any one of claims 1-8, or a stereoisomer, a tautomer, or a pharmaceutically acceptable salt thereof.

* * * * *

UNITED STATES PATENT AND TRADEMARK OFFICE
CERTIFICATE OF CORRECTION

PATENT NO. : 9,920,075 B2  
APPLICATION NO. : 15/510168  
DATED : March 20, 2018  
INVENTOR(S) : Wurtz et al.

Page 1 of 1

It is certified that error appears in the above-identified patent and that said Letters Patent is hereby corrected as shown below:

In the Claims

Claim 1, Column 111, Line 67:
Delete "0," and insert -- O, --.

Signed and Sealed this
Sixteenth Day of October, 2018

Andrei Iancu
*Director of the United States Patent and Trademark Office*